United States Patent [19]
Masaki et al.

[11] Patent Number: 5,821,179
[45] Date of Patent: Oct. 13, 1998

[54] ABSORBENT SHEET PROCESS FOR PRODUCING THE SAME AND ABSORBENT ARTICLE USING THE SAME

[75] Inventors: Kazumichi Masaki, Kochi-ken; Yoshihito Kubota, Tosa; Eichi Ichikawa; Mari Kaganoi, both of Kochi; Minoru Nakanishi, Tochigi-ken; Mitsugu Hamajima, Tochigi-ken; Yasuhiro Y. Yamamoto, Tochigi-ken; Hironori Kawasaki, Tochigi-ken; Tetsuya Kusagawa, Tochigi-ken, all of Japan

[73] Assignee: Kao Corporation, Tokyo, Japan

[21] Appl. No.: 580,521

[22] Filed: Dec. 28, 1995

[30] Foreign Application Priority Data

Dec. 28, 1994 [JP] Japan ................................. 6-328854
Dec. 28, 1994 [JP] Japan ................................. 6-348802

[51] Int. Cl.$^6$ ........................................ B32B 5/16
[52] U.S. Cl. ..................... 442/375; 442/381; 442/393; 604/367
[58] Field of Search .................... 428/283, 284, 428/297, 298, 288; 604/358, 367; 422/375, 381, 393

[56] References Cited

U.S. PATENT DOCUMENTS

| | | | |
|---|---|---|---|
| 3,070,095 | 12/1962 | Torr | 128/284 |
| 3,670,731 | 6/1972 | Harmon | 128/284 |
| 4,605,402 | 8/1986 | Iskra | 604/379 |
| 5,021,050 | 6/1991 | Iskra | 604/379 |

FOREIGN PATENT DOCUMENTS

| | | |
|---|---|---|
| 0394812 | 10/1990 | European Pat. Off. . |
| 0528248 | 2/1993 | European Pat. Off. . |
| 0661030 | 7/1995 | European Pat. Off. . |
| 59-26467 | 6/1959 | Japan . |
| 54-123293 | 9/1979 | Japan . |
| 54-141099 | 11/1979 | Japan . |
| 60-139898 | 7/1985 | Japan . |
| 61-132697 | 6/1986 | Japan . |
| WO9214430 | 9/1992 | WIPO . |

*Primary Examiner*—James J. Bell

[57] ABSTRACT

The absorbent sheet comprising at least hydrophilic fibers and thermally fusible bonding fibers or a strengthening assistant, and a superabsorbent polymer is characterized in that the superabsorbent polymer is not present on an absorbent surface of the absorbent sheet for absorbing liquid but distributed inside the absorbent sheet, and is adhered and fixed to the hyrophilic fibers constituting the absorbent sheet, the superabsorbent polymer is spread at an amount of 5 to 300 g per 1 $m^2$ of the absorbent sheet and the absorbent sheet has thickness of 0.3 to 1.5 mm.

15 Claims, 10 Drawing Sheets

ABSORBENT SHEET PROCESS FOR PRODUCING THE SAME AND ABSORBENT ARTICLE USING THE SAME

BACKGROUND OF THE INVENTION

This invention relates to an absorbent sheet suitable for use in sanitary napkins, hygienic pads, disposable diapers, medical pads, nursing breast pads, drip sheets, kitchen paper towel, household cleaning sheets, undersheets for pet animals, and the like; a process for producing the same; and absorbent articles using the same.

Various methods for fixing a superabsorbent polymer in an absorbent structure to obtain an absorbent sheet are known. For example, U.S. Pat. No. 3,070,095 discloses a process comprising, as shown in FIG. 24, spreading a superabsorbent polymer 116 over a tissue 110, superposing another tissue 111 thereon, and pressing the superabsorbent polymer into tissues by means of a roller. According to this process, however, the superabsorbent polymer is merely fixed in a layer between a pair of tissue layers, so that the process cannot be applied to fixing of a large quantity of a superabsorbent polymer. If such an absorbent sheet as shown in FIG. 24 is used as an absorbent member of an absorbent article, the superabsorbent polymer 116 would be separated from the tissues 110 and 111 with the movement of a wearer to make gaps between the tissues 110 and 111, where a liquid to be absorbed might collect.

U.S. Pat. No. 3,670,731 discloses a process comprising interposing a superabsorbent polymer between a pair of paper-like layers, followed by embossing or quilting, to thereby fix the superabsorbent polymer at prescribed sites. This process cannot be escaped from the same problems as with the above-mentioned pressing by means of a roller.

Japanese Patent Publication 59-26467 and Japanese Patent Application Laid-Opens 54-123293 and 54-141099 disclose processes in which a superabsorbent polymer is spread over a tissue having previously been wetted by spraying steam or water, so that the polymer acquires stickiness and is thereby fixed between a pair of tissues. This process achieves fixation of a superabsorbent polymer to some extent but yet cannot completely prevent fall-off of the polymer. Besides, the amount of the polymer that can be fixed is still insufficient. In addition, the superabsorbent polymer swells in layers upon liquid absorption, sometimes resulting in absorption hindrance due to gel blocking.

Japanese Patent Laid-Open 61-132697 describes a process for producing absorbent paper containing a superabsorbent polymer, in which process a superabsorbent polymer is spread over paper before being dried in the course of paper making, followed by drying. According to this process, the amount of a superabsorbent polymer which can be fixed on paper is somewhat increased but to about 10 g/m$^2$ at the most, which is by no means deemed sufficient. In addition, the superabsorbent polymer, which is exposed on the surface of the final product, easily falls off through dynamic actions such as friction.

A method for fixing a superabsorbent polymer on a tissue, etc. via a hot-melt adhesive applied to the entire area of the tissue is also known. Although this method guarantees fixation of a superabsorbent polymer, the most part of the surface of the superabsorbent polymer is overlaid with a hot-melt adhesive and therefore hindered from absorbing and swelling.

Alternatively, it has been suggested to apply a hot-melt adhesive spirally. This method achieves efficient fixing of a superabsorbent polymer while minimizing hindrance to absorption and swelling. However, involvement of spiral application of a hot-melt adhesive makes the process and the equipment complicated. Further, because a large amount of a superabsorbent polymer is fixed in a layer, the polymer causes gel blocking on liquid absorption and is interfered with swelling.

On the other hand, absorbent sheets made of wood pulp prepared in a dry process are also known. In order to increase the strength of this type of absorbent sheets, incorporation of a chemical binder, synthetic pulp, low-melting synthetic fiber, etc. has been attempted, only to make the sheet hydrophobic and reduce the rate of absorption. If the sheet strength is low, the superabsorbent polymer swollen with a liquid will unfavorably break out of the sheet. The absorbent sheet may be overlaid with crepe paper to increase its surface strength, but this unfavorably incurs the cost. With any of these manipulations, however, fixation of the superabsorbent polymer to the wood pulp sheet is insufficient, and the problem that a superabsorbent polymer readily comes off still remains. There is another problem that the absorbent sheet cannot be strongly compressed without reducing its rate of liquid absorption.

A process for producing an absorbent sheet comprising in-situ polymerization to obtain a superabsorbent polymer as fixed on nonwoven fabric support is also known. However, where nonwoven fabric made of hydrophilic fibers is used, a particulate superabsorbent polymer cannot be produced, and the resulting polymer is fixed over the entire surface of the nonwoven fabric substantially uniformly and has a reduced liquid absorptivity. Where nonwoven fabric made of hydrophobic fibers is used, although a particulate superabsorbent polymer can be produced, the absorbent sheet unfavorably has a low rate of absorption unlike the nonwoven fabric comprising hydrophilic fibers because of its hydrophobic properties as a whole. Besides, in-situ polymerization is unavoidably accompanied by remaining of unreacted monomers, which limits the utility of the resulting absorbent sheet for the safety consideration.

U.S. Pat. Nos. 4,605,402 and 5,021,050 disclose absorbent members which are prepared by overlaying a fiber layer on a fiber web having a superabsorbent polymer spread thereon and have a structure in which the polymer is distributed and adhered to the fiber in the middle portion in the thickness direction of the absorbent member. Although prepared to be thinned under compression, these absorbent members are not formed into a sheet and therefore too thick to be used for various purposes. Further, due to a low density, the surface of these absorbent members exhibits low absorption performance. In addition, when absorbing liquid and getting wet, the absorbent members recover its original thickness by means of the resilient force of synthetic fibers so as to obtain absorbing spaces. Thus, these absorbent members are insufficient for obtaining a thinner absorbent article.

SUMMARY OF THE INVENTION

Accordingly, an object of the present invention is to provide an ultrathin absorbent sheet in the form of sheet in which a superabsorbent polymer is surely fixed without impairing the absorption characteristics inherent in a superabsorbent polymer.

Another object of the present invention is to provide an absorbent sheet which absorbs liquid very smoothly without leaving liquid on its surface, quickly leads the absorbed liquid to all the superabsorbent polymers, and fixes the liquid effectively.

A further object of the present invention is to provide an ultrathin absorbent sheet in which a superabsorbent polymer exerts its inherent absorption characteristics without causing gel blocking even when used for repeated absorption of liquid.

A still further object of the present invention is to provide a process for readily producing the absorbent sheet.

A still further object of the present invention is to provide an absorbent article which comprises the absorbent sheet and exhibits high absorption performance.

A still further object of the present invention is to provide an absorbent article which, in particular, is ultrathin, gives an excellent feeling during the use, and does not give an uncomfortable feeling even after absorbing body fluids.

As a result of extensive investigations, the inventors of the present invention have found that gel blocking of the superabsorbent polymer is effectively prevented, and a large quantity of the superabsorbent polymer can be fixed in the absorbent sheet by embedding the superabsorbent polymer in spaces formed among fibers constituting the absorbent sheet in the state that the fibers are wet.

The present invention is accomplished based on the above finding, and the above object is achieved by providing an absorbent sheet comprising at least hydrophilic fibers and thermally fusible bonding fibers or a strengthening assistant, and a superabsorbent polymer, the absorbent sheet being characterized in that:

the superabsorbent polymer is not present on an absorbent surface of the absorbent sheet for absorbing liquid but distributed inside the absorbent sheet, and is adhered and fixed to the hydrophilic fibers constituting the absorbent sheet;

the superabsorbent polymer is spread at an amount of 5 to 300 g per 1 m$^2$ of the absorbent sheet; and the absorbent sheet has a thickness of 0.3 to 1.5 mm (hereinafter referred to as "first absorbent sheet").

The present invention also provides a process which can preferably be used for the production of the first absorbent sheet, that is, a process for preparing an absorbent sheet comprising at least hydrophilic fibers and thermally fusible bonding fibers or a strengthening assistant, and a superabsorbent polymer, the process comprising the steps of;

spreading the superabsorbent polymer on a wet fiber web which is prepared by a wet process from an aqueous slurry comprising at least the hydrophilic fibers and the thermally bonding fibers or the strengthening assistant;

overlaying thereon a fiber aggregate comprising the hydrophilic fibers and the thermally fusible bonding fibers or the strengthening assistant; and drying a combination of the fiber web and the fiber aggregate to form a unitary body thereof.

The present invention also provides an absorbent article which preferably uses the first absorbent sheet, that is, an absorbent article comprising at least a liquid retentive absorbent member and a liquid permeable backsheet, the absorbent article being characterized in that:

the absorbent member comprises an absorbent sheet comprising at least hydrophilic fibers and thermally fusible bonding fibers or a strengthening assistant, and a superabsorbent polymer, wherein the superabsorbent polymer is not present on an absorbent surface of the absorbent sheet for absorbing liquid but distributed inside the absorbent sheet, and is adhered and fixed to the hydrophilic fibers constituting the absorbent sheet;

the superabsorbent polymer is spread at an amount of 5 to 300 g per 1 m$^2$ of the absorbent sheet; and the superabsorbent sheet has a thickness of 0.3 to 1.5 mm.

The present invention also provides an absorbent sheet, which comprises superabsorbent polymer particles, and a fiber structure comprising bulky hydrophilic cellulose fibers and thermally fusible bonding fibers or a strengthening assistant, the superabsorbent polymer particles being not present on an absorbent surface of the absorbent sheet for absorbing the liquid but distributed inside and fixed to the fiber structure; and the absorbent sheet having a thickness of 0.3 to 1.5 mm, and the superabsorbent polymer being spread at an amount of 20 to 70 g per 1 m$^2$ of the absorbent sheet.

The present invention also provides an absorbent article which preferably uses the above sheet, that is, an absorbent article for absorbing body fluids comprising at least a liquid retentive absorbent member and a liquid impermeable backsheet, the absorbent article being characterized in that:

the absorbent member comprises the absorbent sheet which comprises superabsorbent polymer particles, and a fiber structure comprising bulky hydrophilic cellulose fibers and thermally fusible bonding fibers or a strengthening assistant, the superabsorbent polymer particles being not present on an absorbent surface of the absorbent sheet for absorbing the liquid but distributed inside and fixed to the fiber structure, the absorbent sheet having a thickness of 0.3 to 1.5 mm, and the superabsorbent polymer being spread at an amount of 20 to 70 g per 1 m$^2$ of the absorbent sheet; and the absorbent article does not give uncomfortable feeling caused by absorption of the body fluids and swelling of the superabsorbent polymer particles during usage.

In this specification, the term "fiber web" means a web in which constituent fibers are not at all constrained to each other or constrained very slightly due to mechanical entanglement, frictional force, etc. and have an extremely high degree of freedom while wet, and, after drying the constituent fibers are firmly constrained to each other to take a sheet form; the term "fiber aggregate" means an aggregate of fibers which predominantly comprises fibers and takes a sheet form, and refers to ordinary paper, nonwoven fabric and woven fabric, and also to the above-mentioned fiber web; and the term "fiber structure" means a sheet-material of fibers which predominantly comprises the fiber web and the fiber aggregate to thereby form a unitary body. Hereinafter "fiber aggregate" is synonymous with first fiber layer; and "fiber web" is synonymous with second fiber layer.

According to the present invention, there is obtained an absorbent sheet in which a superabsorbent polymer is securely fixed therein so that it hardly falls off the sheet, and the superabsorbent polymer hardly causes gel blocking. The absorbent sheet of the present invention combines three functions of liquid permeation, diffusion and retention and exhibits high performance in terms of both absorption rate and absorption capacity. Although the absorbent sheet has quite an ultrathin thickness, it exhibits unexpected high absorption performance.

According to the preferred processes for producing the absorbent sheets of the present invention, the production speed is greatly increased as compared with conventional techniques. The processes of the present invention require no complicated steps for fixation of a superabsorbent polymer, achieving marked simplification of the production process.

The processes of the present invention allow a superabsorbent polymer to be spread not only all the area of the absorbent sheet but partly in stripes extending in the longitudinal direction or intermittently in the longitudinal direction of the absorbent sheet. That is, the area in which a superabsorbent polymer is spread can be designed in agreement with the end use, so that the absorbent sheet is economically produced.

The present invention provides ultrathin absorbent articles which contains a large amount of a superabsorbent in a fixed state notwithstanding their small thickness. The absorbent articles of the present invention have a high rate of liquid absorption, hardly cause a back-flow of absorbed liquid, and have a decreased incidence of leaks. Where an absorbent member of an absorbent article consists solely of the absorbent sheet of the present invention, the absorbent article can be manufactured through an extremely simplified production process at a high speed, in which the absorbent sheet is merely cut to size. Further, since the absorbent sheet comprises a fiber web and a fiber aggregate which form a unitary body, and a superabsorbent polymer is contained in the absorbent sheet, the superabsorbent polymer is prevented from separating from the absorbent sheet and reducing its absorption performance even when the wearer takes violet exercise.

DETAILED DESCRIPTION OF THE INVENTION

Figure 1A:
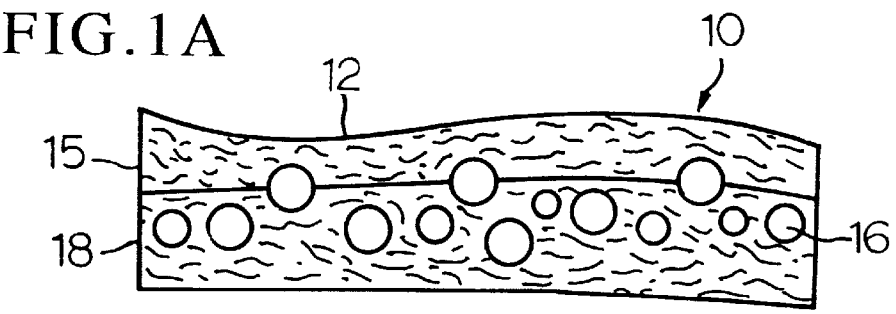
FIG. 1A is a diagrammatical schematic view illustrating the cross section of the first absorbent sheet of the present invention.

The first absorbent sheet of the present invention will be described in detail by referring to the accompanying drawings. FIG. 1A is a diagrammatical schematic cross section of the first absorbent sheet, and FIG. 1B is a schematic cross section of the first absorbent sheet.

The first absorbent sheet 10 according to the present invention comprises at least hydrophilic fine fibers, and thermally fusible bonding fibers or a strengthening assistant, and a superabsorbent polymer 16. The absorbent sheet 10 has an absorbent surface 12 for absorbing liquid, and the absorbent polymer is not present on the absorbent surface 12, and the absorbent polymer 16 is distributed inside the absorbent sheet 10. The superabsorbent polymer 16 is adhered to the hydrophilic fine fibers constituting the absorbent sheet 10.

Figure 1B:
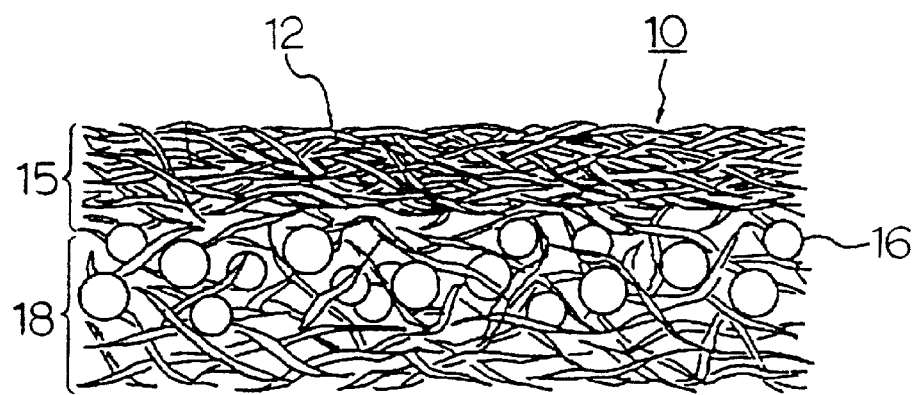
FIG. 1B is a schematic view illustrating the cross section of the first absorbent sheet of the present invention.

As shown in FIG. 1A and FIG. 1B, the first absorbent sheet 10 preferably comprises a fiber aggregate 15 and a fiber web 18. The fiber aggregate 15 has an absorbent surface 12, and does not contain a superabsorbent polymer 16 at the side of the absorbent surface 12.

The fiber web 18 comprises at least hydrophilic fibers.

As shown in FIG. 1A and FIG. 1B, the fiber aggregate 15 and the fiber web 18 forms a unitary body. The superabsorbent polymer 16 is distributed inside the fiber web 18.

Figure 24:
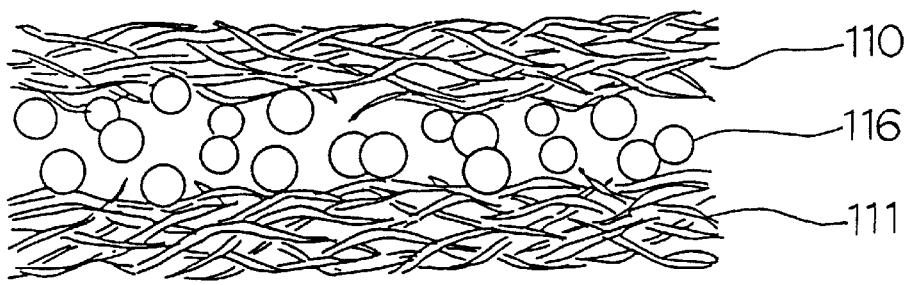
FIG. 24 is a schematic cross section of a conventional absorbent sheet.

A preferred embodiment of the first absorbent sheet 10 is characterized by comprising the fiber aggregate 15 and the fiber web 18 in a unitary body, with the superabsorbent polymer 16 contained therein. More specifically, the fiber aggregate 15 and the fiber web 18 are formed in a unitary body through mechanical entanglement of the fibers constituting the fiber aggregate 15 and the fibers constituting the fiber web 18, hydrogen bonding (and a strengthening assistant), heat fusion, and the like. Thus, the superabsorbent polymer 16 is securely fixed in the absorbent sheet 10 and prevented from falling off. The first absorbent sheet 10 exhibits improved permeability to liquid absorbed from the absorbent surface 12 and makes the liquid smoothly reach the superabsorbent polymer 16. Gel blocking of the superabsorbent polymer 16 having absorbed liquid is suppressed. Accordingly, the structure of the first absorbent sheet 10 is entirely different from a conventional absorbent sheet (FIG. 24) composed of a pair of sheets of absorbent paper having a superabsorbent polymer interposed therebetween. That is, the conventional absorbent sheet is a two-ply sheet, while the first absorbent sheet 10 is a single-ply sheet.

Such integration of the fiber aggregate 15 and the fiber web 18 is preferably achieved by overlaying in wet paper making as hereinafter described.

The fiber web 18 in the first absorbent sheet 10 is explained below.

The term "fiber web" as used herein means a web in which constituent fibers are not at all bound to each other or bound very slightly due to hydrogen bonding, mechanical entanglement, frictional force, etc. and have an extremely high degree of freedom while wet, and, after drying the constituent fibers are firmly bound to each other to take a sheet form.

It is important that the fiber web 18 should be in a wet state in order for the constituent fibers to have an extremely high degree of freedom before the superabsorbent polymer 16 is spread thereon. The superabsorbent polymer 16 spread over the fiber web 18 in a wet state is distributed from the surface to the inside of the fiber web 18 and fixed to the fiber web 18, i.e., three-dimensionally distributed in the fiber web 18. It is also important for the fiber web 18 to have such strength enough to prevent the superabsorbent polymer 16 from precipitating on the surface of the first absorbent sheet 10 after forming the fiber web 18 and the fiber aggregate 15 into a unitary body. It is preferable to this effect that the fiber web 18 has a wet strength of 50 g or more, still preferably 100 g or more, as measured according to JIS (Japanese Industrial Standard)-P-8113. In order to endow the fiber web 18 with such a wet strength, thermally fusible bonding fibers or a strengthening assistant are incorporated. It is preferable to further incorporate wood pulp or nonwood pulp which gives hydrogen bonding.

The fiber web 18 preferably has a basis weight of 10 to 200 g/m$^2$, more preferably 10 to 100 g/m$^2$, still preferably 20 to 80 g/m$^2$. If the basis weight is less than 10 g/m$^2$, there is a fear of the superabsorbent polymer 16's breaking out of the fiber web 18 and falling off on swelling. If the basis weight exceeds 200 g/m$^2$, the fiber web has too a high density, and the first absorbent sheet 10 becomes too hard, failing to fix the superabsorbent polymer 16 three-dimensionally, or resulting in deteriorated liquid permeability. Such a hard absorbent sheet may deteriorate the feel on use. Accordingly, the basis weight of the fiber web 18 preferably falls within the above range.

The above-mentioned fiber web contains at least hydrophilic fibers. The hydrophilic fibers are not particularly limited as long as the fibers have a hydrophilic surface and, while wet, are capable of forming a web in which the fibers have an extremely high degree of freedom from each other. While not limiting, examples of such hydrophilic fibers include natural cellulose fibers, such as wood pulp (e.g., soft wood kraft pulp, and hard wood kraft pulp) fibers, cotton pulp fibers and straw pulp fibers, regenerated cellulose fibers, such as rayon and cupra, synthetic hydrophilic fibers, such as polyvinyl alcohol fiber and polyacrylonitrile fiber; and synthetic fibers (e.g., polyethylene fiber, polypropylene fiber, and polyester fiber) having been rendered hydrophilic with a surface active agent. These hydrophilic fibers may be used either individually or as a combination thereof.

The hydrophilic fibers should be present in an amount of at least 30 parts by weight, preferably 50 parts by weight or more, per 100 parts by weight of the fiber web.

Of the above-enumerated hydrophilic fibers preferred are cellulose fibers. Cellulose fibers are preferred for having a stable hydrophilic surface and keeping hydrophilicity even after getting wet. Bulky cellulose fibers, such as natural cellulose fibers and regenerated cellulose fibers, are particularly preferred. From the economical viewpoint, wood pulp, particularly softwood kraft pulp is preferred. Use of the bulky cellulose fibers not only brings about further improvement on the dispersibility and the fixability of a superabsorbent polymer but makes it easier to control the drainage properties of the fiber web in wet paper making. Further, bulky cellulose fibers form a bulky fiber web having a high void content so that a superabsorbent polymer can be easily embedded, dispersed and fixed therein, and gel blocking of the superabsorbent polymer can be prevented. The average fiber length of the bulky cellulose fibers is not particularly limited but is preferably 1 to 20 mm in general. Also, in the present invention, fibers obtained by conducting hydrophilicity treatment on synthetic fibers such as PET, PE, PP, etc. are also preferably used as the bulky fibers.

The term "bulky fibers" herein means fibers having a three-dimensional structure such as a torsion structure, a crimped structure, a bent structure and/or branched structure, or alternatively, fibers having a thick fiber cross-section, for example, having a degree of fiber roughness of 0.3 mg/m or more.

The bulky cellulose fibers are preferably present in an amount of 30 parts by weight or more, still preferably 50 to 99 parts by weight, per 100 parts by weight of the fiber web.

A preferred example of the bulky cellulose fibers is cellulose fibers having a degree of fiber roughness of 0.3 mg/m or more. Such cellulose fibers are preferred because they are accumulated in a bulky state to easily form a bulky network structure in the fiber web and also because the formed fiber web has low resistance against liquid transfer to afford an increased rate of liquid permeation.

The term "degree of fiber roughness" as used herein means a measure indicative of fineness of fibers having non-uniform fineness. The degree of fiber roughness can be measured, for example, with a fiber roughness meter "FS-200" manufactured by Kajanni Electronics, LTD.

As stated above, the bulky cellulose fibers to be used preferably have a degree of fiber roughness of 0.3 mg/m or more, still preferably 0.3 to 2 mg/m, particularly preferably 0.32 to 1 mg/m.

Specific examples of the cellulose fibers having a degree of fiber roughness of 0.3 mg/m or more include softwood kraft pulp "Albacel" produced by Federal Paper Board Co. and "Indorayon" produced by PT Inti Indorayon Utama.

Another preferred example of the bulky cellulose fibers is cellulose fibers whose cross section has a degree of fiber roundness of 0.5 to 1, particularly 0.55 to 1. Cellulose fibers having a degree of fiber roundness in the fiber cross section of 0.5 to 1 have low resistance against liquid transfer to afford an increased rate of liquid permeation. The method of measuring a degree of the fiber roundness of the fiber cross section will be described later.

While wood pulp is preferably used as cellulose fibers as previously mentioned, wood pulp generally has a flat section owing to delignination treatment and mostly has a degree of fiber roundness in the fiber cross section of less than 0.5. The degree of fiber roundness in the fiber cross section of such wood pulp can be increased to 0.5 or more by, for example, mercerization to expand the cross section of wood pulp fibers.

Thus, mercerized pulp having a degree of fiber roundness in the fiber cross section of 0.5 to 1, which is obtained by mercerization of wood pulp, is also preferred bulky cellulose fibers. Specific examples of commercially available mercerized pulp which can be used in the present invention include "Filtranier" and "Porosanier" both produced by ITT Rayonier Inc.

Cellulose fibers having a degree of roughness of 0.3 mg/m or more and a degree of fiber roundness in the fiber cross section of 0.5 to 1 are particularly preferred for ease of formation of a bulky network structure and for further increasing the rate of liquid permeation.

A still another preferred example of the bulky cellulose fibers is crosslinked cellulose fibers obtained by intramolecular and/or intermolecular crosslinking of cellulose fibers. Crosslinked cellulose fibers are preferred for capability of maintaining a bulky structure while wet.

While not particularly limiting, crosslinking of cellulose fibers can be carried out by using a crosslinking agent. Useful crosslinking agents include N-methylol compounds, such as dimethylolethyleneurea and dimethyloldihydroxyethyleneurea; polycarboxylic acids, such as citric acid, tricarballylic acid, and butanetetracarboxylic acid; polyols, such as dimethylhydroxyethyleneurea; and polyglycidyl ether compounds. Polycarboxylic acids or polyglycidyl ether compounds which do not generate formalin harmful to human bodies on crosslinking are preferred.

The crosslinking agent is preferably used in an amount of 0.2 to 20 parts by weight per 100 parts by weight of cellulose fibers.

Crosslinking of cellulose fibers using the above-mentioned crosslinking agent can be carried out by, for example, immersing cellulose fibers in an aqueous solution of the crosslinking agent containing, if desired, a catalyst, dehydrating the impregnated cellulose fibers to have a prescribed add-on of the crosslinking agent aqueous solution, and heating the fibers to a crosslinking temperature; or spraying the crosslinking agent aqueous solution onto the cellulose fibers to give a prescribed add-on, followed by heating to the crosslinking temperature to induce crosslinking.

Commercially available crosslinked cellulose fibers include "High Bulk Additive" produced by Weyerhaeuser Paper Co.

In addition to the aforesaid preferred bulky cellulose fibers, bulky cellulose fibers obtained by intramolecular and/or intermolecular crosslinking of cellulose fibers, e.g., pulp, having a degree of fiber roughness of 0.3 mg/m or more according to the above-described methods are also preferred.

Bulky cellulose fibers obtained by intramolecular and/or intermolecular crosslinking of pulp having a degree of fiber roundness in the fiber cross section of 0.5 to 1 according to the above-described crosslinking methods are also preferred.

Bulky cellulose fibers obtained by intramolecular and/or intermolecular crosslinking of mercerized pulp having a degree of fiber roundness in the fiber cross section of 0.5 to 1 according to the above-described crosslinking methods are also preferred.

More preferred are bulky cellulose fibers obtained by crosslinking pulp having a degree of fiber roughness of 0.3 mg/m or more and a degree of fiber roundness in the fiber cross section of 0.5 to 1 according to the above-described crosslinking methods.

Still preferred are bulky cellulose fibers obtained by mercerizing pulp having a degree of fiber roughness of 0.3 mg/ml or more to increase the degree of fiber roundness to 0.5 to 1 and then crosslinking the mercerized pulp according to the above-described crosslinking methods.

In order to keep the structure stable even when the absorbent sheet according to the present invention get wet, it is necessary to endow the fiber web with a wet strength, in particular to incorporate thermally fusible bonding fibers or a strengthening assistant.

Also, in order to improve the strength of the absorbent sheet by strengthening the hydrogen bond between the cellulose fibers, it may be effective to incorporate ordinary cellulose fibers, that is, wood pulp or nonwood pulp or the like in place of the thermally fusible bonding fibers or the strengthening assistant. However, in order to obtain a sufficient wet strength of the absorbent sheet, it is preferred to incorporate the ordinary cellulose fibers in combination with the thermally fusible bonding fibers or the strengthening assistant.

The thermally fusible bonding fibers which can be used are fibers which are fused together upon heating. Examples of thermally fusible bonding fibers include polyolefin fibers, such as polyethylene, polypropylene, and polyvinyl alcohol, polyester fibers, polyethylene-polypropylene conjugate fibers, polyethylene-polyester conjugate fibers, low-melting polyester-polyester conjugate fibers, polyvinyl alcohol-polypropylene conjugate fibers having a hydrophilic surface, and polyvinyl alcohol-polyester conjugate fibers. The conjugate fibers may be either of a core/sheath type or a side-by-side type. These thermally fusible bonding fibers may be used either individually or as a mixture of two or more thereof. Polyvinyl alcohol fibers and polyester fibers are preferred for use in the present invention.

It is generally preferred that the thermally fusible bonding fibers have a fiber length of 2 to 60 mm and a fiber diameter of 0.1 to 3 denier, particularly 0.5 to 3 denier.

As stated above, the fiber web is added with a strengthening assistant, such as a polyamine-epichlorohydrin resin, dialdehyde starch, sponge or carboxymethyl cellulose. The strengthening assistant is added in an amount of 0.01 to 30 parts by weight, preferably 0.01 to 20 parts by weight, per 100 parts by weight of the fiber web.

When the thermally fusible bonding fibers are employed, the fiber web preferably comprises 30 to 99 parts by weight of the hydrophilic fibers and 1 to 50 parts by weight of the thermally fusible bonding fibers per 100 parts by weight of the fiber web. Still preferably, the fiber web comprises 50 to 97 parts by weight of the hydrophilic fibers and 3 to 30 parts by weight of the thermally fusible bonding fibers per 100 parts by weight of the fiber web.

The fiber web preferably comprises, for example, 1 to 10 parts by weight of vinylon fibers (polyvinyl alcohol fibers), and still preferably 2 to 5 parts by weight of vinylon fibers. The vinylon fibers are preferably those melting on exposure to moist heat.

Alternatively, the fiber web preferably comprises, for example, 1 to 30 parts by weight of the thermally fusible bonding fibers having a core/sheath structure, still preferably 5 to 20 parts by weight of the thermally fusible bonding fibers. Examples of the thermally fusible bonding fibers having a core/sheath structure include synthetic fibers composed of a sheath made of a polyethylene-vinyl acetate resin, a polyethylene resin or a modified polyester resin having a melting point of 70° to 150° C. or a moist heat-melting polyvinyl alcohol and a core made of a polypropylene resin or a polyester resin.

When the strengthening assistant is employed, it is preferable that the fiber web comprises 30 to 100 parts by weight of the hydrophilic fibers, 0 to 50 parts by weight of other fibers, and 0.01 to 30 parts by weight of the strengthening assistant per 100 parts by weight of the fiber web. It is still preferable that the fiber web comprises 50 to 100 parts by weight of the hydrophilic fibers, 0 to 20 parts by weight of other fibers, and 0.01 to 20 parts by weight of the strengthening assistant per 100 parts by weight of the fiber web.

The fiber web preferably comprises, for example, 30 to 99 parts by weight of the bulky cellulose fibers, 1 to 70 parts by weight of wood pulp or nonwood pulp, and 0.01 to 30 parts by weight of the strengthening assistant per 100 parts by weight of the fiber web. Still preferably, the fiber web comprises 50 to 95 parts by weight of the bulky cellulose fibers, 5 to 50 parts by weight of wood pulp or nonwood pulp, and 0.01 to 20 parts by weight of the strengthening assistant per 100 parts by weight of the fiber web.

The superabsorbent polymer 16 which is contained in the first absorbent sheet 10 will be explained below.

As shown in FIG. 1A, the superabsorbent polymer 16 is contained in the inside of the first absorbent sheet 10 and dispersed in the spaces formed among fibers constituting the first absorbent sheet 10. In more detail, as shown in FIG. 1B, the superabsorbent polymer 16 is contained primarily in the fiber web 18, i.e., contained primarily in the area from the interface between the fiber web 18 and the fiber aggregate 15 on the surface towards the fiber web 18, and is preferably dispersed in the spaces formed by the fibers constituting the fiber web 18. As a result, the superabsorbent polymer 16 is securely fixed in the first absorbent sheet, and gel blocking of the polymer is prevented. The term "the superabsorbent polymer is contained in the first absorbent sheet" as used herein does not mean to exclude existence of the superabsorbent polymer on the surface of the first absorbent sheet. Existence of a trace amount of a superabsorbent polymer on the surface of the first absorbent sheet is unavoidably accompanied by the preferred process for producing the first absorbent sheet hereinafter described, which is permitted in the present invention. Hence, the term means that most of the superabsorbent polymer exists in the inside of the first absorbent sheet.

The superabsorbent polymer 16 sticks to the hydrophilic fibers constituting the first absorbent sheet 10, preferably to the hydrophilic fibers constituting the fiber web 18, whereby fixation of the superabsorbent polymer 16 and gel blocking of the polymer are further suppressed. The superabsorbent polymer 16 mainly sticks to the hydrophilic fibers. However, it does not matter that the superabsorbent polymer 16 sticks to other fibers constituting the absorbent sheet, for example, thermally fusible bonding fibers. Further, not all the particles of the superabsorbent polymer 16 need to stick to the fibers.

It is preferable that at least 50% by weight, particularly 70% by weight or more, of the total superabsorbent polymer should stick to the fibers. The method for sticking the superabsorbent polymer 16 to the fibers will be described later In the case where a superabsorbent polymer agglomerate comprising secondary particles made of spherical primary particles is used, not all the primary particles need to stick to the fibers. Only if part of the secondary particles stick to the fibers, the superabsorbent polymer can be fixed to the fibers.

It is preferred for the superabsorbent polymer 16 not to be dispersed in the first absorbent sheet 10 in a layer but to be dispersed therein three-dimensionally as illustrated in FIG. 1A and FIG. 1B. In this case, a large quantity of the superabsorbent polymer can be dispersed. That is, in a conventional absorbent sheet with a superabsorbent polymer dispersed in a single layer (i.e., two-dimensionally), the amount of the superabsorbent polymer that can be spread is generally about 50 to 100 $g/m^2$ at the most. In the first absorbent sheet 10, to the contrary, since the superabsorbent polymer 16 can be dispersed three-dimensionally, the upper limit of the amount of the polymer to be spread can be raised to about 200 to 300 $g/m^2$, thus increasing the amount of spread the superabsorbent polymer 16 about 3 times as much as the permissive amount in a conventional absorbent sheet. As a result, the absorbent sheet 10 shows a marked increase in liquid absorption. Further, the absorption performance inherent in the superabsorbent polymer 16 can be manifested more effectively owing to the three-dimensionally dispersed system of the polymer. That is, with the amount of a superabsorbent polymer used being equal, the first absorbent sheet 10 exhibits improved absorption characteristics and may have its thickness extremely reduced as compared with the conventional one. Additionally, since the amount of the superabsorbent polymer to be spread may be increased, the absorbent sheet can be suitably used as an absorbent member of disposable diapers, etc. which require a high absorption capacity.

The superabsorbent polymer is spread in an amount of 5 to 300 $g/m^2$, preferably 10 to 250 $g/m^2$. Also, when the amount of the liquid to be absorbed is not too large, the amount of the superabsorbent polymer is preferably 20 to 70 mg per 1 $m^2$ of the absorbent sheet. If the amount is less than 5 $g/m^2$, the superabsorbent polymer lacks in absorptivity, failing to exercise sufficient functions. If it exceeds 300 $g/m^2$, the adhesive strength between the fiber web and the fiber aggregate is reduced, and the superabsorbent polymer is liable to fall off. It is therefore preferred that the amount of the superabsorbent polymer to be spread falls within the above range.

The superabsorbent polymer 16 is preferably such that it can absorb and retain 20 or more times as much liquid as its own weight and is capable of gelation on absorption. The shape of the superabsorbent polymer 16 is not particularly limited and the superabsorbent polymer 16 may be in the form of sphere, aggregate, cluster, powder or fiber. Preferably, the superabsorbent polymer is in the form of particle having a particle size of 1 to 1000 $\mu$m (still preferably 10 to 500 $\mu$m). Such superabsorbent polymers include starch, crosslinked carboxymethyl cellulose, polymers or copolymers of acrylic acid or an alkali metal salt thereof, polyacrylic acid and a salt thereof, and polyacrylate-grafted polymers. A sodium salt is referred as polyacrylate. Also useful for preference are copolymers prepared by copolymerizing acrylic acid with comonomers, such as maleic acid, itaconic acid, acrylamide, 2-acrylamido-2- methylpropanesulfonic acid, 2-(meth) acryloylethanesulfonic acid, 2-hydroxyethyl (meth)acrylate or styrenesulfonic acid, at a copolymerization ratio that would not impair the performances of superabsorbent polymers.

The fiber aggregate 15 having the absorbent surface 12 in the first absorbent sheet 10 will be explained below.

The term "absorbent surface" as used herein denotes the surface which is, in principle, the first to absorb liquid when the first absorbent sheet 10 absorbs liquid. In other words, in a preferred embodiment of the first absorbent sheet 10, liquid is primarily absorbed from the side of the fiber aggregate 15.

The fiber aggregate does not contain the superabsorbent polymer on the side of the absorbent surface thereof. The term "not contain the absorbent polymer" as used herein does not mean that no superabsorbent polymer is present at all on the side of the absorbent surface. Existence of a trace amount of a superabsorbent polymer on the absorbing side is unavoidably accompanied by the preferred process for producing the first absorbent sheet hereinafter described, which is permitted in the present invention. Hence, the term means that the absorbing side of the fiber aggregate contains substantially no superabsorbent polymer.

The fiber aggregate can be obtained through mechanical or physical entanglement of fibers, heat fusion, and the like, and includes paper and nonwoven fabric. Paper which can be used as fiber aggregate includes paper prepared by wet paper making or crepe paper thereof, that is, the superabsorbent polymer is not present. Nonwoven fabric to be used includes various kinds, such as nonwoven fabric prepared by carding, spun bonded fabric, spun lace fabric, consisting mainly of synthetic cellulose fibers, such as rayon or cuprammonium rayon, or natural cellulose fibers, such as cotton.

The fiber aggregate preferably contains hydrophilic fibers. The same hydrophilic fibers as used in the fiber web can be used. The hydrophilic fibers are preferably present in an amount of 30 parts by weight or more, still preferably 50 to 99 parts by weight, per 100 parts by weight of the fiber aggregate.

The fiber aggregate is preferably endowed with wet strength similarly to the fiber web; for the first absorbent sheet using the fiber aggregate endowed with wet strength can retain its shape stably after being wetted. The fiber aggregate preferably has a wet strength of 50 g or more, still preferably 100 g or more, as measured according to JIS-P-8113. In order to provide the fiber aggregate with such a wet strength, the above-mentioned thermally fusible bonding fibers, or the strengthening assistant are incorporated in the same manner as for the fiber web. Also, it is preferable to further incorporate wood pulp or nonwoven pulp which gives hydrogen bonding. The thermally fusible bonding fibers are preferably added in an amount of 1 to 50 parts by weight, still preferably 3 to 30 parts by weight, per 100 parts by weight of the fiber aggregate. The strengthening assistant is preferably used in an amount of 0.01 to 30 parts by weight, still preferably 0.02 to 20 parts by weight, per 100 parts by weight of the fiber aggregate.

It is particularly preferable that the fiber aggregate is comprised of the same formulation of the fibers and components constituting the above-mentioned fiber web.

It is also preferred that the fiber aggregate comprises nonwoven fabric, especially dry processed nonwoven fabric, for example nonwoven fabric obtained by carding. In particular, where the first absorbent sheet is applied to absorbent articles having the structure shown in FIGS. 16 and 17, in which the absorbent sheet also serves as a liquid permeable topsheet, use of nonwoven fabric made of synthetic fibers as a fiber aggregate provides an absorbent article with a further improved feel of dryness.

The fiber aggregate preferably has a basis weight of 10 to 200 $g/m^2$, still preferably 10 to 100 $g/m^2$. If the basis weight is less than 10 $g/m^2$, there is a fear of the swollen superabsorbent polymer's breaking out of the fiber aggregate to fall off. If it exceeds 200 $g/m^2$, the fiber aggregate has too high a density, making the absorbent sheet too hard. Accordingly, the basis weight of the fiber aggregate preferably falls within the above range.

The fiber aggregate may be previously prepared prior to the preparation of the fiber web, or it may be prepared simultaneously with the fiber web in the production of the first absorbent sheet.

In the first absorbent sheet, it is preferable that the fiber aggregate has a basis weight of 10 to 200 $g/m^2$; the amount of the spread superabsorbent polymer is 5 to 300 $g/m^2$; and the fiber web has a basis weight of 10 to 200 $g/m^2$. It is still preferable that the fiber aggregate has a basis weight of 10 to 100 $g/m^2$; the amount of the spread superabsorbent polymer is 5 to 200 $g/m^2$; and the fiber web has a basis weight of 10 to 100 $g/m^2$.

The first absorbent sheet preferably has a total basis weight of 21 to 500 $g/m^2$, more preferably 30 to 300 $g/m^2$, still preferably 50 to 200 $g/m^2$.

The first absorbent sheet has preferably a fiber density of 0.1 $g/cm^3$ or more, more preferably 0.1 to 0.4 $g/cm^3$, still preferably 0.1 to 0.2 $g/cm^3$. When the fiber density falls within the above range, gel blocking of the superabsorbent polymer is suppressed more efficiently. The fiber density falling within the above range can be easily obtained by using hydrophilic bulky cellulose fibers (in particular, bulky cellulose fibers).

A still preferred embodiment of the first absorbent sheet is an absorbent sheet which comprises a fiber structure comprising bulky hydrophilic cellulose fibers and thermally fusible bonding fibers or a strengthening assistant, and superabsorbent polymer particles, the superabsorbent polymer particles being not present on an absorbent surface of the absorbent sheet for absorbing the liquid but distributed inside and fixed to the fiber structure; and the absorbent sheet having a thickness of 0.3 to 1.5 mm, and the superabsorbent polymer being spread at an amount of 20 to 70 g per 1 $m^2$ of the absorbent sheet. Such an absorbent sheet has a very small thickness. Further, the sheet hardly increases its thickness even after absorbing liquid when the quantity of absorbed liquid is not too large. Accordingly, such an absorbent sheet, when used as an absorbent member in a sanitary napkin or the like, gives a feeling free from discomfort even after absorbing menstration blood when worn.

When the absorbent sheet according to the present invention is used as an absorbent member of a sanitary napkin, in the absorbent sheet, the superabsorbent polymer is preferably spread at an amount of 10 to 100 $g/m^2$, more preferably 20 to 70 $g/m^2$;

the basis weight of the fiber aggregate is preferably 10 to 80 $g/m^2$, more preferably 15 to 50 $g/m^2$;

the basis weight of the fiber web is preferably 10 to 80 $g/m^2$, more preferably 15 to 50 $g/m^2$; and the thickness of the absorbent sheet is preferably 0.3 to 1.5 mm.

On the other hand, when the absorbent sheet according to the present invention is used as an absorbent member for retaining a large amount of liquid, for example, an absorbent member of a disposable diaper in the absorbent sheet, the superabsorbent polymer is preferably spread at an amount of 50 to 300 g/m$^2$, more preferably 100 to 250 g/m$^2$;

the basis weight of the fiber aggregate is preferably 20 to 200 g/m$^2$, more preferably 20 to 100 g/m$^2$;

the basis weight of the fiber web is preferably 20 to 200 g/m$^2$, more preferably 20 to 100 g/m$^2$; and the thickness of the absorbent sheet is preferably 0.5 to 1.5 mm.

The thickness of the absorbent sheet can be made to be very small since the superabsorbent polymer is scattered in and adhered to the fibers and therefore the sheet exhibits an excellent absorbing efficiency. In particular, it is preferred to use bulky cellulose fibers since the scattered state of the absorbent polymer is further enhanced.

Additionally, the first absorbent sheet has a thickness of 0.3 to 1.5 mm, preferably 0.5 to 1.2 mm, under an applied load of 2.5 g/cm$^2$. Thus, the first absorbent sheet has a very small thickness. Besides, increase in the thickness of the sheet is small even after the sheet has absorbed liquid. This is because, when the sheet absorbs liquid, the absorbent polymer becomes large and the distances between the fibers increase, only to thereby increase the thickness of the absorbent sheet, and because the increase in thickness of the absorbent sheet is not caused by resilient forces of the fibers as disclosed in U.S. Pat. No. 4,605,402 and U.S. Pat. No. 5,021,050.

The thickness of the first absorbent sheet is measured after the fiber aggregate 15 and the fiber web 18 are formed into a unitary body. The thickness is smaller than the thickness obtained before they are formed into a unitary body. The thermally fusible bonding fibers or the strengthening assistant also greatly contribute to the forming the unitary body.

Also, in the first absorbent sheet, as described above, since the absorbent polymer is scattered in and fixed to the fibers, and the absorbent sheet exhibits an excellent absorption efficiency, the thickness of absorbent member can be made very small. In particular, bulky cellulose fibers are preferably used since the scattered state of the absorbent polymer is further enhanced. Since the superabsorbent polymer is in close contact with the fibers and the fiber aggregate 15 and the fiber web 18, the liquid is smoothly transferred to the superabsorbent polymer.

Figure 2:
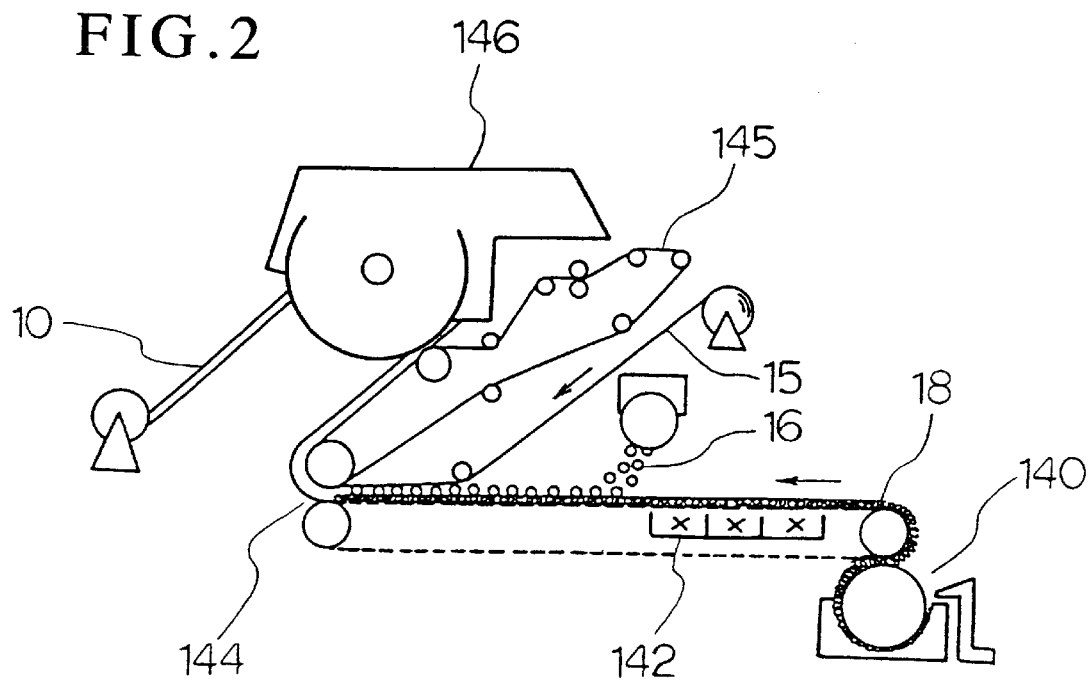
FIG. 2 is a schematic view illustrating an apparatus which can be preferably used for producing the first absorbent sheet of the present invention.

A process which can be preferably used for the production of the first absorbent sheet will be described below by referring to the drawings. FIG. 2 is a schematic view illustrating an apparatus which can be preferably used for the production of the first absorbent sheet of the present invention.

This process is one for preparing an absorbent sheet comprising at least hydrophilic fibers and thermally fusible bonding fibers or a strengthening assistant and a superabsorbent polymer, and is characterized by comprising the steps of spreading the superabsorbent polymer on a wet fiber web which is prepared by a wet process from an aqueous slurry comprising at least hydrophilic fibers and the thermally bonding fibers or the strengthening assistant;

overlaying thereon a fiber aggregate comprising the hydrophilic fibers and the thermally fusible bonding fibers or the strengthening assistant; and drying a combination of the fiber web and the fiber aggregate to form a unitary body thereof.

The process makes it possible to readily scatter the superabsorbent polymer in the inside of the absorbent sheet while keeping the polymer from being present on the absorbent surface of the absorbent sheet for absorbing liquid. Also, the process make it possible to readily adhere and fix the polymer to the hydrophilic fibers constituting the absorbent sheet. Further, it make it possible to easily make the thickness of the absorbent sheet very small, that is, 0.3 to 1.5 mm.

First of all, a fiber web comprising at least hydrophilic fibers is formed. The method for forming the fiber web is not particularly restricted. Either a dry paper making process or a wet paper making process can be used, with the latter being preferred. As hereinafter described, the fiber web on which the superabsorbent polymer is spread must be wet, and the fibers of the web should have an extremely high degree of freedom. A wet paper making method provides a fiber web as wet, saving labor for separately wetting a fiber web. Further, fibers of a fiber web obtained by a wet process are not sufficiently bound to each other before they are dried. A superabsorbent polymer spread over such a wet fiber web is readily embedded three-dimensionally in the spaces formed among fibers, thereby a large amount of the superabsorbent polymer can be spread.

In carrying out wet paper making for preparing a fiber web, fiber web-forming fibers and components, preferably the above-described hydrophilic fibers, and the thermally fusible bonding fibers, or the strengthening assistant, are dispersed in water in prescribed concentrations to prepare a slurry. The concentrations of the hydrophilic fibers, and thermally fusible bonding fibers, or the strengthening assistant in the slurry are selected from those used in general wet paper making. The proportions of the hydrophilic fibers, and thermally fusible bonding fibers, a strengthening assistant or the like in the slurry are selected so that the resulting fiber web may have the above-mentioned composition.

Over the thus obtained fiber web is spread the aforesaid superabsorbent polymer. The fiber web preferably has such wetness as containing about 20 to 500 parts by weight, still preferably 50 to 300 parts by weight, of water per 100 parts by weight of the fiber web on a dry basis. If the water content is less than 20 parts by weight, the spread superabsorbent polymer cannot absorb sufficient water to swell and to acquire stickiness, and therefore fixing of the superabsorbent polymer tends to be insufficient. If the water content exceeds 500 parts by weight, the superabsorbent polymer absorbs excessive water and tends to fail to dry up in the drying step hereinafter described. Accordingly, the water content of the wet fiber web preferably falls within the above range.

The superabsorbent polymer is spread over a wet fiber web, whereby the superabsorbent polymer absorbs water, assumes stickiness, and is embedded into the fibers constituting the fiber web, and adhered and fixed to the fibers. Since the fibers constituting the wet fiber web are not yet bound to each other and have freedom, the superabsorbent polymer can be dispersed therein three-dimensionally. Accordingly, a larger amount of a superabsorbent polymer can be fixed stably than in conventional absorbent sheets. The superabsorbent polymer may be spread uniformly all over the wet fiber web or, if desired, may be spread partly in stripes parallel at certain intervals in the longitudinal direction or may be spread intermittently in the longitudinal direction.

Then, the above-described fiber aggregate is overlaid on the fiber web with the superabsorbent polymer on. Since the fibers in the fiber web still have freedom at the time, the superabsorbent polymer are embedded deeper into the fiber web, and the fibers of the fiber web and those of the fiber aggregate are easily entangled with each other.

The laminate of the fiber web and the fiber aggregate is subsequently dried, whereupon the fibers are entangled with each other, the actions of hydrogen bonds and heat fusion are added thereto, and the fiber web and the fiber aggregate are formed into a unitary body to provide the first absorbent sheet. The drying temperature preferably ranges from 100° to 180° C., still preferably from 105° to 150° C., while varying depending on the kind of the fibers used. Through this step, the fiber web and the fiber aggregate are formed into a unitary body, and the fibers constituting the fiber web are bound to each other into a sheet. The drying means is not particularly limited and includes, for example, a Yankee dryer and an air-through dryer.

In a particularly preferred embodiment, the first absorbent sheet is produced at a single step in an in-line system using a wet paper making machine. As shown in FIG. 2, the fiber web 18 is formed in a forming part 140 of a wet paper making machine and dehydrated in a suction dehydration step 142. The dehydration is carried out to the extent that a water content is 20 to 500 parts by weight per 100 parts by weight of the dry fiber web. The superabsorbent polymer 16 is spread over the fiber web 18 immediately before a press part 144, and the fiber aggregate 15 is overlaid thereon concurrently. The resulting laminate is carried on a conveyor 145 to a dryer 146, where the laminate is dried and formed into a unitary body. The first absorbent sheet 10 can thus be produced at a high speed with ease.

Usual paper making machines, such as a wire paper making machine and a cylinder paper making machine, can be used in the in-line system. As for other steps than the above, steps generally used in paper making can be adopted appropriately.

While production of the first absorbent sheet of the present invention has been described with reference to its preferred embodiments, the process for producing the first absorbent sheet is by no means limited thereto.

Figure 3:
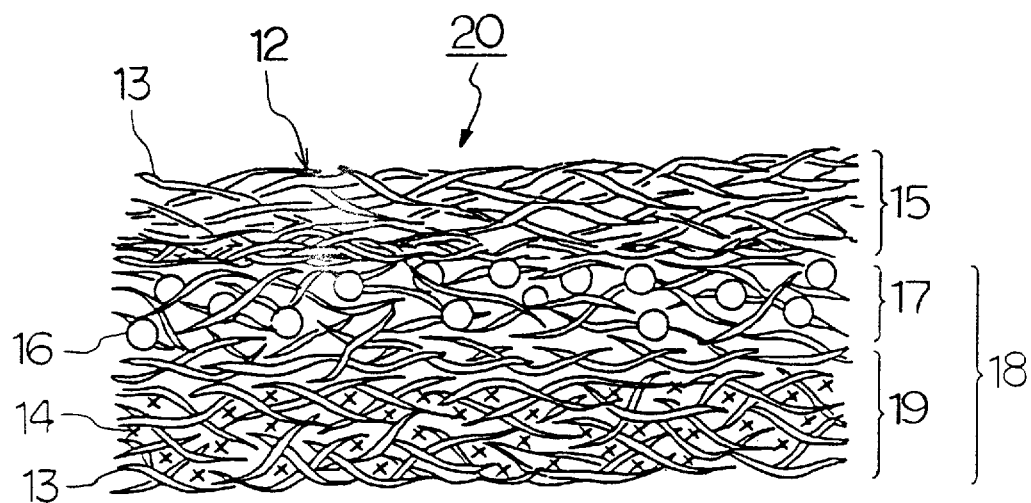
FIG. 3 is a schematic view illustrating the cross section of the second absorbent sheet of the present invention, which corresponds to FIG. 1B.

The second and third absorbent sheets according to the present invention will be described in detail by referring to the drawings. FIG. 3 is a schematic cross section of the second absorbent sheet, and FIG. 4 is a schematic cross section of the third absorbent sheet, FIGS. 3 and 4 corresponding to FIG. 1B.

Figure 4:
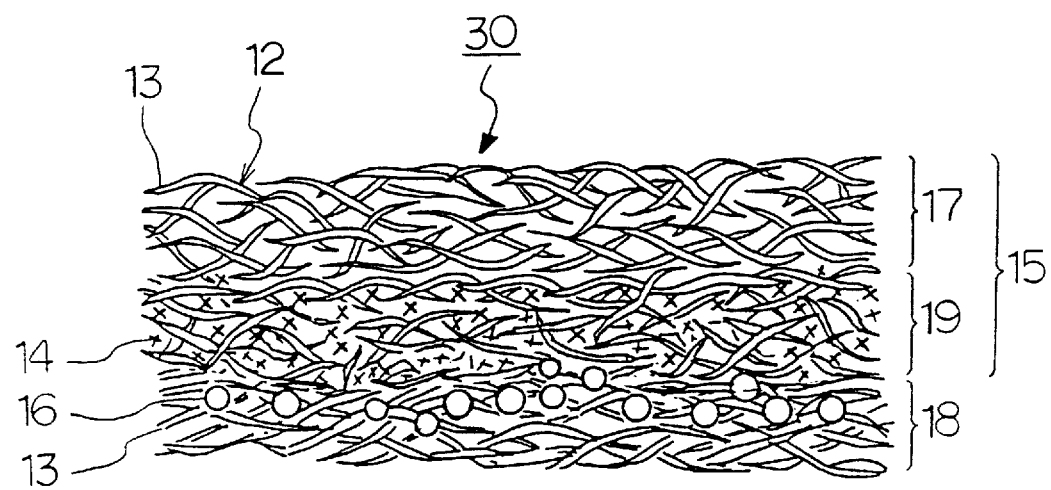
FIG. 4 is a schematic view illustrating the cross section of the third absorbent sheet of the present invention, which corresponds to FIG. 1B.

While not giving particulars, the same explanation given to FIG. 1A and FIG. 1B applies to the corresponding parts of FIGS. 3 and 4. The same reference numerals as used in FIG. 1A and FIG. 1B are also used for the same members in FIGS. 3 and 4.

First of all, the second absorbent sheet will be described. As shown in FIG. 3, the second absorbent sheet 20 is an absorbent sheet containing at least a superabsorbent polymer, bulky cellulose fibers, and hydrophilic fine fibers. The second absorbent sheet 20 comprises the fiber aggregate 15 and the fiber web 18. The fiber aggregate 15 has the absorbent surface 12 and does not contain a superabsorbent polymer at the side of the absorbent surface 12. The fiber aggregate 15 predominantly comprises bulky cellulose fibers 13 having a degree of fiber roughness of 0.3 mg/m or more.

As shown in FIG. 3, the fiber web 18 comprises a permeable layer 17 predominantly comprising the bulky cellulose fibers 13 having a degree of fiber roughness of 0.3 mg/m or more and a diffusing layer 19 being located adjacent to the permeable layer and comprising the bulky cellulose fibers 13 having a degree of fiber roughness of 0.3 mg/m or more and hydrophilic fine fibers 14. The fiber web 18 is located adjacent to the fiber aggregate 15 at the permeable layer 17 thereof.

As shown in FIG. 3, the fiber aggregate 15 and the fiber web 18 are in a unitary body. The superabsorbent polymer 16 is contained in the second absorbent sheet 20, while sticking to the fibers constituting the second absorbent sheet 20.

Thus, the second absorbent sheet 20 is characterized by comprising the fiber aggregate 15 and the fiber web 18 in an ultrathin unitary body, with the superabsorbent polymer 16 contained therein. Such an ultrathin unitary structure of the second absorbent sheet 20 is the same as in the first absorbent sheet. While not going into details, the explanation made for the unitary structure of the first absorbent sheet applies appropriately to the second absorbent sheet.

The permeable layer 17 and the diffusing layer 19 which constitute the fiber web 18 will be each described.

First, the permeable layer 17 will be described.

The permeable layer 17 predominantly comprises bulky cellulose fibers having a degree of fiber roughness of 0.3 mg/m or more. The permeable layer 17 having such a structure is capable of stably securing spaces where liquid is temporarily absorbed and is allowed to quickly pass therethrough.

The permeable layer 17 preferably has a thickness of 0.1 to 1.5 mm. If the thickness is less than 0.1 mm, the liquid absorbing space for temporary absorption would be small only to provide insufficient absorption performance. If the thickness exceeds 1.5 mm, absorbed liquid is hardly transferred to the diffusing layer 19. Accordingly, the thickness preferably falls within the above range. A still preferred thickness of the permeable layer 17 is 0.2 to 0.7 mm.

It is particularly preferred for the permeable layer 17 to give liquid a quick passage therethrough. More specifically, a passage of 10 g of a 85 wt % aqueous solution of glycerin is preferably accomplished within 50 seconds, still preferably 5 to 40 seconds. A permeable layer requiring more than 50 seconds for that passage makes it difficult for liquid to be transferred rapidly, and the liquid tends to be retained within the permeable layer 17 for a long time. The above-described passage time is measured in accordance with the following procedure with the apparatus shown in FIG. 25.

Figure 25:
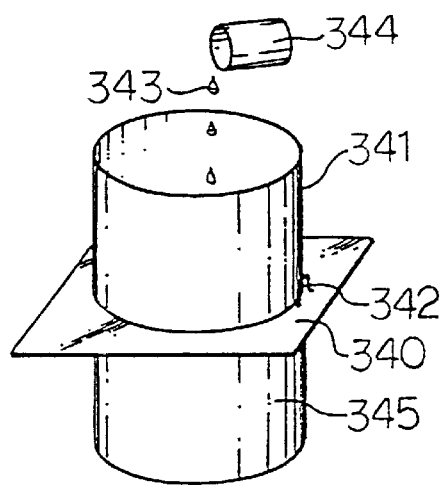
FIG. 25 is a schematic view showing an apparatus for measuring the passage time of an aqueous glycerol solution.

First, the absorbent paper is cut into test pieces 340 having a size of 50 mm×50 mm as shown in FIG. 25. Thereafter, as illustrated in FIG. 25, the test piece 340 is sandwiched and fixed between the ends of upper and lower glass pipes 341, 345 having an inner diameter of 35 mm. At this time, the test piece 340 is fixed from both sides with clips (not shown) via a silicone rubber 342 such that no liquid would leak laterally during the measurement. As the test liquid, 10 g of an 85% by weight aqueous glycerol solution 343 is taken into a 10-ml beaker 344 and gently poured from the beaker 344 into the upper glass pipe 341. After the 85% by weight aqueous glycerol solution 343 has been poured into the upper glass pipe 341, the time taken for a portion of the surface of the test piece 340, which portion corresponds to at least 50% of the opening area of the glass pipe 341, to appear is measured. The time thus measured is taken as the passage time.

The test liquid (i.e., the 85% by weight aqueous glycerol solution) is prepared in the manner described below.

After mixing 85 g of glycerol (supplied by Wako Chemical Industries, Ltd.) with 15 g of ion-exchanged water, 0.01 g of Blue No. 1 for food (colorant supplied by Tokyo Kasei Kogyo K.K.) is added to the resulting mixture in order to color the test liquid in blue.

The permeable layer 17 preferably contains 50 to 98 parts by weight of bulky cellulose fibers having a degree of fiber roughness of 0.3 mg/m or more and 2 to 50 parts by weight of thermally fusible bonding fibers. If the proportion of the bulky cellulose fibers is less than 50 parts by weight, or if that of the thermally fusible bonding fibers exceeds 50 parts by weight, the permeable layer 17 tends to have reduced liquid permeability. If the proportion of the bulky cellulose fibers is more than 98 parts by weight, or if that of the thermally fusible bonding fibers is less than 2 parts by weight, sheeting of the permeable layer 17 tends to be difficult. Accordingly, the above ratio is preferred. Still preferably, the permeable layer 17 comprises 70 to 98 parts by weight of bulky cellulose fibers and 2 to 30 parts by weight of thermally fusible bonding fibers.

The diffusing layer 19 which constitutes the fiber web in combination with the permeable layer 17 is described below.

The diffusing layer 19 comprises bulky cellulose fibers having a degree of fiber roughness of 0.3 mg/m or more and hydrophilic fine fibers. The diffusing layer 19 having such a structure is capable of quickly diffusing liquid over a wide area. In particular, even when a large quantity of liquid is absorbed at a time, the diffusing layer 19 absorbs the liquid rapidly and sufficiently.

The diffusing layer 19 preferably has a thickness of 0.2 to 2.0 mm. If the thickness is less than 0.2 mm, the spaces for diffusing liquid tends to be too small to exhibit sufficient diffusing performance. If the thickness exceeds 2.0 mm, liquid is interfered with smooth diffusion. Accordingly, the thickness preferably falls within the above range. A still preferred thickness of the diffusing layer 19 is 0.2 to 1.5 mm.

It is particularly preferred that the diffusing layer 19 quickly diffuses liquid over a wide area. To this effect, the diffusing layer 19 preferably has an absorption height after 1 minute absorption of physiological saline by Klemm's Method of 50 mm or more, and an absorption height after 10 minutes absorption of physiological saline by Klemm's Method of 100 mm or more. At the absorption height by Klemm's Method is less than these levels, the diffusing layer 19 has poor liquid diffusibility. A still preferred absorption height after 1 minute absorption of physiological saline by Klemm's Method is 60 to 120 mm and an absorption height after 10 minutes absorption of physiological saline by Klemm's Method is 120 to 300 mm. The absorption height by Klemm's Method is measured in accordance with the following procedure with the apparatus shown in FIG. 26.

Figure 26:
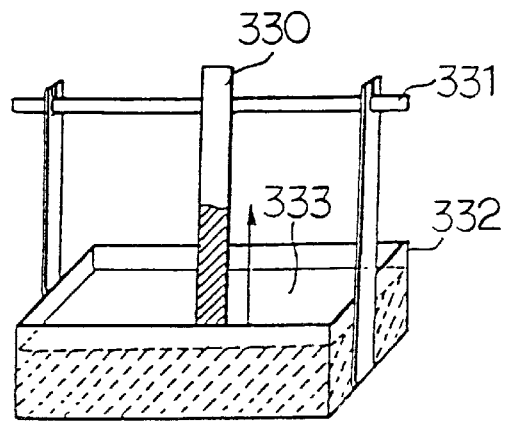
FIG. 26 is a schematic view showing an apparatus for measuring an absorption height of physiological saline by Klemm's Method.

First, the absorbent paper is cut into test pieces 330 having a size of 300 mm×20 mm as shown in FIG. 26. Thereafter, as illustrated in FIG. 26, the test piece 330 is hung from a support 331, and the upper and lower ends of the test piece 330 are fixed such that it might not be slack. Also, a physiological saline 333 serving as a test liquid is introduced to a depth of 40 mm in a rectangular vessel 332 having a size of 300×100×50 mm (length×width×depth), and the test piece 330 is immersed in the physiological saline 333.

The height of the test liquid, which has been absorbed by the test piece 330, the height being taken from the surface of the test liquid, is measured 1 minute after the immersion of the test piece 330. Also, the height of the test liquid, which has been absorbed by the test piece 330, the height being taken from the surface of the test liquid, is measured 10 minutes after the immersion of the test piece 30.

For each of the absorption heights by Klemm's Method after 1 minute and after 10 minutes, the aforesaid test is repeated by using 10 test pieces, and a mean value of the 10 measured values is calculated. In this manner, the absorption height by Klemm's Method $h_1$ after 1 minute and the absorption height by Klemm's Method $h_{10}$ after 10 minutes are obtained.

The diffusing layer 19 preferably comprises 20 to 80 parts by weight of bulky cellulose having a degree of fiber roughness of 0.3 mg/m or more, 20 to 80 parts by weight of hydrophilic fine fibers, and 0 to 30 parts by weight of thermally fusible bonding fibers. If the proportion of the bulky cellulose fibers is less than 20 parts by weight or if that of the hydrophilic fine fibers exceeds 80 parts by weight, a strong tension is exerted among fibers during preparation of the diffusing layer 19, especially in a wet process, to thereby reduce the liquid absorbing spaces, so that the substantial spaces for liquid diffusion tend to be reduced. If the proportion of the bulky cellulose fibers exceeds 80 parts by weight, or if that of the hydrophilic fine fibers is less than 20 parts by weight, the distance among fibers tends to become too large to exhibit sufficient liquid diffusion. Accordingly, the ratio of these materials preferably falls within the above range.

Incorporation of up to 30 parts by weight of the thermally fusible bonding fibers is preferable to ensure stabilization of the fiber spaces while wet. It is particularly preferred that the diffusing layer 19 comprises 30 to 70 parts by weight of the bulky cellulose fibers having a degree of fiber roughness of 0.3 mg/m or more, 30 to 70 parts by weight of the hydrophilic fine fibers, and 0 to 20 parts by weight of the thermally fusible bonding fibers.

The descriptions given to the bulky cellulose fibers and the thermally fusible bonding fibers which constitute the permeable layer 17 appropriately apply to those fibers to be used in the diffusing layer 19. The bulky cellulose fibers and the thermally fusible bonding fibers used in the diffusing layer 19 and those used in permeable layer may be of the same or different kinds, but are preferably of the same kinds.

The hydrophilic fine fibers which constitutes the diffusing layer 19 include those having a hydrophilic surface and a large surface area. More specifically, it is preferable to use hydrophilic fine fibers having a degree of fiber roughness of less than 0.3 mg/m, still preferably less than 0.2 mg/m, particularly preferably 0.01 to 0.2 mg/m, and a degree of fiber roundness in the fiber cross section of less than 0.5, still preferably 0.1 to 0.4. The average fiber length of the hydrophilic fine fibers is not particularly limited but, in general, preferably ranges from 0.02 to 0.5 mm.

Examples of the hydrophilic fine fibers include cellulose fibers, such as wood pulp, cotton, and rayon; and synthetic fibers having a hydrophilic group, such as acrylonitrile and polyvinyl alcohol. Preferred of them is wood pulp; for it is inexpensive, and its surface area can be varied by controlling beating conditions. Examples of the wood pulp includes fine fibers obtained by finely beating softwood kraft pulp, e.g., "Skeena Prime" produced by Skeena Cellulose Co., hardwood kraft pulp "Prime Albert Aspen Hardwood" produced by Weyerhaeuser Paper Co., and straw pulp. These hydrophilic fine fibers may be used either individually or as a mixture of two or more thereof.

The superabsorbent polymer 16 which is contained in the second absorbent sheet 20 is then described.

As shown in FIG. 3, the superabsorbent polymer 16 is contained in the inside of the second absorbent sheet 20. It is dispersed in the spaces formed among fibers constituting the second absorbent sheet 20. In more detail, as shown in FIG. 3, the superabsorbent polymer 16 is mostly contained in the inside of the fiber web 18, i.e., contained primarily in the area from the interface between the fiber web 18 and the fiber aggregate 15 to the inside of the fiber web 18, especially in the permeable layer 17, and is preferably dispersed in the spaces formed among fibers constituting the fiber web 18.

The superabsorbent polymer 16 sticks to the fibers constituting the second absorbent sheet 20, preferably to the fibers constituting the fiber web 18, still preferably to the fibers constituting the permeable layer 17.

As for other points concerning the superabsorbent polymer, for example, the dispersed state, the kind, the amount to be spread, and various physical properties, the corresponding explanation made for the superabsorbent polymer used in the first absorbent sheet is appropriately applied.

There is a diffusion gradient in the second absorbent sheet 20 having the above-mentioned unitary structure. In detail, the absorbent surface 12 of the second absorbent sheet 20 has high liquid permeability so that little liquid remains on the absorbent surface 12. Passing through the permeable layer 17, the absorbed liquid rapidly reaches the superabsorbent polymer 16 and is diffused throughout the entire area of the second absorbent sheet 20, preferentially in the diffusing layer 19 having high diffusing properties. Thus, since the second absorbent sheet 20 combines a permeation function, a diffusion function, and a fixing function in its single structure, it can fix liquid in the superabsorbent polymer 16 quickly and securely.

The third absorbent sheet according to the present invention will be described below.

As shown in FIG. 4, third absorbent sheet 30 comprises at least a superabsorbent polymer, bulky cellulose fibers, and hydrophilic fine fibers. The third absorbent sheet 30 comprises the fiber aggregate 15 and the fiber web 18. The fiber aggregate 15 has the absorbent surface 12 and does not contain the superabsorbent polymer on the side of the absorbent surface 12. The fiber aggregate 15 comprises the permeable layer 17 mainly comprising the bulky cellulose fibers 13 having a degree of fiber roughness of 0.3 mg/m or more and the diffusing layer 19 being located adjacent to the permeable layer 17 and comprising the bulky cellulose fibers 13 having a degree of fiber roughness of 0.3 mg/m or more and the hydrophilic fine fibers 14.

As shown in FIG. 4, the fiber web 18 predominantly comprising bulky cellulose fibers having a degree of fiber roughness of 0.3 mg/m or more. The fiber web 18 is located adjacent to the diffusing layer 19 of the fiber aggregate 15.

As shown in FIG. 4, the fiber aggregate 15 and the fiber web 18 are in a unitary body. The superabsorbent polymer 16 is contained in third absorbent sheet 30 and sticks to the fibers constituting third absorbent sheet 30.

Similarly to the first absorbent sheet 10, the third absorbent sheet 30 is characterized by its ultrathin unitary structure which comprises the fiber aggregate 15 and the fiber web 18 and contains the superabsorbent polymer 16 in the inside thereof. Such ultrathin unitary structure is the same as in the first absorbent sheet, and the explanation given to the unitary structure of the first absorbent sheet also applies to the third absorbent sheet.

The superabsorbent polymer 16 contained in the third absorbent sheet 30 is described below.

Similarly to the first absorbent sheet, the superabsorbent polymer 16 is contained in the third absorbent sheet 30 as dispersed in the spaces formed among fibers constituting third absorbent sheet 30. In more detail, as shown in FIG. 4, the superabsorbent polymer 16 is contained primarily in the fiber web 18, i.e., contained primarily in the area from the interface between the fiber web 18 and the fiber aggregate 15 to the inside of the fiber web 18, and is preferably dispersed in the spaces formed by the fibers constituting the fiber web 18.

The superabsorbent polymer 16 sticks to the fibers constituting third absorbent sheet 30, preferably to the fibers constituting the fiber web 18.

The fiber aggregate 15 having the absorbent surface 12 in the third absorbent sheet is described below.

The fiber aggregate 15 has an absorbent surface 12, and the fiber aggregate does not contain the superabsorbent polymer at the side of the absorbent surface 12.

The fiber aggregate 15 comprises a permeable layer 17 predominantly comprising bulky cellulose fibers having a degree of fiber roughness of 0.3 mg/m or more and the diffusing layer 19, which adjoins the permeable layer 17, comprising bulky cellulose fibers having a degree of fiber roughness of 0.3 mg/m or more and hydrophilic fine fibers. The surface of the permeable layer 17 corresponds to the absorbent surface 12.

The diffusing layer 19 of the fiber aggregate 15 adjoins the fiber web 18 as shown in FIG. 4.

For the details of the permeable layer 17 and the diffusing layer 19 which compose the fiber aggregate 15, the corresponding explanation given to these layers of the second absorbent sheet 20 applies appropriately.

For details of the bulky cellulose fibers and hydrophilic fibers constituting the permeable layer 17 and the diffusing layer 19, the corresponding explanation given to these fibers of the second absorbent sheet 20 applies appropriately.

Similarly to the second absorbent sheet 20, the third absorbent sheet 30 exhibits gradation in liquid diffusion from the absorbent surface 12 toward the inside. In more detail, the vicinities of the absorbent surface 12, particularly the permeable layer 17 of third absorbent sheet 30 have high liquid permeability so that liquid is rapidly transferred to the diffusing layer 19. In the vicinities of the superabsorbent polymer 16, the liquid is diffused throughout the entire area of the third absorbent sheet 30 and retained by the superabsorbent polymer 16. Thus, similarly to the second absorbent sheet, third absorbent sheet 30 combines a permeation function, a diffusion function, and a fixing function in its single structure, it can fix liquid in the superabsorbent polymer 16 quickly and securely.

Figure 5:
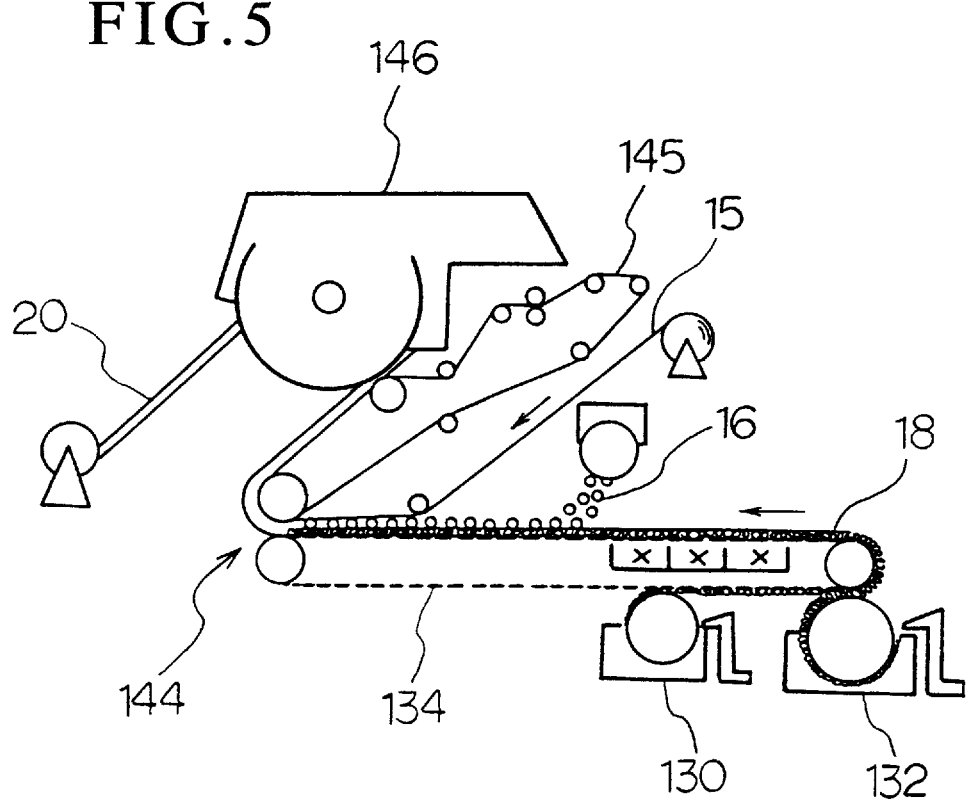
FIG. 5 is a schematic view illustrating an apparatus which can be preferably used for producing the second absorbent sheet of the present invention.

A process which can be preferably used for the production of the second and third absorbent sheets will be described below by referring to the drawings. FIG. 5 is a schematic view illustrating an apparatus which can be preferably used for the production of the second absorbent sheet of the present invention, which corresponds to FIG. 2. While not particularly mentioned, the explanation given to FIG. 2 applies to the corresponding members of FIG. 5. The same reference numerals as used in FIG. 2 are used for the same members of FIG. 5.

The process for producing the second absorbent sheet comprises the steps of:

spreading a superabsorbent polymer over a permeable layer in a wet fiber web, which comprises the permeable layer predominantly comprising bulky cellulose fibers having a degree of fiber roughness of 0.3 mg/m or more and a diffusing layer being located adjacent to the permeable layer and comprising bulky cellulose fibers having a degree of fiber roughness of 0.3 mg/m or more and hydrophilic fine fibers;

overlaying on the fiber web a fiber aggregate which predominantly comprises bulky cellulose fibers having a degree of fiber roughness of 0.3 mg/m or more; and drying a combination of the fiber web and the fiber aggregate and forming a unitary body thereof.

Going into details, the combined formation of the permeable layer and the diffusing layer can be carried out as follows. As shown in FIG. 5, the diffusing layer 19 is formed in the first forming part 130 to which a first aqueous slurry of bulky cellulose fibers having a degree of fiber roughness of 0.3 mg/m or more and hydrophilic fine fibers, etc. is supplied. A permeable layer 17 is then formed on the diffusing layer 19 in the second forming part 132 to which a second aqueous slurry of bulky cellulose fibers having a degree of fiber roughness of 0.3 mg/m or more, etc. is supplied, whereby the fiber web 18 comprising the diffusing layer 19 and the permeable layer 17 is formed on the wire 134. The concentrations of the fibrous material in the first and second slurries are selected from the ranges generally used in wet paper making. The proportions of the fibrous materials in each slurry are decided so that the resulting diffusing layer and permeable layer may have the above-described compositions.

The steps following the formation of the fiber web 18 are the same as those in the preferred process for producing the first absorbent sheet. The corresponding explanation made for the preferred process for producing the first absorbent sheet applies thereto.

There is thus obtained the second absorbent sheet according to the present invention.

A process which can preferably be used for the production of the third absorbent sheet comprises the steps of:

spreading a superabsorbent polymer over a wet fiber web which predominantly comprises bulky cellulose fibers having a degree of fiber roughness of 0.3 mg/m or more;

overlaying on the fiber web a fiber aggregate, which comprises a permeable layer predominantly comprising bulky cellulose fibers having a degree of fiber roughness of 0.3 mg/m or more and a diffusing layer being located adjacent to the permeable layer and comprising bulky cellulose fibers having a degree of fiber roughness of 0.3 mg/m or more and hydrophilic fine fibers, in such a manner that the fiber web is in contact with the diffusing layer; and drying a combination of the fiber web and the fiber aggregate and forming a unitary body thereof.

The preferred process for producing the third absorbent sheet is substantially the same as the preferred process for producing the first absorbent sheet, and the third absorbent sheet can be produced by using the apparatus shown in FIG. 2, which is preferably used for the production of the first absorbent sheet. The difference consists in that fiber aggregate comprising permeable layer predominantly comprising bulky cellulose fibers and the diffusing layer 19 being located adjacent to the permeable layer and comprising bulky cellulose fibers and hydrophilic fine fibers is overlaid on the surface of the fiber web 18, on which the superabsorbent polymer 16 has been spread, in such a manner that the fiber web 18 is brought into contact with the diffusing layer 19. In this case, the fiber aggregate 15 previously prepared by combined paper making may be unwound, or it may be prepared concurrently with the preparation of the fiber web 18.

Figure 6:
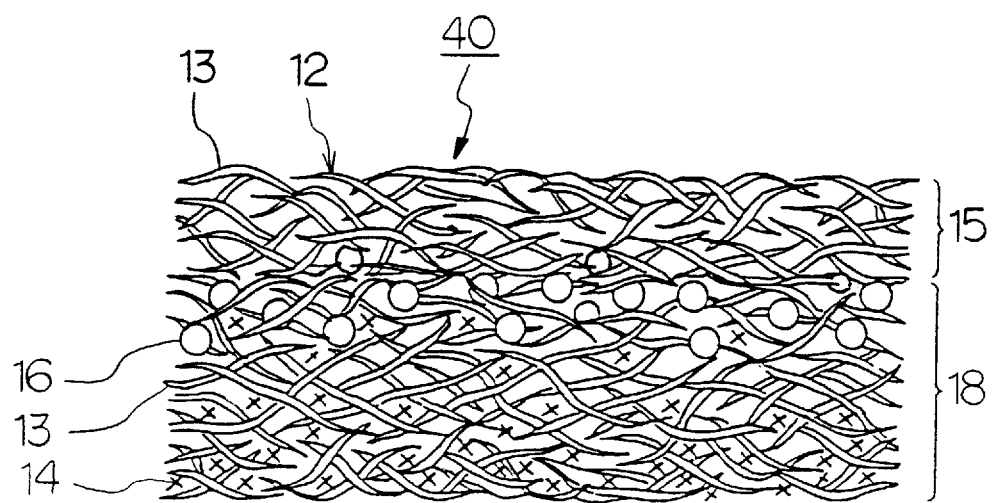
FIG. 6 is a schematic view illustrating the cross section of the fourth absorbent sheet of the present invention, which corresponds to FIG. 1B.

The fourth and fifth absorbent sheets according to the present invention will be described in detail by referring to the drawings. FIG. 6 is a schematic cross section of the fourth absorbent sheet, and FIG. 7 is a schematic cross section of the fifth absorbent sheet, FIGS. 6 and 7 corresponding to FIG. 1B.

Figure 7:
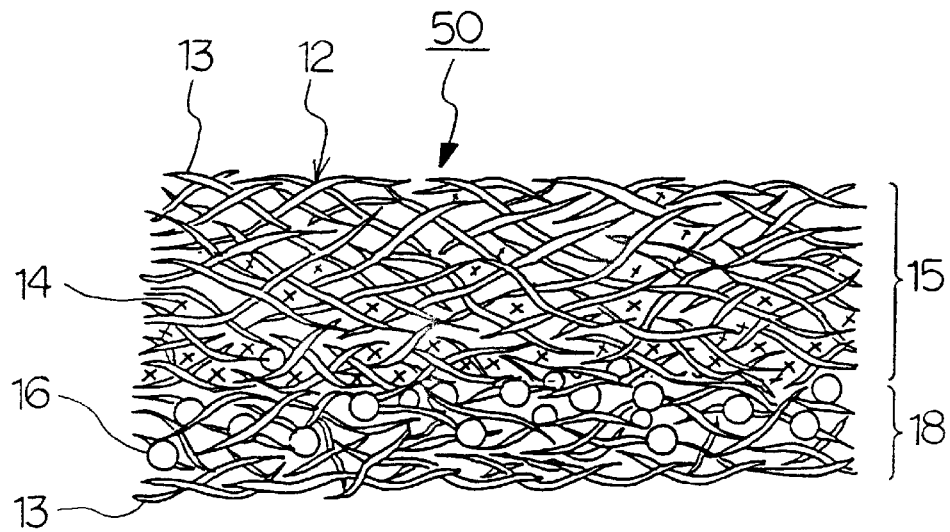
FIG. 7 is a schematic view illustrating the cross section of the fifth absorbent sheet of the present invention, which corresponds to FIG. 1B.

While not giving particulars, the same explanation as given to FIG. 1A and FIG. 1B applies to the corresponding points of FIGS. 6 and 7. The same reference numerals as used in FIG. 1A FIG. 1B and are also used for the same members in FIGS. 6 and 7.

First, the fourth absorbent sheet will be described.

As shown in FIG. 6, the fourth absorbent sheet 40 contains at least a superabsorbent polymer, bulky cellulose fibers, and hydrophilic fine fibers or hydrophilic fine particles (hereinafter sometimes inclusively referred to as hydrophilic fine fibers or particles). The fourth absorbent sheet 40 comprises the fiber aggregate 15 and the fiber web 18. The fiber aggregate 15 has the absorbent surface 12 and does not contain the superabsorbent polymer at the side of the absorbent surface 12. The fiber aggregate 15 predominantly comprises bulky cellulose fibers 13 having a degree of fiber roughness of 0.3 mg/m or more.

As shown in FIG. 6, the fiber web 18 contains bulky cellulose fibers having an average fiber length of 1 to 20 mm and a degree of fiber roughness of 0.3 mg/m or more, and hydrophilic fine fibers having an average fiber length of 0.02 to 0.5 mm. The proportion of the hydrophilic fine fibers in one side of the fiber web 18 is higher than that in the other side, and the fiber web 18 is in contact with the fiber aggregate 15 at the side having a lower proportion of the hydrophilic fine fibers.

As shown in FIG. 6, the fiber aggregate 15 and the fiber web 18 are in a unitary body. The superabsorbent polymer 16 is contained in the fourth absorbent sheet 40, while sticking to the fibers constituting fourth absorbent sheet.

The fourth absorbent sheet 40 is characterized by its ultrathin unitary structure which comprises the fiber aggregate 15 and the fiber web 18 and contains the superabsorbent polymer 16 in the inside thereof. Such an ultrathin unitary structure is the same as in the first absorbent sheet, and the explanation given to the unitary structure of the first absorbent sheet also applies to the fourth absorbent sheet.

Entering into the details, the fiber web 18 comprises bulky cellulose fibers having an average fiber length of 1 to 20 mm and a degree of fiber roughness of 0.3 mg/m or more, and hydrophilic fine fibers having an average fiber length of 0.02 to 0.5 mm. The proportion of the hydrophilic fine fibers or particles is higher in one side of the fiber web than in the other side. The side having a lower proportion of the hydrophilic fine fibers exhibits excellent performance in terms of rate of liquid absorption and local liquid absorptivity and also excellent liquid permeability. On the other hand, the side having a higher proportion of the hydrophilic fine fibers has excellent liquid diffusing properties because the hydrophilic fine fibers have a large surface area, so that it quickly diffuses the liquid having passed through the side having a lower proportion of the hydrophilic fine fibers or particles. Thus, the fiber web 18 combines a liquid permeation function and a liquid diffusing function in spite of its single structure. As described above, the fiber web 18 is in contact with the fiber aggregate 15 at the side having a lower proportion of the hydrophilic fine fibers.

For the sake of convenience, the side having a lower proportion of the hydrophilic fine fibers will hereinafter referred to as first side, while the other side having a higher proportion of the hydrophilic fine fibers as second side.

As shown in FIG. 6, since the area including the first side and its vicinities consists mainly of bulky cellulose fibers, it has a function of quickly absorbing liquid and quickly transferring the liquid to the second side. That is, this area serves primarily as a "permeable layer". On the other hand, since the area including the second side and its vicinities predominantly comprises the hydrophilic fine fibers, it has a function of quickly diffusing the liquid having permeated through the first side. That is, this area serves primarily as a "diffusing layer". Thus, the fiber web 18 in the fourth absorbent sheet is characterized by combining a permeable layer and a diffusing layer in its single structure. As a result, the fourth absorbent sheet has high liquid absorbing properties and yet affords a dry feel after liquid absorption.

As mentioned above, there is a great difference in liquid diffusing properties between the first and second sides of the fiber web 18. That is, liquid is rapidly diffused in the second side (i.e., diffusing layer) which predominantly comprises hydrophilic fine fibers, whereas liquid is absorbed and permeated rapidly but is not so quick as to be diffused in the first side (permeable layer) which predominantly comprises the bulky cellulose fibers. In other words, the fiber web 18 has a liquid diffusion gradient in its thickness direction.

The increase of the proportion of the hydrophilic fine fibers from the first side to the second side in the fiber web 18 may be either continuous or discontinuous (in steps) at a certain depth.

On the other hand, the bulky cellulose fibers may be uniformly distributed in the thickness direction of the fiber web 18, but is preferably present in the first side in a higher proportion than in the second side of the fourth absorbent sheet. That is, the proportion of the bulky cellulose fibers preferably has a gradient in the thickness direction of the fiber web 18. The increase of the proportion of the bulky cellulose fibers from the second side to the first side may be either continuous or in steps at a certain depth.

In greater detail, in a preferred mode of gradation, about 5 to 70% by weight, still preferably about 10 to 50% by weight of the total hydrophilic fine fibers or particles are present in the area from the surface of the second side to about $\frac{1}{3}$ the thickness of the fiber web 18 to form the above-mentioned diffusing layer predominantly comprising the hydrophilic fine fibers.

It is preferable, on the other hand, that about 60 to 100% by weight, still preferably about 70 to 97% by weight, of the total bulky cellulose fibers be present in the area from the first side to about $\frac{2}{3}$ the thickness of the fiber web 18 to form the above-mentioned permeable layer predominantly comprising the bulky cellulose fibers.

The proportions of the bulky cellulose fibers and the hydrophilic fine fibers or particles in the fiber web 18 are not particularly limited. It is preferred that the bulky cellulose fibers are preferably present in an amount of 50 to 97 parts by weight, still preferably 70 to 95 parts by weight, per 100 parts by weight of the fiber web. If the proportion of the bulky cellulose fibers is less than 50 parts by weight, the resulting web has insufficient bulkiness in its network structure and tends to fail to combine a permeation function and a diffusing function. If the proportion exceeds 97 parts by weight, the proportion of the hydrophilic fine fibers is low for obtaining sufficient diffusing properties. Accordingly, the proportion of the bulky cellulose fibers preferably falls within the above range.

The hydrophilic fine fibers are preferably present in an amount of 3 to 50 parts by weight, still preferably 5 to 30 parts by weight, per 100 parts by weight of the fiber web. If the proportion of the hydrophilic fine fibers is less than 3 parts by weight, the fiber web has insufficient diffusing properties. If it exceeds 50 parts by weight, the proportion of the fine fibers in the first side of the fiber web becomes large only to have insufficient liquid permeability. Accordingly, the proportion of the hydrophilic fine fibers preferably falls within the above range.

Next, the bulky cellulose fibers will be described.

Any kind of cellulose fibers selected from the bulky cellulose fibers described with reference to the first absorbent sheet can be used as far as the fibers have an average fiber length of 1 to 20 mm and a degree of fiber roughness of 0.3 mg/m or more, and the fibers are bulky. If the average fiber length is less than 1 mm, a bulky network structure cannot be formed. Besides, the hydrophilic fine fibers cannot pass through the bulky network structure as hereinafter described. If the average fiber length is longer than 20 mm, the fibers have poor dispersibility in water, failing to provide a uniform network structure. The bulky cellulose fibers preferably have an average fiber length of 2 to 10 mm, still preferably 2 to 5 mm.

Next, the above-mentioned hydrophilic fine fibers will be described.

The hydrophilic fine fibers have a hydrophilic surface and an average fiber length of 0.02 to 0.5 mm, preferably 0.1 to 0.3 mm. If the average fiber length is less than 0.02 mm, such fine fibers would pass through a paper making wire and cannot be accumulated on the wire when the fiber web is prepared by the preferred process hereinafter described. If the average fiber length exceeds 0.5 mm, such fibers cannot pass through the network structure made up of the bulky cellulose fibers and cannot be accumulated on the wire when the fiber web is prepared by the preferred process for producing the fiber web hereinafter described.

As far as the above requirements are met, the hydrophilic fine fibers are not particularly limited. For example, in addition to the hydrophilic fine fibers as used in the second and the third absorbent sheets, inorganic fibers such as kaolin, bentonite and hydrotalcite. These hydrophilic fine fibers may be used either individually or as a mixture of two or more thereof.

Commercially available hydrophilic fine fibers can be made use of. Among useful commercial products is "Pulp Flock", a product of Sanyo-Kokusaku Pulp Co., Ltd., which is prepared by beating wood pulp, such as softwood pulp or hardwood pulp, mechanically grinding the beaten pulp, followed by classifying using a sieve having 0.5 mm or smaller openings. Also included are fine cellulose fibers obtained by mechanically grinding cellulose fibers, such as wood pulp, hydrolyzing with an acid, and further mechanically grinding (e.g., "KC Flock" produced by Sanyo-Kokusaku Pulp Co., Ltd. and "Avicel" produced by Asahi Chemical Industry Co., Ltd.). Commercially available inorganic fine fibers include water-containing magnesium silicate fibers (e.g., "Eight Plus ML-30" produced by Mizusawa Kagaku Kogyo K.K.). Of these commercial products, fine cellulose fibers obtained by finely grinding pulp are preferred for their inexpensiveness.

The superabsorbent polymer 16 which is contained in the fourth absorbent polymer 40 is now explained.

As shown in FIG. 6, the superabsorbent polymer 16 is contained in the fourth absorbent sheet 40 and dispersed in the spaces formed among the fibers constituting the fourth absorbent sheet 40 similarly to the superabsorbent polymer 16 in the first absorbent sheet 10. In more detail, as shown in FIG. 3, the superabsorbent polymer 16 is mostly present in the inside of the fiber web 18, i.e., contained primarily in the area from the interface between the fiber web 18 and the fiber aggregate 15 to the inside of the fiber web 18, and is preferably dispersed in the spaces formed among the fibers constituting the fiber web 18 as shown in FIG. 6.

The superabsorbent polymer 16 sticks to the fibers constituting the fourth absorbent sheet 40, preferably to the fibers constituting the fiber web 18.

As for other particulars concerning the superabsorbent polymer 16, for example, the dispersed state, the kind, the amount to be spread, and various physical properties, the corresponding explanation made for the superabsorbent polymer 16 used in the first absorbent sheet 10 applies appropriately.

In the fourth absorbent sheet 40 having the above-mentioned structure, there is a diffusion gradient in its single structure. In detail, the absorbent surface 12 of the fourth absorbent sheet 40 has high liquid permeability so that little liquid remains on the absorbent surface 12. Passing through the first side, the absorbed liquid rapidly reaches the superabsorbent polymer 16 and is diffused throughout the entire area of the fourth absorbent sheet 40, preferentially in the second side of the fiber web 18 having high diffusing properties. Thus, since the fourth absorbent sheet 40 combines a permeation function, a diffusion function, and a fixing function in its single structure, it can fix liquid in the superabsorbent polymer 16 quickly and securely.

Further, when fourth absorbent sheet absorbs a large quantity of liquid, the liquid is quickly transferred to the superabsorbent polymer 16 and absorbed therein. Even if the liquid is too much to be completely retained by the superabsorbent polymer 16, the liquid is diffused in the second side of the fiber web 18 and thus prevented from leaking. Accordingly, the fourth absorbent sheet 40 is especially effective where a large quantity of liquid should be absorbed at a time or where a superabsorbent polymer having a low rate of liquid absorption is used.

The fifth absorbent sheet according to the present invention is now described below.

As shown in FIG. 7, the fifth absorbent sheet 50 contains at least a superabsorbent polymer, bulky cellulose fibers, and hydrophilic fine fibers. The fifth absorbent sheet 50 comprises the fiber aggregate 15 and the fiber web 18. The fiber aggregate 15 has the absorbent surface 12 and does not contain the superabsorbent polymer at the side of the absorbent surface 12. The fiber aggregate 15 comprises the bulky cellulose fibers 13 having an average fiber length of 1 to 20 mm and a degree of fiber roughness of 0.3 mg/m or more, and the hydrophilic fine fibers 14 having an average fiber length of 0.02 to 0.5 mm. The proportion of the hydrophilic fine fibers in fiber aggregate 15 is higher on one side thereof than on the other side.

As shown in FIG. 7, the fiber web 18 predominantly comprises the bulky cellulose fibers 13 having a degree of fiber roughness of 0.3 mg/m or more, and is located adjacent to the side of the fiber aggregate having a higher proportion of the hydrophilic fine fibers.

For the sake of convenience, the side having a lower proportion of the hydrophilic fine fibers will hereinafter referred to as a first side, while the other side having a higher proportion of the hydrophilic fine fibers as a second side.

As shown in FIG. 7, fiber aggregate and the fiber web 18 are in a unitary body. Further, the superabsorbent polymer 16 is contained in the fifth absorbent sheet 50 and sticks to the fibers constituting the fifth absorbent sheet 50.

Similarly to the first absorbent sheet, the fifth absorbent sheet 50 is characterized by its ultrathin unitary structure which comprises the fiber aggregate 15 and the fiber web 18 and contains the superabsorbent polymer 16 in the inside thereof. Such an ultrathin unitary structure is the same as in the first absorbent sheet, and the explanation given to the unitary structure of the first absorbent sheet also applies to the fifth absorbent sheet appropriately.

The fiber web 18 in the fifth absorbent sheet 50 is described below.

As mentioned above, the fiber web 18 predominantly comprises bulky cellulose fibers having a degree of fiber roughness of 0.3 mg/m or more, and adjoins the side of the fiber aggregate 15 having a higher proportion of the hydrophilic fine fibers, i.e., the second side of the fiber aggregate 15. Use of the bulky cellulose fibers not only brings about further improvement on the dispersibility and the degree of fixing of the superabsorbent polymer 16 but makes it easier to control the drainage properties of the fiber web 18 in wet paper making. Further, bulky cellulose fibers form a bulky fiber web having a high void content so that the superabsorbent polymer 16 can be easily embedded, dispersed and fixed therein three-dimensionally in the fiber web 18, and gel blocking of the superabsorbent polymer 16 can be suppressed.

As for other undescribed particulars of the fiber web 18, the corresponding explanation given to the first absorbent sheet 10 applies appropriately.

The superabsorbent polymer 16 which is contained in the inside of the fifth absorbent sheet 50 is explained.

As shown in FIG. 7, the superabsorbent polymer 16 is contained in the inside of the fifth absorbent sheet 50 and dispersed in the spaces formed among the fibers constituting the fifth absorbent sheet 50, similarly to the superabsorbent polymer 16 of the first absorbent sheet 10. In more detail, as shown in FIG. 7, it is preferable that the superabsorbent polymer 16 be mostly contained in the fiber web 18, i.e., contained primarily in the area from the interface between the fiber web 18 and the fiber aggregate 15 to the inside of the fiber web 18, and dispersed in the spaces formed among the fibers constituting the fiber web 18.

The superabsorbent polymer 16 sticks to the fibers constituting the fifth absorbent sheet 50, preferably to the fibers constituting the fiber web 18.

As for other particulars concerning superabsorbent polymer 15, for example, the dispersed state, the kind, the amount to be spread, and various physical properties, the corresponding explanation made for the superabsorbent polymer used in the first absorbent sheet applies appropriately.

The fiber aggregate 15 having the absorbent surface 12 in the fifth absorbent sheet 50 is described below.

The fiber aggregate 15 contains bulky cellulose fibers having an average fiber length of 1 to 20 mm and a degree of fiber roughness of 0.3 mg/m or more, and hydrophilic fine fibers having an average fiber length of 0.02 to 0.5 mm, the proportion of the hydrophilic fine fibers being higher in one side of the fiber aggregate than in the other side. The side having a lower proportion of the hydrophilic fine fibers or particles (called a first side) corresponds to the absorbent surface 12.

The side having a higher proportion of the hydrophobic fine fibers (called a second side) adjoins the fiber web 18 as shown in FIG. 7.

Thus, the fiber aggregate 15 has a gradient of proportion of the hydrophilic fine fibers in the thickness direction. The structure of the fiber aggregate 15 having such gradation is the same as that of fiber web of the fourth absorbent sheet 40. Accordingly, the explanation made for the fiber web 18 of the fourth absorbent sheet 40 applies to the details, for example the structure, of the fiber aggregate 15 of the fifth absorbent sheet 50. With respect to the bulky cellulose fibers and the hydrophilic fine fibers which constitute the fiber aggregate 15, the corresponding explanation as to the fiber web 18 of the fourth absorbent sheet 40 applies appropriately.

As described above, the fifth absorbent sheet 50 of the present invention predominantly comprises the fiber aggregate 15, the fiber web 18, and the superabsorbent polymer 16. Preferred basis weights of these materials are the same as those in the first absorbent sheet, and the corresponding explanation made to the first absorbent sheet 10 applies appropriately.

The details of the basis weight, thickness, etc. of fifth absorbent sheet are also the same as those of the first absorbent sheet 10, and the corresponding explanation made for the first absorbent sheet 10 applies appropriately.

There is a diffusion gradient in the fifth absorbent sheet 50 having the above-mentioned structure. In detail, similarly to the fourth absorbent sheet 40, the fifth absorbent sheet 50 exhibits gradation in liquid absorption from the absorbent surface 12 toward the inside (especially in the fiber aggregate 15). That is, the vicinities of the absorbent surface 12 (first side) of the fifth absorbent sheet 50 form a bulky network made up predominantly of bulky cellulose fibers. Therefore this area has high liquid permeability, and liquid is quickly transferred to the inside of aggregate 15. The vicinities of the second side of the fiber aggregate 15 predominantly comprises the hydrophilic fine fibers having a high surface area. Therefore, the liquid having passed through the first side area is quickly diffused throughout the entire area of the fifth absorbent sheet 50 and fixed efficiently by the superabsorbent polymer 16. Thus, similarly to the fourth absorbent sheet, the fifth absorbent sheet 50 combines a permeation function, a diffusion function, and a fixing function in its single structure, and it can fix liquid in the superabsorbent polymer 16 quickly and securely.

Figure 8:
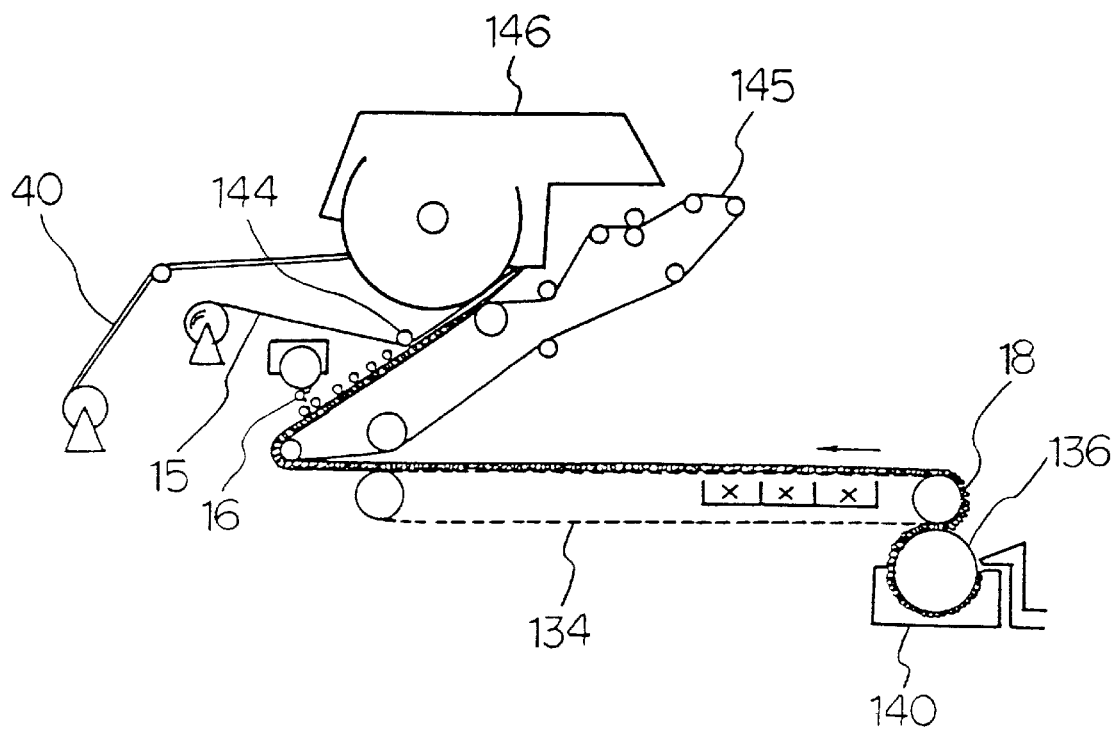
FIG. 8 is a schematic view illustrating an apparatus which can be preferably used for producing the fourth absorbent sheet of the present invention.

A process which can be preferably used for the production of the fourth and fifth absorbent sheets will be described below by referring to the drawings. FIG. 8 is a schematic view illustrating an apparatus which can be preferably used for the production of the fourth absorbent sheet of the present invention which corresponds to FIG. 2. While not particularly mentioned, the same explanation given to FIG. 2 applies appropriately to the corresponding members of FIG. 8. The same reference numerals as used in FIG. 2 are used for the same members of FIG. 8.

The preferred process for producing the fourth absorbent sheet comprises the steps of:

spreading a superabsorbent polymer on a wet fiber web comprising bulky cellulose fibers having an average fiber length of 1 to 20 mm and a degree of fiber roughness of 0.3 mg/m or more, and hydrophilic fine fibers having an average fiber length of 0.02 to 0.5 mm, the proportion of the hydrophilic fine fibers being higher in one of the sides of the fiber web than in the other side, the spreading of the superabsorbent polymer being in the side having a lower proportion of the hydrophilic fine fibers;

overlaying on the fiber a fiber aggregate which predominantly comprises bulky cellulose fibers having a degree of fiber roughness of 0.3 mg/m or more; and drying the combination of the fiber web and the fiber aggregate and forming a unitary body thereof.

Going into details, the fiber web can be prepared by a wet paper making process as follows. To begin with, both the bulky cellulose fibers and the hydrophobic fine fibers are dispersed in water to prepare a slurry. The slurry is supplied to the forming part 140 and applied to paper making cylinder 136. When the slurry is supplied to the paper making cylinder 136, the water of the applied slurry is drained through the cylinder 136 thereby to form a wet fiber web 18 on the cylinder 136. As shown in FIG. 8, the bulky cellulose fibers form a bulky network structure over the entire thickness of the fiber web 18. On the other hand, the hydrophilic fine fibers in the slurry, which are finer than the bulky cellulose fibers, pass through the network structure together with water and accumulated on the cylinder 136. As a result, the hydrophilic fine fibers are distributed with a gradient in thickness direction of the fiber web 18. That is, the proportion of the fine fibers is higher in the side in contact with the cylinder 136 than in the other side.

Thus, according to the preferred process for producing the fiber web 18, which utilizes a wet paper making process, the difference in size between the bulky cellulose fibers and the hydrophilic fine fibers is taken advantage of for providing a gradient in proportion of the hydrophilic fine fibers in the thickness direction of the fiber web 18.

The wet fiber web 18 thus formed is taken up on the wire 134 with its sides turned over as shown in FIG. 8. The fiber web 18 is then taken up on the conveyor 145 with its sides turned over again, and the superabsorbent polymer 16 is spread on the fiber web 18 while wet. The surface on which the superabsorbent polymer 16 is spread is on the side having a lower proportion of the hydrophilic fine fibers, i.e., the first side.

While not particularly mentioned, the steps following the formation of the fiber web 18 are the same as those in the preferred process for producing the first absorbent sheet. The corresponding explanation made for the preferred process for producing the first absorbent sheet appropriately applies.

There is thus obtained the fourth absorbent sheet according to the present invention.

A process which can preferably be used for the production of the fifth absorbent sheet comprises the steps of:

spreading a superabsorbent polymer on a wet fiber web which predominantly comprises bulky cellulose fibers having a degree of fiber roughness of 0.3 mg/m or more;

overlaying thereon a fiber aggregate which comprises bulky cellulose fibers having an average fiber length of 1 to 20 mm and a degree of fiber roughness of 0.3 mg/m or more, and hydrophilic fine fibers having an average fiber length of 0.02 to 0.5 mm, the proportion of the hydrophilic fine fibers being higher on one of the sides of the fiber aggregate than on the other side, in such a manner that the side of the fiber aggregate having a higher proportion of the hydrophilic fine fibers is brought into contact with the fiber web; and drying a combination of the fiber web and the fiber aggregate and forming a unitary body thereof.

The preferred process for producing the fifth absorbent sheet is substantially the same as the preferred process for producing the first absorbent sheet, and the fifth absorbent sheet can be produced by using the apparatus shown in FIG. 2, which is preferably used for the production of the first absorbent sheet. The difference consists in that the fiber aggregate 15 comprising the bulky cellulose fibers and hydrophilic fine fibers, the proportion of the hydrophilic fine fibers being higher in one side of the fiber aggregate than in the other side, is overlaid on the surface of the fiber web 18 on which the superabsorbent polymer 16 has been spread, in such a manner that the side of the fiber aggregate 15 having a higher proportion of the hydrophilic fine fibers (i.e., the second side) is brought into contact with the fiber web 18.

In this case, the fiber aggregate 15 may previously be prepared by a wet paper making process taking advantage of the difference in size between the bulky cellulose fibers and the hydrophilic fine fibers (the same as the preferred process for preparing the fiber web 18 of the fourth absorbent sheet 40), and a roll of the previously prepared fiber aggregate may be unwound for overlaying. Alternatively, the fiber aggregate 15 may be prepared concurrently with the preparation of the fiber web 18. For the details of the preparation of the fiber aggregate 15 by a wet paper making process taking advantage of the difference in size between the bulky cellulose fibers and the hydrophilic fine fibers or particles, the explanation given to the preferred process for preparing the fiber web 18 of the fourth absorbent sheet 40 can be applied appropriately.

Figure 9:
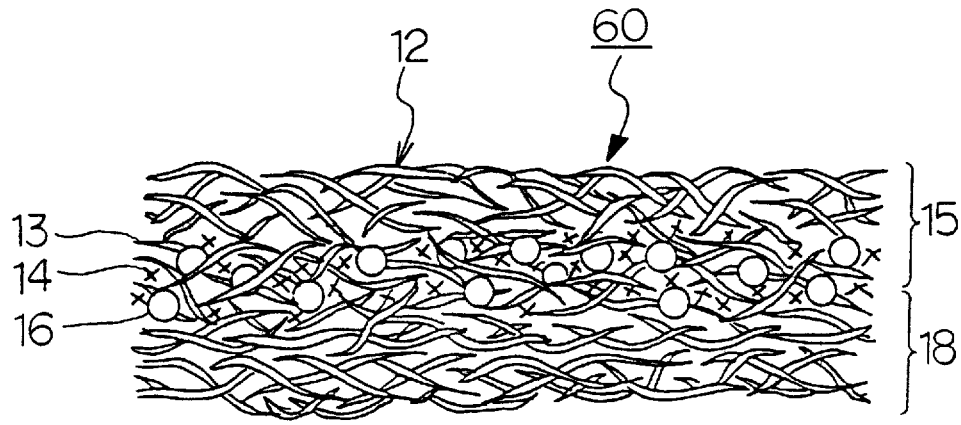
FIG. 9 is a schematic view illustrating the cross section of the sixth absorbent sheet of the present invention, which corresponds to FIG. 1B.

The sixth absorbent sheet according to the present invention will be described in detail by referring to the drawing. FIG. 9 is a schematic cross section of the sixth absorbent sheet, which corresponds to FIG. 1B.

While not giving particulars, the same explanation as given to FIG. 1A and FIG. 1B applies to the corresponding points of FIG. 9. The same reference numerals as used in FIG. 1A and FIG. 1B are also used for the same members in FIG. 9.

As shown in FIG. 9, the sixth absorbent sheet 60 contains at least the superabsorbent polymer 16, the bulky cellulose fibers 13, and hydrophilic fine fibers or particles 14, in which the sixth absorbent sheet 60 comprises the fiber aggregate 15 and the fiber web 18. The fiber aggregate 15 has the absorbent surface 12, and does not contain the superabsorbent polymer at the side of the absorbent surface 12. The fiber aggregate 15 predominantly comprises the bulky cellulose fibers 13.

The fiber web 18 predominantly comprises the bulky cellulose fibers 13 as shown in FIG. 9.

Also, as shown in FIG. 9, the fiber aggregate 15 and the fiber web 18 form a unitary body as shown in FIG. 9. The superabsorbent polymer 16 is contained in the sixth absorbent sheet 60, while sticking to the fibers constituting the sixth absorbent sheet 60.

As shown in FIG. 9, the above-mentioned hydrophilic fine fibers or particles 14 are contained mainly in the area where the superabsorbent polymer 16 is present, so that a layer made up of hydrophilic fine fibers or particles 14 is formed around the superabsorbent polymer 16.

Thus, the sixth absorbent sheet 60 is characterized by its ultrathin unitary structure which consists of the fiber aggregate 15 and the fiber web 18 and contains the superabsorbent polymer 16 in the inside thereof, in which hydrophilic fine fibers or particles 14 are contained mainly in the area where the superabsorbent polymer 16 is present. Such an ultrathin unitary structure is the same as in the first absorbent sheet, and the explanation given to the unitary structure of the first absorbent sheet also applies to the sixth absorbent sheet.

Next, the superabsorbent polymer 16 contained in the sixth absorbent sheet 6 is described below.

As shown in FIG. 9, the superabsorbent polymer 16 is contained in the sixth absorbent sheet 60 and dispersed in the spaces formed among the fibers constituting the sixth absorbent sheet 60. In more detail, the superabsorbent polymer 16 is preferably contained mainly in the fiber web 18 hereinafter described and dispersed in the spaces formed among the fibers constituting the fiber web 18 as shown in FIG. 9.

The superabsorbent polymer 16 sticks to the fibers constituting the sixth absorbent sheet 60, preferably to the fibers constituting the fiber web 18. As for undescribed other particulars concerning the superabsorbent polymer, for example, the dispersed state, the kind, the amount to be spread, and various physical properties, the corresponding explanation made for the superabsorbent polymer used in the first absorbent sheet applies appropriately.

Next, the hydrophilic fine fibers or particles 14 contained mainly in the area where the superabsorbent polymer is present.

As shown in FIG. 9, hydrophilic fine fibers or particles 14 are contained mainly in the area where the superabsorbent polymer 16 is present, forming a layer different from the fiber web 18. The hydrophilic fine fibers or particles 14 having a large surface area exhibit improved liquid diffusing performance through capillary action, thereby affording improved liquid diffusion in the vicinities of the interfaces among the superabsorbent polymer 16. In addition, since hydrophilic fine fibers or particles 14 are present among the superabsorbent polymer, gel blocking of the superabsorbent polymer 16 having absorbed liquid and been swollen with the liquid can be prevented effectively.

The hydrophilic fine fibers or particles are preferably used in an amount of 1 to 300 $g/m^2$, more preferably 5 to 200 $g/m^2$, still preferably 5 to 150 $g/m^2$. If the amount of the hydrophilic fine fibers or particles is less than 1 $g/m^2$, there is a tendency that liquid cannot be effectively diffused in the vicinities of the superabsorbent polymer, or gel blocking of the superabsorbent polymer cannot be effectively prevented. If the amount exceeds 300 $g/m^2$, the density of the fine fibers or particles in the vicinities of the superabsorbent polymer is too high, tending to reduce the properties of transferring liquid to the superabsorbent polymer or tending to make the absorbent sheet hard. Accordingly, the basis weight of the fine fibers or particles preferably falls within the above range.

The hydrophilic fine fibers or particles preferably have a degree of fiber roughness of less than 0.1 mg/m, or preferably have a degree of fiber roughness of less than 0.3 mg/m and a degree of fiber roundness in the fiber cross section of 0.01 to 0.5. Hydrophilic fine fibers or particles having such physical properties are preferred for their large specific surface area.

It is also desirable for the hydrophilic fine fibers or particles to have an average fiber length or an average particle diameter of 0.02 to 0.5 mm for increasing the specific surface area. It is still preferred that the average fiber length or particle diameter is 0.1 to 0.3 mm.

The hydrophilic fine fibers or particles are preferably subjected to crosslinking treatment. Since crosslinked fine fibers or particles are inhibited from absorbing liquid and swelling, they do not change the distance among themselves even when wetted and therefore do not reduce the properties of transferring the liquid. Further, the crosslinked cellulose fine fibers or particles, when spread in a large quantity, do not have too a high density. Examples of such fine fibers or fine particles include, for example, crosslinked cellulose fibers, cellulose particles and hydrophilic synthetic fibers.

Specific examples of the above-described hydrophilic fine fibers include those used in the fourth and fifth absorbent sheets. Examples of the hydrophilic fine particles include those made of cellulose particles, such as pulp, cotton, and rayon; and inorganic particles, such as kaolin, bentonite, and hydrotalcite. These hydrophilic fine fibers or particles may be used either individually or as a mixture of two or more thereof. A mixture of the hydrophilic fine fibers and the hydrophilic fine particles may also be used.

In the sixth absorbent sheet 60 having the above-mentioned structure, there is a diffusion gradient in its single structure. In detail, since the side of the absorbent surface 12 of the sixth absorbent sheet 60 consists mainly of the bulky cellulose fibers, it has high liquid permeability so that little liquid remains on the absorbent surface 12. The absorbed liquid rapidly reaches the superabsorbent polymer 16 and particularly in the layer made up of highly diffusive hydrophilic fine fibers or particles (i.e., in the area where the superabsorbent polymer is present), the performance of diffusing liquid is increased by the capillary actions of the hydrophilic fine fibers or the hydrophilic particles, thereby increasing the performance of diffusing the liquid near the interfaces between the superabsorbent polymers. The sixth absorbent sheet 60 combines a permeation function, a diffusion function, and a fixing function in its single structure, it can fix liquid in the superabsorbent polymer 16 quickly and securely. Besides, since there are the hydrophilic fine fibers or particles among individual superabsorbent polymer particles, gel blocking of the superabsorbent polymer is effectively prevented.

Figure 10:
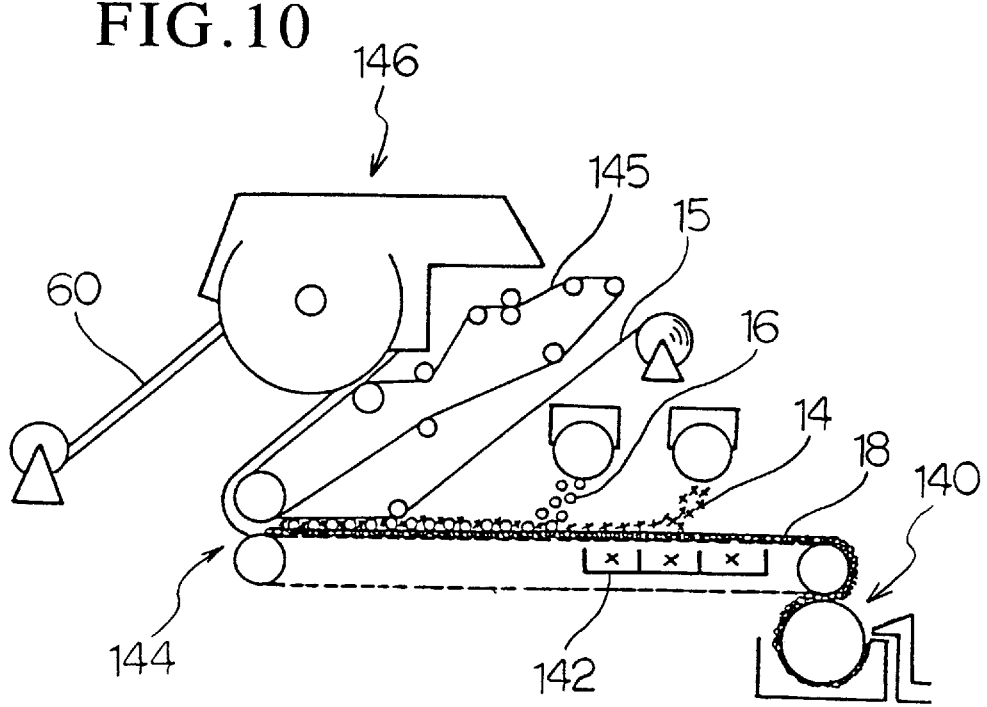
FIG. 10 is a schematic view illustrating an apparatus which can be preferably used for producing the sixth absorbent sheet of the present invention.
Figure 11:
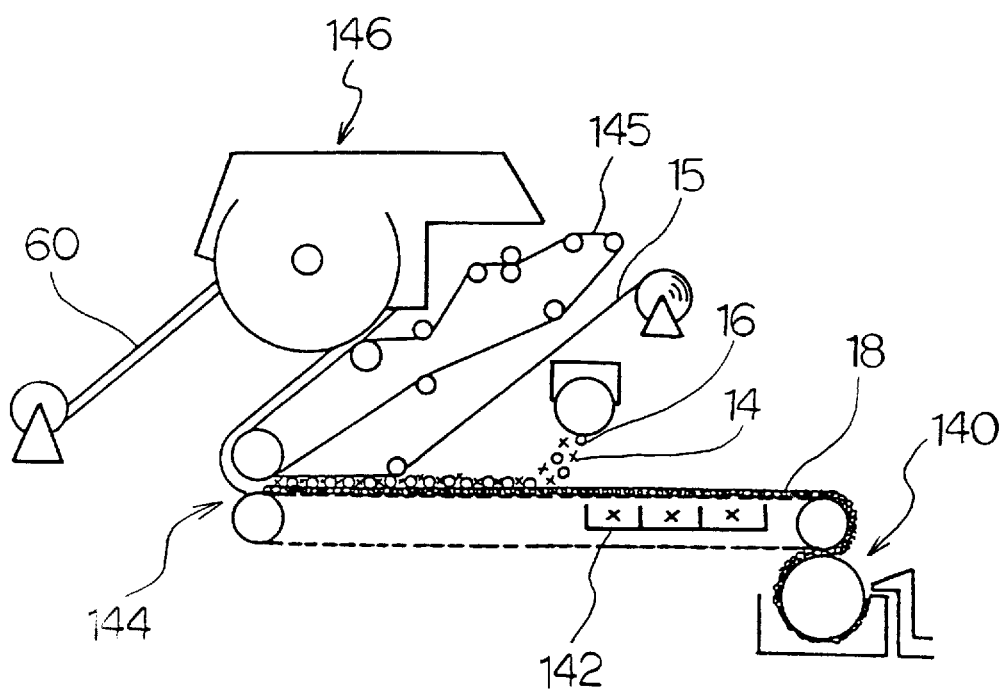
FIG. 11 is a schematic view illustrating another apparatus which can be preferably used for producing the sixth absorbent sheet of the present invention.

A process which can be preferably used for the production of the sixth absorbent sheet will be described below by referring to the drawings. FIG. 10 is a schematic view illustrating an apparatus which can be preferably used for the production of the sixth absorbent sheet of the present invention. FIG. 11 is a schematic view illustrating another apparatus which can also be preferably used for the production of the sixth absorbent sheet. FIGS. 10 and 11 correspond to FIG. 2. While not particularly mentioned, the same explanation given to FIG. 2 applies to the corresponding members of FIGS. 10 and 11. The same reference numerals as used in FIG. 2 are used for the same members of FIGS. 10 and 11.

The preferred process for producing the sixth absorbent sheet comprises the steps of:

spreading superabsorbent polymer on a wet fiber web comprising at least bulky cellulose fibers, and spreading hydrophilic fine fibers or hydrophilic fine particles upon, or before or after spreading the superabsorbent polymer;

overlaying a fiber aggregate on the fiber web; and drying a combination of the fiber web and the fiber aggregate and forming a unitary body thereof.

The preferred process for producing the sixth absorbent sheet is substantially the same as the preferred process for producing the first absorbent sheet. The difference resides in that the hydrophilic fine fibers or particles are spread simultaneously with, or before or after spreading the superabsorbent polymer. Thus, the hydrophilic fine fibers or particles are made to exist mainly in the area where the superabsorbent polymer exists thereby to form a layer of the hydrophilic fine fibers or particles. As a result, the liquid diffusibility in the vicinities of the interfaces of the superabsorbent polymer is improved and, at the same time, the effects of the superabsorbent polymer to fix the liquid are improved, and gel blocking of the superabsorbent polymer can be prevented effectively.

The hydrophilic fine fibers or particles may be spread uniformly over the entire surface of the fiber web similarly to the superabsorbent polymer. If desired, they may be spread in stripes extending in the longitudinal direction of the fiber web at certain intervals, or may be spread intermittently in the longitudinal direction of the fiber web. They are preferably spread in the same manner as the superabsorbent polymer.

The spreading of the superabsorbent polymer and the hydrophilic fine fibers or particles is described in detail with reference to FIGS. 10 and 11.

Where spreading of hydrophilic fine fibers or particles 14 is followed by spreading of the superabsorbent polymer 16, hydrophilic fine fibers or particles 14 are first spread on the fiber web 18 formed by wet paper making as shown in FIG. 10. Immediately thereafter, the superabsorbent polymer 16 is spread thereon. The fiber aggregate 15 previously formed is then overlaid on the fiber web 18 on which hydrophilic fine fibers or particles 14 and the superabsorbent polymer 16 have been spread thereon.

Where the superabsorbent polymer 16 and hydrophilic fine fibers or particles 14 are simultaneously spread, the superabsorbent polymer 16 and hydrophilic fine fibers or particles 14 are previously mixed uniformly at a prescribed mixing ratio, and the mixture is spread on the fiber web 18 formed by wet paper making as shown in FIG. 11. The fiber aggregate 15 is then overlaid on the fiber web 18 having the mixture spread thereon.

In FIG. 10, the order of spreading hydrophilic fine fibers or particles 14 and the superabsorbent polymer 16 may be reversed.

In the absorbent sheet according to the present invention, the fiber density of the absorbent sheet is higher in the vicinity of the superabsorbent polymer than in the absorbent surface for absorbing liquid, and therefore the performance of diffusing liquid is enhanced in the vicinity of the superabsorbent polymer. Accordingly, unlike the conventional absorbent sheets, the absorbent sheet according to the present invention needs neither to be subjected to spreading of other fibers nor to be combined with other composite papers for the purpose of complementing performance of diffusing liquid.

The reason why the gradient of the fiber density is formed is considered to be as follows.

That is, when the superabsorbent polymer is spread on the wet fiber web, the superabsorbent polymer absorbs water to become sticky and sticks to the fibers. In this occasion, the fibers constituting the fiber web still have freedom, and therefore the fibers draw near to the superabsorbent polymers having absorbed water and partially aggregate. After the following drying step, the distance between the fibers and the superabsorbent polymers further decreases, so that the combination of the fiber web and the superabsorbent polymer is formed into a sheet in the state that the fibers aggregate around the superabsorbent polymer.

Absorbent articles using the first to sixth absorbent sheets according to the present invention will then be illustrated.

The absorbent article according to the present invention comprises at least a liquid retentive absorbent member, and a liquid impermeable backsheet, which is characterized in that the absorbent member comprises any one of the first to sixth absorbent sheets.

Preferred embodiments of the absorbent article of the present invention are explained by referring to the drawings, taking the embodiments of using the first absorbent sheet for an instance.

First of all, preferred embodiments of the absorbent article of the present invention are explained by referring to FIGS. 12 through 17.

Figure 12:
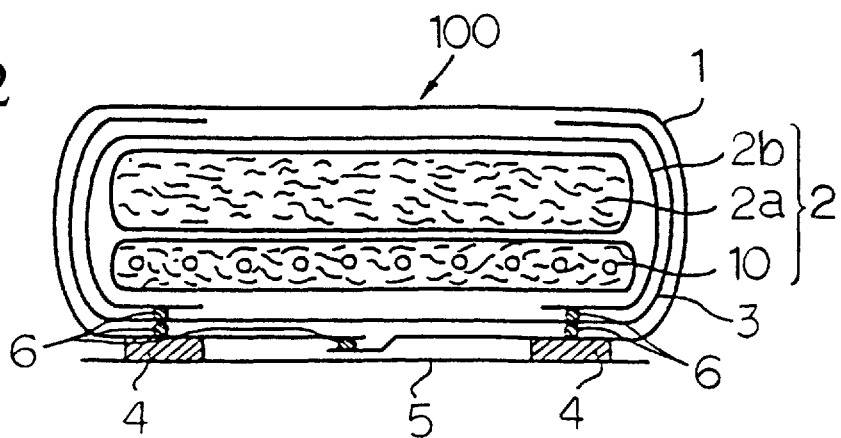
FIG. 12 is a schematic view illustrating the transverse section of a sanitary napkin as a first preferred embodiment of the absorbent article according to the present invention.

FIG. 12 is a schematic transverse section of a sanitary napkin as a first preferred embodiment of the absorbent article according to the present invention. FIGS. 13 to 17 are each a schematic transverse section of a sanitary napkin according to other preferred embodiments of the absorbent article according to the present invention, which correspond to FIG. 2.

The sanitary napkin 100 shown in FIG. 12, as a first preferred embodiment of the absorbent article of the present invention, comprises a liquid permeable topsheet 1, a liquid impermeable backsheet 3, and a liquid retentive absorbent member 2 interposed between the topsheet 1 and the backsheet 3.

In detail, the sanitary napkin 100 has a substantially rectangular shape. The napkin 100 is applied to the body with the topsheet 1 in contact with the skin, and the backsheet 3 with underwear.

Absorbent member 2 comprises the first absorbent sheet 10, a fluff pulp 2a, and an absorbent paper 2b which covers the first absorbent sheet 10 and the fluff pulp 2a. The backsheet 3 covers both the sides and the bottom of the absorbent member 2. The topsheet 1 covers all the surfaces of the combination of the absorbent member 2 and the backsheet 3.

Topsheet 1 is not particularly limited as far as it allows liquid to permeate into the absorbent member 2. Materials having an underwear-like touch are preferred. Such materials include thermoplastic woven cloth, nonwoven cloth and porous films. Porous films comprising polyolefins, such as low-density polyethylene, are particularly preferred.

The backsheet 3 is not particularly limited as far as it is impermeable to liquid. Materials having moisture permeability and an underwear-like touch are preferred. A moisture permeable and liquid impermeable backsheet can be obtained by, for example, melt-extruding a thermoplastic resin containing an organic or inorganic filler into a film through a T die or a circular die and uniaxially or biaxially stretching the extruded film.

On the side to be brought into contact with underwear are provided with a pair of adhesive bands 4 along the longitudinal direction. Adhesive bands 4 are protected by a release paper 5 before use. In FIG. 12, reference numeral 6 indicates joints at which the above-mentioned members are bonded together. Other undescribed particulars are the same as in conventional sanitary napkins.

The characteristics of the absorbent article according to the first embodiment are explained below.

The sanitary napkin 100 according to the first embodiment has a liquid retentive absorbent member 2 which includes the first absorbent sheet 10 containing at least the hydrophilic fine fibers and the thermally fusible bonding fibers or the strengthening assistant, and the superabsorbent polymer.

The use of the first absorbent sheet provides an absorbent article which suffers neither fall-off of the superabsorbent polymer nor gel blocking of the superabsorbent polymer. Further, since the absorbent sheet combines functions of liquid absorption, permeation, diffusion and retention, there is no need to combine members having these functions separately as done in the conventional absorbent articles. Therefore, an extremely thin absorbent article which gives a comfortable feeling during the use can be obtained. The thickness of the absorbent article equals to the thickness of the absorbent sheet (0.3 to 0.5 mm) to which the thicknesses of the liquid permeable topsheet, the liquid impermeable backsheet (for example, 0.2 to 1.0 mm) and other elements, if necessary, are added, and therefore the absorbent article has an unexpected ultrathin thickness.

By using an absorbent sheet which comprises the super absorbent particles, and the fiber structure comprising the bulky hydrophilic bulky cellulose fibers and the thermally fusible bonding fibers or the strengthening assistant, the superabsorbent polymer articles being not present on an absorbent surface of the absorbent sheet for absorbing the liquid but distributed inside and fixed to the fiber structure; and the absorbent sheet having a thickness of 0.3 to 1.5 mm, and the superabsorbent polymer particle being spread at an amount of 20 to 70 g per 1 $m^2$ of the absorbent sheet, the thickness of the absorbent article, in particular, is made very small. Also, the absorbent article, during usage, does not give uncomfortable feeling even after, as well as before, the superabsorbent polymer absorbs liquid and swells. This is because the absorbent sheet itself has a very small thickness and its thickness increases little even after the sheet absorbs liquid.

In the preferred embodiment shown in FIG. 12, liquid having passed through the topsheet 1 is absorbed into the inside of napkin 100. Then, liquid passes through the fluff pulp 2a and absorbed and retained in the superabsorbent polymer dispersed in the first absorbent sheet 10. The first absorbent sheet 10 is preferably set in such a manner that the fiber aggregate having an absorbent surface faces the side of the topsheet 1, whereby the liquid absorbed in fluff pulp 2a can be smoothly led to the inside of the first absorbent sheet 10.

As has been explained, in the first absorbent sheet 10, the absorbent polymer is securely fixed without impairing the absorption property inherent in the superabsorbent polymer. Accordingly, the sanitary napkin 100 containing the first absorbent sheet 10 has a high liquid retention capacity. Because the sanitary napkin 100 contains the fluff pulp 2a in addition to the first absorbent sheet 10, the liquid retention capacity is so much increased. The absorbent article of this embodiment is suitable for a sanitary napkin for overnight use, which is worn for a long time.

Second to sixth preferred embodiments of the absorbent article of the present invention are shown in FIGS. 13 through 17. While the particulars common to the first embodiment are not described, the corresponding explanation given to the first embodiment applies thereto appropriately. The same reference numerals as used in FIG. 12 are used for the same members of FIGS. 13 to 17.

Figure 13:
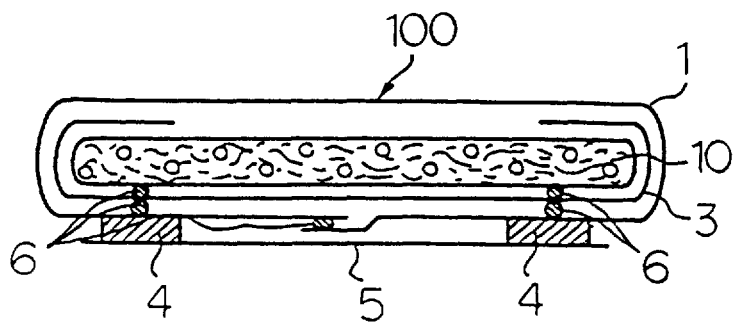
FIG. 13 is a schematic view illustrating the transverse section of a sanitary napkin as a second preferred embodiment of the absorbent article according to the present invention.

In the second preferred embodiment of the absorbent article according to the present invention shown in FIG. 13, the absorbent member of the sanitary napkin 100 consists solely of the first absorbent sheet 10. Both the sides and the bottom of the first absorbent sheet 10 are covered with the backsheet 3. All the surfaces of the combination of the first absorbent sheet 10 and the backsheet 3 are covered with the topsheet 1. Similarly to the first embodiment, the first absorbent sheet 10 is preferably set with the fiber aggregate thereof, which has an absorbent surface, facing the side of the topsheet 1.

The sanitary napkin 100 of this type can be designed so as to have an extremely small thickness because it is composed of fewer members, each of which is thin. And yet it has a large liquid retention capacity despite its thinness because the superabsorbent polymer is securely fixed in the first absorbent sheet 10 without impairing the absorption property inherent in the superabsorbent polymer. Therefore, this embodiment provides a sanitary napkin having a high liquid retention capacity with a comfortable feel.

Figure 14:
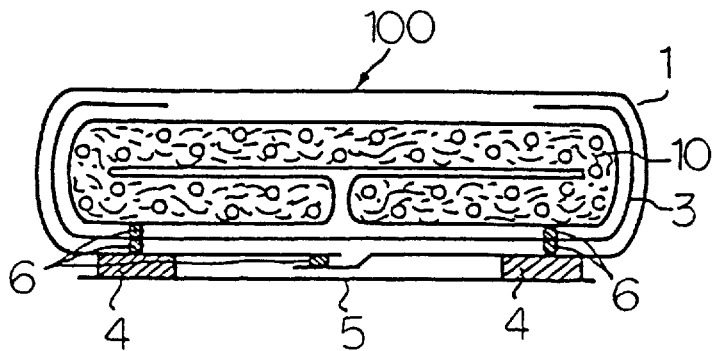
FIG. 14 is a schematic view illustrating the transverse section of a sanitary napkin as a third preferred embodiment of the absorbent article according to the present invention.

According to the third preferred embodiment shown in FIG. 14, the absorbent member of the sanitary napkin 100 consists solely of first absorbent sheet folded in C-shape. Both the sides and the bottom of the first absorbent sheet 10 are covered with the backsheet 3, and all the surfaces of the combination of the first absorbent sheet 10 and the backsheet 3 are covered with the topsheet 1. In this embodiment, it is preferable to set the first absorbent sheet 10 folded in C-shape in such a manner that the fiber aggregate having an absorbent surface faces outside.

The sanitary napkin 100 of the third embodiment is thicker than that shown in FIG. 13 because first absorbent sheet is folded in C-shape and yet can be made thinner than the sanitary napkin shown in FIG. 12 which contains fluff pulp in the absorbent member 2. Further, a high liquid retention capacity is assured because of the C-shape. The third embodiment thus provides a sanitary napkin having a high liquid retention capacity with a comfortable feel.

Figure 15:
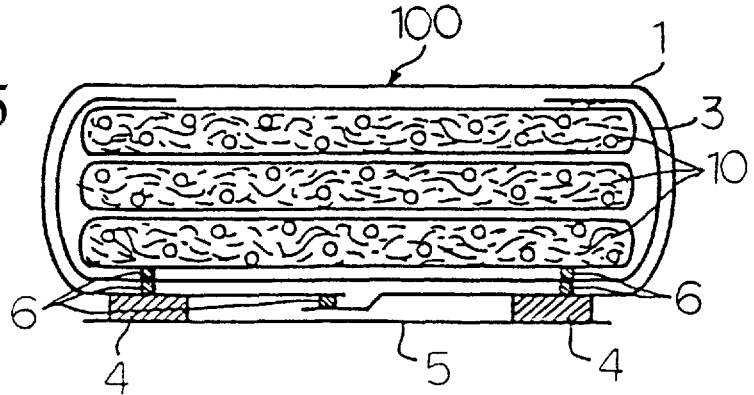
FIG. 15 is a schematic view illustrating the transverse section of a sanitary napkin as a fourth preferred embodiment of the absorbent article according to the present invention.

In a sanitary napkin 100 shown in FIG. 15, as a fourth preferred embodiment of the absorbent article of the present invention, the absorbent member of the sanitary napkin 100 is composed of a plurality of first absorbent sheets 10, 10, ... piled one on the other (three sheets in FIG. 15). The backsheet 3 covers the sides and the back of the pile, and the topsheet 1 covers all the surfaces of the pile and the backsheet 3. Similarly to the first embodiment, each the first absorbent sheet 10 is preferably set with its fiber aggregate having an absorbent surface facing to the side of the topsheet 1.

The sanitary napkin 100 of the third embodiment is thicker than that shown in FIG. 13 because of use of a plurality of first absorbent sheets thus piled and yet can be made thinner than the sanitary napkin shown in FIG. 12 which contains fluff pulp in the absorbent member 2. Further, a high liquid retention capacity is assured by using a plurality of first absorbent sheets 10 thus piled. The fourth embodiment thus provides a sanitary napkin having a high liquid retention capacity with a comfortable feel.

Figure 16:
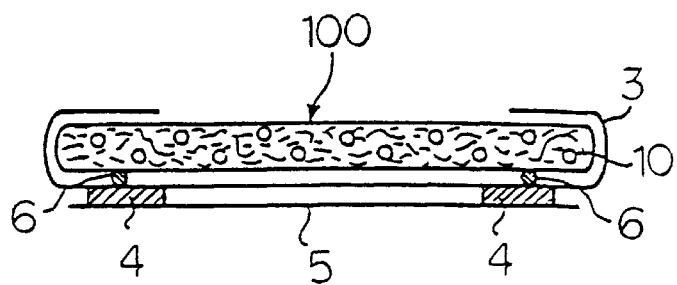
FIG. 16 is a schematic view illustrating the transverse section of a sanitary napkin as a fifth preferred embodiment of the absorbent article according to the present invention.

According to the fifth preferred embodiment shown in FIG. 16, the first absorbent sheet 10 serves as a liquid permeable topsheet and a liquid retentive absorbent member. That is, the sanitary napkin 100 of this embodiment contains the first absorbent sheet 10 as a unitary body serving as a liquid permeable topsheet and a liquid retentive absorbent member, and both the sides and the bottom of the first absorbent sheet 10 are covered with the backsheet 3. In this embodiment, the first absorbent sheet 10 is preferably set with its fiber aggregate having an absorbent surface on the side to be in contact with the body.

This type of the sanitary napkin 100 can be designed so as to have a further reduced thickness because it is composed of only a few members. Therefore, the fifth embodiment makes it possible to provide a sanitary napkin with a comfortable feel through a simple process and at a low cost.

Figure 17:
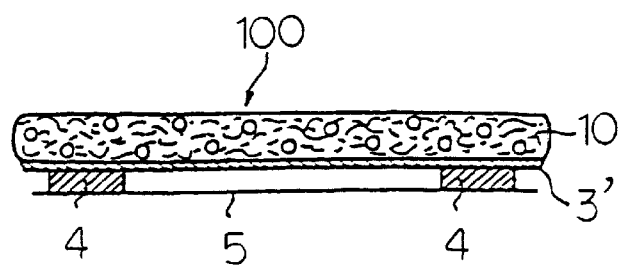
FIG. 17 is a schematic view illustrating the transverse section of a sanitary napkin as a sixth preferred embodiment of the absorbent article according to the present invention.

According to the sixth preferred embodiment shown in FIG. 17, the first absorbent sheet 10 serves for three functions, i.e., as a liquid permeable topsheet, a liquid retentive absorbent member, and a liquid impermeable backsheet. That is, the sanitary napkin 100 of this embodiment has a unitary structure in which a liquid permeable topsheet, a liquid retentive absorbent member, and a liquid impermeable backsheet are integrated. In more detail, the sanitary napkin 100 comprises a liquid impermeable sheet 3' bonded to the side opposite to the side from which liquid is to be absorbed and the first absorbent sheet 10. It is particularly preferable that the first absorbent sheet 10 be set such that the fiber aggregate having the absorbent surface is positioned on the side from which liquid is to be absorbed, and liquid impermeable sheet 3' be bonded to the side opposite to the absorbent surface.

This type of the sanitary napkin 100 can be designed so as to have a further reduced thickness because it is composed of only a few members. Therefore, the sixth embodiment makes it possible to provide a sanitary napkin with a comfortable feel through a further simplified process and at a lower cost. The sixth embodiment is suitable as an absorbent article for absorption of a small amount of liquid, such as nursing breast pads or hygienic pads, as well as sanitary napkins.

Next, another group of preferred embodiments of the absorbent article according to the present invention is described.

Another group of preferred embodiments of the absorbent article according to the present invention are those illustrated above as the first to sixth embodiments (FIGS. 12 to 17) in which the first absorbent sheet 10 is replaced with each of the second to sixth absorbent sheets. The explanation given to the above absorbent articles and the descriptions of FIGS. 12 to 17 appropriately apply to the another group of preferred embodiments.

While the absorbent articles of the present invention have been described by referring to sanitary napkins as a particular example, these absorbent articles can also be used as other absorbent articles, such as hygienic pads, disposable diapers, medical pads, and nursing breast pads, and the like. If desired, a deodorizer, a bactericidal agent, and the like may be incorporated into the absorbent sheet to impart additional functions to the absorbent articles. Further, various changes and modifications can be made in the constituting elements of the absorbent articles and the processes for producing the absorbent articles without departing from the scope of the present invention.

EXAMPLES

The present invention will now be illustrated in greater detail by way of Examples and Comparative Examples, but it is a matter of course that the present invention is not limited to these examples.

Processes for preparing bulky cellulose fibers and hydrophilic fine fibers or particles which can be used in the following Examples and Comparative Examples are shown below. Unless otherwise indicated, all the parts and percents are given by weight.

Preparation Example 1

Preparation of Bulky Cellulose Fibers

One hundred grams of mercerized pulp having an average fiber length of 2.35 mm, a degree of fiber roughness of 0.36 mg/m, and a degree of fiber roundness in the fiber cross section of 0.80 ("Porosanier-J", produced by ITT Rayonier Inc.) were dispersed in 1000 g of an aqueous solution containing 5% dimethylolhydroxyethyleneurea (crosslinking agent "Sumitex Resin NS-19" produced by Sumitomo Chemical Co., Ltd.) and 3% metal salt catalyst ("Sumitex Accelerator X-110" produced by Sumitomo Chemical Co., Ltd.) thereby to impregnate the mercerized pulp with the crosslinking agent.

The crosslinking agent aqueous solution was removed from the mercerized pulp until the amount of the crosslinking agent aqueous solution was reduced to 200% based on the mercerized pulp. The mercerized pulp was heated in an electric dryer at 135° C. for 10 minutes to crosslink the cellulose in the mercerized pulp to obtain crosslinked mercerized pulp (designated cellulose fibers (A)).

Preparation Example 2

Preparation of Bulky Cellulose Fibers

Crosslinked pulp having an average fiber length of 2.38 mm, a degree of fiber roughness of 0.32 mg/m, and a degree of fiber roundness in the fiber cross section of 0.30 ("High Bulk Additive HBA-S" produced by Weyerhauser Paper Co.) was prepared (designated cellulose fibers (B)).

Preparation Example 3

Preparation of Bulky Cellulose Fibers

Mercerized pulp having an average fiber length of 2.35 mm, a degree of fiber roughness of 0.36 mg/m, and a degree of fiber roundness in the fiber cross section of 0.80 ("Porosanier-J" produced by ITT Rayonier Inc.) was prepared (designated cellulose fibers (C)). The cellulose fibers (C) are non-crosslinked fibers.

Preparation Example 4

Preparation of Bulky Cellulose Fibers

Softwood kraft pulp having an average fiber length of 2.56 mm, a degree of fiber roughness of 0.24 mg/m, and a degree of fiber roundness in the fiber cross section of 0.34

("Harmac-R" produced by MacMillan Bloedel Ltd.) was prepared (designated cellulose fibers (D)). The cellulose fibers (D) are non-crosslinked fibers.

Preparation Example 5

Preparation of Bulky Cellulose Fibers

Softwood kraft pulp having an average fiber length of 2.56 mm, a degree of fiber roughness of 0.35 mg/m, and a degree of fiber roundness in the fiber cross section of 0.28 ("Indorayon" produced by PT Inti Indorayon Utama) was prepared (designated cellulose fibers (E)). Cellulose fibers (E) are non-crosslinked fibers.

Preparation Example 6

Preparation of Crosslinked Cellulose Fibers

Crosslinked pulp was prepared in the same manner as in Preparation Example 1, except for using hardwood kraft pulp having a degree of fiber roughness of 0.13 mg/m and a degree of fiber roundness in the fiber cross section of 0.35 ("Bahia Sul Cellulose SA" produced by Bahia Sul Co.) (designated cellulose fibers (F)).

The average fiber length, the degree of roughness, and the degree of fiber roundness in the fiber cross section of cellulose fibers (A) to (F) were measured in accordance with the methods described below.

Measurement of Average Fiber Length and Degree of Fiber Roughness

Measurement was made with a fiber roughness meter FS-200 manufactured by Kajaani Electronics Ltd. In order to measure the true weight of cellulose fibers, cellulose fibers are dried in a vacuum dryer at 100° C. for 1 hour to remove the water content.

Immediately thereafter, about 1 g of the cellulose fibers is weighed out to a precision of ±0.1 mg and completely disaggregated in 150 ml of water by means of a mixer attached to the fiber roughness meter. The suspension is diluted with water to make 5000 ml. A 50 ml aliquot of the diluted suspension is precisely measured out as a sample solution for measurement of the degree of fiber roughness. The average fiber length and the degree of fiber roughness are determined according to the operating procedure of the fiber roughness meter. The average fiber length is obtained from the following formula:

$$\text{Average Fiber Length} = \frac{\sum_{i=1}^{n} n_i l_i^2}{\sum_{i=1}^{n} n_i l_i}$$

wherein $n_i$ is the number of fibers having fiber length $l_i$; and $l_i$ is a fiber length.

Measurement of Degree of Fiber Roundness in Fiber Cross Section

The degree of fiber roundness in the fiber cross section of a cellulose fiber is obtained as follows. A cellulose fiber is transversely sliced with care not to change the sectional area, and an electron micrograph of the section is taken. The micrograph is analyzed by an image analyzer ("Avio EXCEL" manufactured by Nippon Avionics Co., Ltd.) to obtain a degree of fiber roundness in the fiber cross section according to the following formula. Measurement is made on arbitrarily chosen 100 points to obtain the average.

$$\text{Degree of fiber roundness in fiber cross section} = \frac{4 \times \pi \times (\text{Sectional area of a fiber})}{(\text{Circumference of the section of thr fiber})^2}$$

Preparation Example 7

Preparation of Hydrophilic Fine Fibers

Crosslinked hydrophilic fine fibers were prepared in the same manner as in Preparation Example 1, except for using cellulose fibers having an average fiber length of 0.12 mm and a degree of fiber roughness of 0.09 mg/m, and a degree of fiber roundness in the fiber cross section of 0.31 ("KC Flock W-100" produced by Sanyo-Kokusaku Pulp Co., Ltd.) which were obtained by hydrolyzing carefully selected pulp with an acid, washing with water, drying, and mechanically grinding into fine fibers. The resulting fibers were designated hydrophilic fine fibers (G).

Preparation Example 8

Preparation of Hydrophilic Fine Fibers

Cellulose fibers having an average fiber length of 0.12 mm and a degree of fiber roughness of 0.09 mg/m, and a degree of fiber roundness in the fiber cross section of 0.32 ("KC Flock W-100" produced by Sanyo-Kokusaku Pulp Co., Ltd.), designated hydrophilic fine fibers (H), were prepared. Hydrophilic fine fibers (H) is a product obtained by hydrolyzing carefully selected pulp with an acid, washing with water, drying, and mechanically grinding into fine fibers. Hydrophilic fine fibers (H) are non-crosslinked fibers.

Preparation Example 9

Preparation of Hydrophilic Fine Fibers

Softwood kraft pulp having a degree of fiber roughness of 0.18 mg/m, and a degree of fiber roundness in the fiber cross section of 0.32 ("Skeena Prime" produced by Skeena Cellulose Co.) was prepared (designated hydrophilic fine fibers (I)).

Example 1

Preparation of Absorbent Sheet

In water were dispersed chemical pulp (soft wood kraft pulp, SKEENA PRIME produced by Skena Cellulose Co.) having a degree of fiber roughness of 0.18 mg/m and a degree of fiber roundness in the fiber cross section of 0.32 and 1 part by weight (solid content) of a strengthening assistant (polyamide epichlorohydrin resin, Kaimen WS-570 produced by Nippon PMC, Co.) per 100 parts by weight of dried pulp. The dispersed mixture was formed into a fiber web having 40 g/m² (solid content) at the forming part of the wet paper forming machine. Then, the fiber web was dehydrated at a suction box to the extent that the water content is made to 200 parts by weight based on 100 parts by weight of dried fiber web. Thereafter, a superabsorbent polymer (Polymer Q produced by Kao Co.) was spread substantially uniformly on the fiber web at amount of 50 g/m².

On the surface of the fiber web carrying thereon the spread superabsorbent polymer were overlaid an absorbent sheet, serving as the fiber aggregate, which had been previously prepared and had the same composition as the fiber web. The overlaid combination of the fiber web and the absorbent sheet was introduced into a dryer to dry the overlaid combination at 130° C. so as to form the combination into a unitary body. In this way, absorbent sheet (A) incorporating a superabsorbent polymer fixed therein was prepared.

Example 2

Preparation of Absorbent Sheet

In water were dispersed 95 parts of cellulose fibers (C) and 5 parts of polyvinyl alcohol fibers having a fineness of 1 denier and a fiber length of 3 mm (thermally fusible bonding fibers "Fibribond" produced by Sansyo K.K., hereinafter referred to as PVA fibers) in a prescribed concentration. The resulting dispersion was formed into a fiber web having a dry basis weight of 40 g/m$^2$ in a forming part of a wet paper making machine. The fiber web was dehydrated in a suction box to have a water content of 150 parts per 100 parts of the web on a dry basis. A superabsorbent polymer ("Polymer Q" produced by Kao Corp.) was spread substantially uniformly over the dehydrated and still wet fiber web in an amount of 50 g/m$^2$ in immediate front of a press part.

As a fiber aggregate, previously prepared absorbent paper having the same composition as the fiber web and a basis weight of 40 g/m$^2$ was overlaid on the superabsorbent polymer-spread side of the fiber web. The laminate composed of the fiber web and absorbent paper was led to a dryer, where it was dried at 130° C. and formed into a unitary body, thereby to obtain an absorbent sheet having fixed therein the superabsorbent polymer. The resulting absorbent sheet is designated as sheet (B).

Example 3

Preparation of Absorbent Sheet

In water were dispersed 70 parts of cellulose fibers (B), 30 parts of hydrophilic fine fibers (I) and 1 part by weight (solid content) of a strengthening assistant in solid content (polyamide epichlorohydrin resin, Kaimen WS-570 produced by Nippon PMC, Ltd.) per 100 parts by weight of the mixed dry pulp in a prescribed concentration. The resulting dispersion was formed into a fiber web having a dry basis weight of 40 g/m$^2$ in a forming part of a wet paper making machine. The fiber web was dehydrated in a suction box to have a water content of 100 parts per 100 parts of the web on a dry basis. A superabsorbent polymer ("Polymer Q" produced by Kao Corp.) was spread substantially uniformly over the dehydrated and still wet fiber web in an amount of 50 g/m$^2$ in immediate front of a press part.

As a fiber aggregate, previously prepared absorbent paper having the same composition as the fiber web and a basis weight of 40 g/m$^2$ was overlaid on the superabsorbent polymer-spread side of the fiber web. The laminate composed of the fiber web and absorbent paper was led to a dryer, where it was dried at 130° C. and formed into a unitary body, thereby to obtain an absorbent sheet having fixed therein the superabsorbent polymer. The resulting absorbent sheet is designated as sheet (C).

Example 4

Preparation of Absorbent Sheet

In water were dispersed 95 parts of cellulose fibers (B) and 5 parts of PVA fibers in a prescribed concentration. The resulting dispersion was formed into a fiber web having a dry basis weight of 40 g/m$^2$ in a forming part of a wet paper making machine. The fiber web was dehydrated in a suction box to have a water content of 100 parts per 100 parts of the web on a dry basis. A superabsorbent polymer ("Polymer Q" produced by Kao Corp.) was spread substantially uniformly over the dehydrated and still wet fiber web in an amount of 50 g/m$^2$ in immediate front of a press part.

As a fiber aggregate, previously prepared absorbent paper having the same composition as the fiber web and a basis weight of 40 g/m$^2$ was overlaid on the superabsorbent polymer-spread side of the fiber web. The laminate composed of the fiber web and absorbent paper was led to a dryer, where it was dried at 130° C. and formed into a unitary body, thereby to obtain an absorbent sheet having fixed therein the superabsorbent polymer. The resulting absorbent sheet is designated as sheet (D).

Example 5

Preparation of Absorbent Sheet

In water were dispersed 90 parts of cellulose fibers (B) and 10 parts of low-boiling polyester fibers having a fineness of 1.1 denier and a fiber length of 5 mm (thermally fusible bonding fibers "TM-07N" produced by Teijin Ltd., hereinafter simply referred to as polyester fibers) in a prescribed concentration. The resulting dispersion was formed into a fiber web having a dry basis weight of 40 g/m$^2$ in a forming part of a wet paper making machine. The fiber web was dehydrated in a suction box to have a water content of 100 parts per 100 parts of the web on a dry basis. A superabsorbent polymer ("Polymer Q" produced by Kao Corp.) was spread substantially uniformly over the dehydrated and still wet fiber web in an amount of 50 g/m$^2$ in immediate front of a press part.

On the superabsorbent polymer-spread side of the fiber web was overlaid dry processed heat adhesive nonwoven fabric (basis weight: 40 g/m$^2$) which was prepared by carding polyethylene/polypropylene conjugate fibers having a fineness of 2.2 denier and a fiber length of 38 mm and having been subjected to a surface treatment for rendering hydrophilic (a product of Chisso Corp.). The laminate composed of the fiber web and nonwoven fabric was led to a dryer, where it was dried at 130° C. and formed into a unitary body, thereby to obtain an absorbent sheet having fixed therein the superabsorbent polymer. The resulting absorbent sheet is designated as sheet (E).

Example 6

Preparation of Absorbent Sheet

In water were dispersed 60 parts of cellulose fibers (B), 35 parts of hydrophilic fine fibers (I), and 5 parts of polyethylene terephthalate fibers having a fineness of 1.1 denier and an average fiber length of 5 mm (thermally fusible bonding fibers "TMOTNSB" produced by Teijin Ltd., hereinafter referred to as PET fibers), and the slurry was formed into a diffusing layer on the wire of a first paper making machine.

Separately, 95 parts of cellulose fibers (B) and 5 parts of PET fibers were dispersed in water, and a permeable layer was formed on the wire of a second paper making machine by using the slurry.

The diffusing layer and the permeable layer were each removed from the wire and laminated one on the other to prepare composite absorbent paper as a fiber web. The fiber web thus formed had a total basis weight of 70 g/m$^2$ on a dry basis, in which each of the diffusing layer and the permeable layer had a basis weight of 35 g/m$^2$. The fiber web had such a gradient in liquid diffusion as to exhibit high liquid permeability in its permeable layer side and high liquid diffusing properties in its diffusing layer side.

The fiber web was dehydrated in a suction box so as to have a water content of 200 parts per 100 parts of the fiber web on a dry basis. Subsequently, and in immediate front of a press part, a superabsorbent polymer ("Aquaric CAW-4" produced by Nippon Shokubai Kagaku Kogyo Co., Ltd.) was spread substantially uniformly on the permeable layer of the dehydrated wet fiber web at a rate of 50 g/m$^2$.

A fiber web having a basis weight of 30 g/m$^2$ which had previously been prepared according to the following formulation was overlaid on the superabsorbent polymer-spread side of the fiber web. The laminate of the fiber web and the fiber aggregate was led to a dryer, where it was dried at 130° C. and formed into a unitary body to obtain an absorbent sheet having fixed therein the superabsorbent polymer as shown in FIG. 3. The resulting absorbent sheet is designated absorbent sheet (F).

The fiber aggregate used was prepared as follows. The cellulose fibers (A) and PET fibers were uniformly dispersed in water in a concentration of 0.19% and 0.01%, respectively, to prepare a 0.2% slurry. The slurry was spread over the wire having an opening size of 90 μm (166 mesh) of a paper making machine to form a paper layer on the wire. The paper layer was dehydrated and dried in a suction box at a rate of 6 ml/[cm$^2$·sec] to obtain a fiber aggregate having a basis weight of 30 g/m$^2$. The resulting fiber aggregate contained 95 parts of cellulose fibers (A) and 5 parts of PET fibers per 100 parts of the fiber aggregate.

Example 7

Preparation of Absorbent Sheet

An absorbent sheet (designated absorbent sheet (G) was prepared in the same manner as in Example 6, except for forming a diffusing layer from 70 parts of cellulose fibers (C), 25 parts of hydrophilic fine fibers (I), and 5 parts of PVA fibers, a permeable layer from 95 parts of cellulose fibers (C) and 5 parts of PVA fibers, and a fiber aggregate from 97 parts of cellulose fibers (A) and 3 parts of PVA fibers.

Example 8

Preparation of Absorbent Sheet

Cellulose fibers (B) and PET fibers were uniformly dispersed in water in a concentration of 0.19% and 0.01%, respectively, to prepare a 0.2% slurry. The slurry was spread on the wire having an opening size of 90 μm (166 mesh) of a paper making machine to form a paper layer on the wire. The paper layer was dehydrated in a suction box at a rate of 6 ml/[cm$^2$·sec] to obtain a fiber web having a dry basis weight of 30 g/m$^2$. The resulting fiber web contained 95 parts of cellulose fibers (B) and 5 parts of PET fibers per 100 parts of the fiber web.

The fiber web was dehydrated in a suction box to have a water content of 200 parts per 100 parts of the web on a dry basis. Subsequently and in immediate front of a press part, a superabsorbent polymer (Aquaric CAW-4, produced by Nippon Shokubai Kagaku Kogyo K.K.) was spread substantially uniformly over the dehydrated and still wet fiber web at a rate of 50 g/m$^2$.

A fiber aggregate having a basis weight of 70 g/m$^2$ which had been previously prepared according to the following formulation was overlaid on the superabsorbent polymer-spread side of the fiber web in such a manner that the fiber web was brought into contact with the diffusing layer (hereinafter described) of the fiber aggregate. The laminate composed of the fiber web and absorbent paper was led to a dryer, where it was dried at 130° C. and formed into a unitary body, thereby to obtain an absorbent sheet having fixed therein the superabsorbent polymer. The resulting absorbent sheet is designated as sheet (H).

The fiber aggregate used above was composite absorbent paper composed of a permeable layer and a diffusing layer, which was prepared as follows.

In water were dispersed 95 parts of cellulose fibers (C) and 5 parts of PET fibers, and a diffusing layer was formed on the wire of a first paper making machine by using the slurry.

Separately, 70 parts of cellulose fibers (C), 25 parts of hydrophilic fine fibers (I), and 5 parts of PET fibers were dispersed in water, and a permeable layer was formed on the wire of a second paper making machine by using the slurry.

The diffusing layer and the permeable layer were each removed from the wire and laminated one on the other to prepare a composite absorbent paper as a fiber aggregate. The fiber aggregate thus formed had a total basis weight of 70 g/m$^2$, in which each of the diffusing layer and the permeable layer had a basis weight of 35 g/m$^2$. The fiber aggregate had such a gradient in liquid diffusion as exhibited high liquid permeability in its permeable layer side and high liquid diffusing properties in its diffusing layer side.

Example 9

Preparation of Absorbent Sheet

Cellulose fibers (A), hydrophilic fine fibers (H), and PVA fibers were uniformly dispersed in water in a concentration of 0.16%, 0.03%, and 0.01%, respectively, to prepare a 0.2% slurry.

The slurry was spread on the wire having an opening size of 90 μm (166 mesh) of a paper making machine to form a paper layer on the wire. The paper layer was dehydrated in a suction box at a rate of 6 ml/[cm$^2$·sec] to obtain a fiber web having a basis weight of 70 g/m$^2$.

The resulting fiber web contained 80 parts of cellulose fibers (A), 15 parts of hydrophilic fine fibers (H), and 5 parts of PVA fibers per 100 parts of the fiber web. The proportion of hydrophilic fine fibers (H) was higher in one side of the fiber web than in the other side so that the fiber web showed such a gradient in liquid diffusion as exhibited high diffusion in the side with a high proportion of hydrophilic fine fibers (H) and low diffusion in the opposite side.

The fiber web was dehydrated in a suction box so as to have a water content of 200 parts per 100 parts of the web on a dry basis. A superabsorbent polymer (Aquaric CAW-4, produced by Nippon Shokubai Kagaku Kogyo K.K.) was spread substantially uniformly over the side having a lower proportion of hydrophilic fine fibers (H) of the dehydrated and still wet fiber web at a rate of 50 g/m$^2$.

A fiber aggregate having a basis weight of 30 g/m$^2$ which had been previously prepared according to the following formulation was overlaid on the superabsorbent polymer-spread side of the fiber web. The laminate composed of the fiber web and the fiber aggregate was led to a dryer, where it was dried at 130° C. and formed into a unitary body, thereby to obtain an absorbent sheet having fixed therein the superabsorbent polymer. The resulting absorbent sheet is designated as sheet (I).

The fiber aggregate used above was prepared as follows. Cellulose fibers (A) and PVA fibers were uniformly dispersed in water in a concentration of 0.194% and 0.006%, respectively, to prepare a 0.2% slurry. The slurry was spread on a paper making wire having an opening size of 90 µm (166 mesh) to form a paper layer on the wire. The paper layer was dehydrated and dried in a suction box at a rate of 6 ml/[cm²·sec] to obtain a fiber aggregate having a basis weight of 30 g/m². The resulting fiber aggregate contained 97 parts of cellulose fibers (A) and 3 parts of PVA fibers per 100 parts of the fiber aggregate.

Example 10

Preparation of Absorbent Sheet

Cellulose fibers (B) and PVA fibers were uniformly dispersed in water in a concentration of 0.194% and 0.006%, respectively, to prepare a 0.2% slurry. The slurry was spread on a paper making wire having an opening size of 90 µm (166 mesh) to form a paper layer on the wire. The paper layer was dehydrated in a suction box at a rate of 6 ml/[cm²·sec] to obtain a fiber web having a basis weight of 30 g/m². The resulting fiber web contained 97 parts of cellulose fibers (B) and 3 parts of PVA fibers per 100 parts of the fiber web.

The fiber web was dehydrated in the suction box so as to have a water content of 200 parts per 100 parts of the fiber web on a dry basis.

Subsequently and immediately in front of a press part, a superabsorbent polymer ("Aquaric CAW-4" produced by Nippon Shokubai Kagaku Kogyo Co., Ltd.) was spread substantially uniformly over the dehydrated and wet fiber web at a rate of 50 g/m².

A fiber aggregate having a basis weight of 70 g/m² which had been previously prepared according to the following formulation was overlaid on the superabsorbent polymer-spread side of the fiber web. The laminate composed of the fiber web and the fiber aggregate was led to a dryer, where it was dried at 130° C. and formed into a unitary body, thereby to obtain an absorbent sheet having fixed therein the superabsorbent polymer. The resulting absorbent sheet is designated as sheet (J).

The fiber aggregate used above was prepared as follows. Cellulose fibers (A), hydrophilic fine fibers (H), and PVA fibers were uniformly dispersed in water in a concentration of 0.16%, 0.03%, and 0.01%, respectively, to prepare a 0.2% slurry.

The slurry was spread on a paper making wire having an opening size of 90 µm (166 mesh) to form a paper layer on the wire. The paper layer was dehydrated and dried in a suction box at a rate of 6 ml/[cm²·sec] to obtain a fiber aggregate having a basis weight of 70 g/m². 682[0185]

The resulting fiber aggregate contained 80 parts of cellulose fibers (A), 15 parts of hydrophilic fine fibers (H), and 5 parts of PVA fibers per 100 parts of the fiber aggregate. The proportion of hydrophilic fine fibers (H) was higher in one side of the fiber aggregate than in the other side so that the fiber aggregate showed such a gradient in liquid diffusion as exhibited high diffusion in the side with a high proportion of hydrophilic fine fibers (H) and low diffusion in the opposite side.

Example 11

Preparation of Absorbent Sheet

In water were dispersed 95 parts of cellulose fibers (A) and 5 parts of PVA fibers in prescribed concentrations. A fiber web having a dry basis weight of 70 g/m² was formed from the slurry in the forming part of a wet paper making machine. The fiber web was dehydrated in the suction box so as to have a water content of 150 parts per 100 parts of the fiber web on a dry basis. In immediately front of the press part, hydrophilic fine fibers (G) were spread on the dehydrated wet fiber web substantially uniformly at a rate of 20 g/m², and a superabsorbent polymer ("Aquaric CAW-4" produced by Nippon Shokubai Kagaku Kogyo Co., Ltd.) was further spread thereon substantially uniformly at a rate of 50 g/m².

Previously prepared absorbent paper having the same composition as the above fiber web and having a basis weight of 30 g/m² was overlaid on the side of the fiber web on which hydrophilic fine fibers (G) and the superabsorbent polymer had been spread. The laminate of the fiber web and the absorbent paper were led to a dryer and dried at 130° C. to obtain a unitary absorbent sheet having fixed therein hydrophilic fine fibers (G) and the superabsorbent polymer (designated absorbent sheet (K)).

Example 12

Preparation of Absorbent Sheet

In water were dispersed 95 parts of cellulose fibers (B) and 5 parts of the polyester fibers in prescribed concentrations. A fiber web having a dry basis weight of 70 g/m² was formed from the slurry in the forming part of a wet paper making machine. The fiber web was dehydrated in a suction box so as to have a water content of 100 parts per 100 parts of the fiber web on a dry basis. After the fiber web was passed through a press part, hydrophilic fine fibers (G) were spread thereon substantially uniformly at a rate of 20 g/m², and a superabsorbent polymer ("Aquaric CAW-4" produced by Nippon Shokubai Kagaku Kogyo Co., Ltd.) was further spread thereon substantially uniformly at a rate of 50 g/m².

Previously prepared absorbent paper having the same composition as the above fiber web and having a basis weight of 30 g/m² was overlaid on the side of the fiber web on which hydrophilic fine fibers (G) and the superabsorbent polymer had been spread. The laminate of the fiber web and the absorbent paper were led to a dryer and dried at 130° C. to obtain an integrated absorbent sheet having fixed therein hydrophilic fine fibers (G) and the superabsorbent polymer (designated absorbent sheet (L)).

Example 13

Preparation of Absorbent Sheet

An absorbent sheet (designated absorbent sheet (M)) was prepared in the same manner as in Example 12, except that the fiber web and the fiber aggregate were each prepared from 95 parts of cellulose fibers (C) and 5 parts of PVA fibers and that a uniform mixture of hydrophilic fine fibers (H) and the superabsorbent polymer was spread substantially uniformly at a rate of 50 g of each fibers per m².

Example 14

Preparation of Absorbent Sheet

An absorbent sheet (designated absorbent sheet (N)) was prepared in the same manner as in Example 11, except that the fiber web and the fiber aggregate were each prepared from 95 parts of cellulose fibers (D) and 5 parts of polyester fibers and that a uniform mixture of hydrophilic fine fibers (H) and the superabsorbent polymer was spread substantially uniformly at a rate of 50 g of each fibers per m².

Example 15

Preparation of Absorbent Sheet

An absorbent sheet (O) was prepared in the same manner as in Example 11, except that a fiber web and a fiber aggregate were prepared from 60 parts of the cellulose fibers (A), 40 parts of the cellulose fibers (D) and 1 part of a strengthening assistant (polyamide epichlorohydrin resin, Kaimen WS-570), and that a mixture of the hydrophilic fine fibers (H) and the superabsorbent polymer both uniformly mixed was spread at an amount of 50 g/m$^2$, respectively.

Example 16

Preparation of Absorbent Sheet

An absorbent sheet (P) was prepared in the same manner as in Example 11, except that a fiber web and a fiber aggregate were prepared from 95 parts of the cellulose fibers (E) and 5 parts of the polyester fibers, and that a mixture of the hydrophilic fine fibers (H) and the superabsorbent polymer both uniformly mixed was spread at an amount of 50 g/m$^2$, respectively.

Comparative Example 1

Preparation of Absorbent Sheet

An absorbent sheet was prepared as follows using absorbent paper having a basis weight of 40 g/m$^2$ which had been previously prepared from hydrophilic fine fibers (I).

Water was spread on the absorbent paper to give a water content of 200 parts per 100 parts of the dry absorbent paper. A superabsorbent polymer ("Polymer Q" produced by Kao Corp.) was spread on the wetted absorbent paper substantially uniformly at a rate of 50 g/m$^2$.

Absorbent paper having the same composition as the above absorbent paper and having a basis weight of 40 g/m$^2$ was overlaid on the superabsorbent polymer-spread side of the absorbent paper. The laminate of the two sheets of absorbent paper was integrated by pressing and dried in a dryer to obtain an absorbent sheet having a total basis weight of 130 g/m$^2$ (designated absorbent sheet (Q)). The absorbent paper on which the superabsorbent polymer was spread did not have the state of a wet fiber web. That is, the pulp fibers in the absorbent paper were strongly bound to each other. Absorbent sheet (Q) consisted of a pair of sheets of absorbent paper with the superabsorbent polymer sandwiched therebetween in a layer.

Comparative Example 2

Preparation of Absorbent Sheet

Water was spread on the same absorbent paper as used in Comparative Example 1 to give a water content of 100 parts per 100 parts of the absorbent paper on a dry basis. A superabsorbent polymer ("Polymer Q" produced by Kao Corp.) was spread over the wet absorbent paper substantially uniformly at a rate of 50 g/m$^2$.

Absorbent paper having the same composition as the above absorbent paper and having a basis weight of 40 g/m$^2$ was overlaid on the superabsorbent polymer-spread side of the absorbent paper. The laminate was pressed and integrated by passing under an embossing roll having a 5×5 mm lattice pattern and dried in a dryer to obtain an absorbent sheet having a total basis weight of 130 g/m$^2$. The resulting absorbent sheet is designated absorbent sheet (R). The absorbent paper on which the superabsorbent polymer was spread did not have the state of a wet fiber web. That is, the pulp fibers in the absorbent paper were strongly bound to each other. Absorbent sheet (R) consisted of a pair of sheets of absorbent paper with the superabsorbent polymer interposed therebetween by embossing.

Comparative Example 3

Preparation of Absorbent Sheet

An adhesive ("Movinyl 710" produced by Hoechst Gosei K.K.) was applied to the same absorbent paper as used in Comparative Example 1 at a spread of 20 g/m$^2$, and a superabsorbent polymer ("Polymer Q" produced by Kao Corp.) was spread over the adhesive-applied side of the absorbent paper substantially uniformly at a rate of 50 g/m$^2$.

Absorbent paper having the same composition and basis weight as the absorbent paper used above was overlaid on the superabsorbent polymer-spread side of the absorbent paper. The laminate of the two sheets of absorbent paper was integrated by pressing and dried in a dryer to obtain an absorbent sheet having a total basis weight of 150 g/m$^2$ (designated absorbent sheet (S)). The absorbent paper on which the superabsorbent polymer was spread did not have the state of a wet fiber web. That is, the pulp fibers in the absorbent paper were strongly bound to each other. Absorbent sheet (S) consisted of a pair of sheets of absorbent paper with the superabsorbent polymer fixed therebetween in a layer via an adhesive.

Comparative Example 4

Preparation of Absorbent Sheet

An absorbent sheet comprising synthetic pulp and a superabsorbent polymer and having a basis weight of 80 g/m$^2$ was prepared by a dry process as follows.

A pulp sheet (soft wood pulp produced by Hercules, Ltd.) consisting of 25 parts of polyethylene synthetic pulp and 75 parts of chemical pulp was fibrillated by means of a hammer mill, and a superabsorbent polymer ("Aquaric CAW-4" produced by Nippon Shokubai Kagaku Kogyo Co., Ltd.) was mixed therewith in such an amount that the resulting absorbent sheet contained 50 g/m$^2$ of the superabsorbent polymer. The mixture was sheeted and then subjected to hot air treatment, whereby the polyethylene synthetic pulp was fused to provide an unitary body. The resulting dry processed absorbent sheet is designated absorbent sheet (T). Absorbent sheet (T) had the superabsorbent polymer on its surface.

Comparative Example 5

Preparation of Absorbent Sheet

A superabsorbent polymer ("Aquaric CAW-4" produced by Nippon Shokubai Kagaku Kogyo Co., Ltd.) was spread at a rate of 45 g/m$^2$ between a pair of pulp sheets (soft wood pulp produced by Hapix Co., Ltd.) each having a basis weight of 45 g/m$^2$ which were prepared by an air-laid method. The pulp was then fixed with a chemical binder to prepare an absorbent sheet, designated absorbent sheet (V).

Comparative Example 6

Preparation of Absorbent Sheet

Dry composite absorbent paper composed of a permeable layer and a diffusing layer was prepared as a fiber web as follows.

In water were dispersed 60 parts of cellulose fibers (E), 20 parts of hydrophilic fine fibers (I), and 20 parts of PET fibers, and a diffusing layer was formed on the wire of a first paper making machine.

Separately, 95 parts of cellulose fibers (E) and 5 parts of PET fibers were dispersed in water, and a permeable layer was formed on the wire of a second paper making machine.

The diffusing layer and the permeable layer were removed from the wire and laminated one on the other. The laminate was dehydrated and dried to obtain a fiber web. The resulting fiber web was composite absorbent paper composed of the diffusing layer and the permeable layer, but had no diffusion gradient. The diffusing layer and the permeable layer each had a basis weight of 35 g/m², giving the fiber web a total basis weight of 70 g/m².

An adhesive ("Movinyl 710" produced by Hoechst Gosei K.K.) was applied to the permeable layer of the dried fiber web at a spread of 20 g/m², and a superabsorbent polymer ("Aquaric CAW-4" produced by Nippon Shokubai Kagaku Kogyo Co., Ltd.) was spread thereon substantially uniformly at a rate of 50 g/m².

A fiber aggregate having a basis weight of 30 g/m² which had been previously prepared according to the following formulation was overlaid on the superabsorbent polymer-spread side of the fiber web. The laminate was pressed into a unitary body and dried in a dryer at 130° C. to obtain an absorbent sheet having a basis weight of 170 g/m². The resulting absorbent sheet is designated absorbent sheet (V). The fiber web on which the superabsorbent polymer was spread did not have the state of a wet fiber web. That is, the pulp fibers in the absorbent paper were strongly bound to each other. Absorbent sheet (V) consisted of the fiber web and the fiber aggregate with the superabsorbent polymer fixed therebetween in a layer via an adhesive.

The fiber aggregate used above was prepared as follows. Cellulose fibers (E) and PET fibers were uniformly dispersed in water in a concentration of 0.19% and 0.01%, respectively, to prepare a 0.2% slurry. The fiber aggregate was prepared by using the slurry in the same manner as in Example 1. The fiber aggregate contained 95 parts of cellulose fibers (E) and 5 parts of PET fibers per 100 parts of the fiber aggregate.

Comparative Example 7

Preparation of Absorbent Sheet

A dry fiber web was prepared as follows.

Cellulose fibers (D) and PVA fibers were uniformly dispersed in water in a concentration of 0.19% and 0.01%, respectively, to prepare a 0.2% slurry. The slurry was formed into a fiber web having a basis weight of 30 g/m² in the same manner as in Example 7. The resulting fiber web contained 95 parts of cellulose fibers (D) and 5 parts of PVA fibers per 100 parts of the fiber web.

Water was supplied on the resulting fiber web to give a water content of 10 parts per 100 parts of the fiber web on a dry basis. A superabsorbent polymer ("Aquaric CAW-4" produced by Nippon Shokubai Kagaku Kogyo Co., Ltd.) was spread over the wetted fiber web substantially uniformly at a rate of 50 g/m².

A fiber aggregate having a basis weight of 70 g/m² which had been previously prepared according to the following formulation was overlaid on the superabsorbent polymer-spread side of the fiber web in such a manner that the fiber web might be brought into contact with the diffusing layer (hereinafter described) of the fiber aggregate. The laminate of the fiber web and the fiber aggregate was integrated by pressing with an embossing roll having a 5×5 mm lattice pattern and dried in a dryer at 130° C. to obtain an absorbent sheet having a total basis weight of 150 g/m². The resulting absorbent sheet is designated absorbent sheet (W). The fiber web on which the superabsorbent polymer was spread did not have the state of a wet fiber web. That is, the pulp fibers in the fiber web were strongly bound to each other. Absorbent sheet (W) consisted of the fiber web and the fiber aggregate with the superabsorbent polymer pressed therebetween by embossing.

The fiber aggregate used above was composite absorbent paper composed of a permeable layer and a diffusing layer, which was prepared as follows.

In water were dispersed 60 parts of cellulose fibers (D), 35 parts of hydrophilic fine fibers (I), and 5 parts of PVA fibers, and a diffusing layer was formed on the wire of a first paper making machine by using the slurry.

Separately, 95 parts of cellulose fibers (D) and 5 parts of PVA fibers were dispersed in water, and a permeable layer was formed on the wire of a second paper making machine by using the slurry.

The diffusing layer and the permeable layer were removed from the respective wires, laminated one on the other, and dehydrated and dried to prepare a fiber aggregate. The resulting fiber aggregate contained no bulky cellulose fibers and therefore did not have a diffusion gradient.

The fiber aggregate thus formed had a total basis weight of 70 g/m², in which each of the diffusing layer and the permeable layer had a basis weight of 35 g/m².

Comparative Example 8

Preparation of Absorbent Sheet

In water were dispersed 95 parts of cellulose fibers (D) and 5 parts of PVA fibers, and the slurry was formed into paper and dried by means of a paper making machine to prepare absorbent paper having a basis weight of 70 g/m². An absorbent sheet comprising the absorbent paper was prepared by the following process.

Water was spread on the resulting absorbent paper to give a water content of 200 parts per 100 parts of the absorbent paper on a dry basis. A superabsorbent polymer ("Aquaric CAW-4" produced by Nippon Shokubai Kagaku Kogyo Co., Ltd.) was spread over the wetted absorbent paper substantially uniformly at a rate of 50 g/m².

Absorbent paper having the same composition as the above absorbent paper and a basis weight of 30 g/m² was overlaid on the superabsorbent polymer-spread side of the absorbent paper. The laminate of a pair of the sheets of the absorbent paper was integrated by pressing and dried in a dryer to obtain an absorbent sheet having a total basis weight of 150 g/m², designated absorbent sheet (X). The absorbent paper on which the superabsorbent polymer was spread did not have the state of a wet fiber web. That is, the fibers composing the absorbent paper were strongly bound to each other even after wetted. Absorbent sheet (X) consisted of a pair of the sheets of the absorbent paper with the superabsorbent polymer sandwiched therebetween in a layer.

Comparative Example 9

Preparation of Absorbent Sheet

In water were dispersed 95 parts of cellulose fibers (E) and 5 parts of PET fibers, and the slurry was formed into paper and dried by means of a paper making machine to prepare absorbent paper having a basis weight of 70 g/m². An absorbent sheet comprising the absorbent paper was prepared by the following process.

The absorbent paper was coated with an adhesive ("Movinyl 710" produced by Hoechst Gosei K.K.) at a spread of 20 g/m², and a superabsorbent polymer ("Aquaric CAW-4" produced by Nippon Shokubai Kagaku Kogyo Co., Ltd.) was spread thereon substantially uniformly at a rate of 50 g/m².

Absorbent paper having the same composition as the above absorbent paper and a basis weight of 30 g/m² was overlaid on the superabsorbent polymer-spread side of the above absorbent paper. The laminate was pressed into a unitary body and dried in a dryer to obtain an absorbent sheet having a total basis weight of 150 g/m², designated absorbent sheet (Y). The absorbent paper on which the superabsorbent polymer was spread did not have the state of a wet fiber web. That is, the pulp fibers in the absorbent paper were strongly bound to each other. Absorbent sheet (Y) consisted of a pair of the sheets of absorbent paper with the superabsorbent polymer sandwiched therebetween in a layer.

Comparative Example 10

Preparation of Absorbent Sheet

In water were dispersed 95 parts of cellulose fibers (F) and 5 parts of PVA fibers, and the slurry was formed into paper and dried by means of a paper making machine to prepare absorbent paper having a basis weight of 70 g/m². An absorbent sheet comprising the absorbent paper was prepared by the following process.

Water was spread on the resulting absorbent paper to give a water content of 10 parts per 100 parts of the absorbent paper on a dry basis. A superabsorbent polymer ("Aquaric CAW-4" produced by Nippon Shokubai Kagaku Kogyo Co., Ltd.) was spread on the wetted absorbent paper substantially uniformly at a rate of 50 g/m².

Absorbent paper having the same composition as the above absorbent paper and a basis weight of 30 g/m² was overlaid on the superabsorbent polymer-spread side of the absorbent paper. The laminate of a pair of the sheets of the absorbent paper was integrated by pressing under an embossing roll having a 5×5 mm lattice pattern and dried in a dryer to obtain an absorbent sheet having a total basis weight of 150 g/m², designated absorbent sheet (Z). The absorbent paper on which the superabsorbent polymer was spread did not have the state of a wet fiber web. That is, the fibers composing the absorbent paper were strongly bound to each other even after wetted. Absorbent sheet (Z) consisted of a pair of the sheets of such absorbent paper with the superabsorbent polymer sandwiched therebetween in a layer.

Each of the absorbent sheets prepared was tested according to the following test methods. The results obtained are shown in Table 1 below.

Thickness

An absorbent sheet was cut to an appropriate size, a load of 2.5 g/cm² was applied thereon with a loaded area of 10 cm² (a disk having a radius of 17.8 mm), and the thickness of the sheet under the load was measured with a thickness meter. Measurement was made on 10 cut pieces per sample to obtain an average thickness.

Test of Fall-off of Superabsorbent Polymer

A 70×200 mm piece cut out of an absorbent sheet was weighed and put in a 280 mm long and 200 mm wide polyethylene bag with a fastener. Vibration was given to the test piece by shaking the bag 50 times by the hand. The test piece was again weighed to obtain a change in weight. In order to facilitate visual observation of the superabsorbent polymer fallen in the bag, water tinted with Blue No. 1 (0.3 g/100 ml of water) was put into the bag to swell the fallen superabsorbent polymer. The degree of fall-off of the superabsorbent polymer was observed with the naked eye and graded as follows.

Good . . . Fall-off of superabsorbent polymer is hardly observed.

Fair . . . Slight fall-off of superabsorbent polymer is observed.

Poor . . . Considerable fall-off of superabsorbent polymer is observed.

Measurement was made ten times, and a fall-off value was calculated by averaging the measured values.

Wet Strength of Absorbent Sheet

Ten grams of water tinted with Blue No. 1 (0.3 g/100 ml of water) was dropped on a plate and wiped off by hand with a 200 mm×200 mm test piece cut out of an absorbent sheet. The wiping test was repeated three times for each test piece (until 30 g of water was absorbed in the test piece). The surface condition of the test piece and the fall-off of the superabsorbent polymer were examined.

Good . . . The surface of the absorbent sheet does not rip, and the superabsorbent polymer does not fall off.

Fair . . . The surface of the absorbent sheet slightly rips, but the superabsorbent polymer does not fall off.

Poor . . . The surface of the absorbent sheet rips, and the superabsorbent polymer falls off.

Saturated Absorption

A 5 cm square test piece cut out of an absorbent sheet is put in a bag made of nonwoven fabric and soaked in ion-exchanged water for 10 minutes as contained in the bag. The bag was taken out of water, hung in air for 1 hour to let the water drip, and weighed to obtain a weight gain per gram of the sheet as a saturated absorption (g/g).

Rate of Absorption

Figure 18:
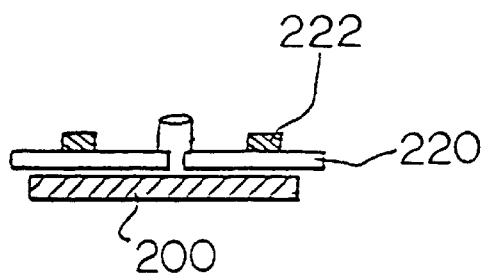
FIG. 18 is a schematic view illustrating measurement of a rate of absorption.

As shown in FIG. 18, 10 cm square transparent acrylic plate 220 having a throughhole of 1 cm in diameter in the center thereof was placed on 15 cm square absorbent sheet 200, and weights 222 were put thereon to apply a load of 5 g/cm² to the absorbent sheet. Twenty milliliters of physiological saline was poured into the sheet through the hole, and the time required for the sheet to absorb physiological saline was measured. One minute later, the same absorption test was repeated to measure the time for re-absorption.

Back-flow

Figure 19:
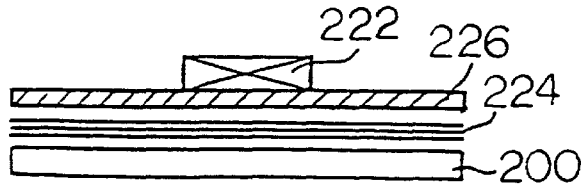
FIG. 19 is a schematic view illustrating measurement of a back-flow.

As shown in FIG. 19, after 10 minutes from the above-described measurement of the rate of absorption, 10 sheets of 15 cm square filter paper 224 (Toyo Filter Paper Type 2) were piled up on the absorbent sheet, and 15 cm square acrylic plate 226 and weight 222 were put thereon to apply a load of 50 g/cm² for 1 minute. Filter paper 224 was removed, and the weight of physiological saline absorbed in filter paper 224 was taken as a back-flow.

TABLE 1

| | Absorbent Sheet | Thickness (mm) | Polymer Fall-off Test | | Wet Strength of Absorbent Sheet | Absorption Performance of Absorbent Sheet | | | |
|---|---|---|---|---|---|---|---|---|---|
| | | | Fall-off (g) | Visual Observation | | Saturated Absorption (g/g) | Rate of Absorption (Absorbing Time) | | Back-flow (g) |
| | | | | | | | First (sec/20 g) | Second (sec/20 g) | |
| Examples | | | | | | | | | |
| 1 | A | 0.56 | ≦0.01 | Good | Good | 75 | 57 | 105 | 0.12 |
| 2 | B | 0.72 | ≦0.01 | Good | Good | 98 | 31 | 60 | 0.08 |
| 3 | C | 0.71 | ≦0.01 | Good | Good | 96 | 26 | 57 | 0.06 |
| 4 | D | 0.82 | ≦0.01 | Good | Good | 100 | 25 | 30 | 0.03 |
| 5 | E | 1.35 | 0.02 | Fair to Good | Good | 85 | 28 | 35 | 0.03 |
| 6 | F | 0.85 | ≦0.01 | Good | Good | 90 | 35 | 45 | 0.06 |
| 7 | G | 0.87 | ≦0.01 | Good | Good | 88 | 38 | 48 | 0.05 |
| 8 | H | 0.85 | ≦0.01 | Good | Good | 93 | 31 | 40 | 0 04 |
| 9 | I | 0.75 | ≦0.01 | Good | Good | 95 | 25 | 35 | 0.06 |
| 10 | J | 0.83 | ≦0.01 | Good | Good | 93 | 26 | 38 | 0.05 |
| 11 | K | 0.72 | ≦0.01 | Good | Good | 105 | 26 | 57 | 0.05 |
| 12 | L | 0.65 | ≦0.01 | Good | Good | 107 | 28 | 58 | 0.06 |
| 13 | M | 0.60 | ≦0.01 | Good | Good | 110 | 29 | 60 | 0.08 |
| 14 | N | 0.58 | ≦0.01 | Good | Good | 112 | 31 | 62 | 0.09 |
| 15 | O | 0.55 | ≦0.01 | Good | Good | 100 | 40 | 85 | 0.10 |
| 16 | P | 0.54 | ≦0.01 | Good | Good | 98 | 45 | 95 | 0.12 |
| Comparative Examples | | | | | | | | | |
| 1 | Q | 0.52 | 0.13 | Poor | Fair | 73 | 158 | 326 | 0.15 |
| 2 | R | 0.71 | 0.21 | Poor | Poor*[1] | 71 | 95 | 218 | 0.18 |
| 3 | S | 0.53 | 0.06 | Fiar | Good | 63 | 253 | 511 | 0.25 |
| 4 | T | 0.80 | 0.17 | Poor | Poor | 78 | 321 | 623 | 0.31 |
| 5 | U | 0.70 | 0.10 | Fiar | Poor | 75 | 272 | 480 | 0.15 |
| 6 | V | 0.70 | ≦0.01 | Good | Good | 72 | 71 | 112 | 0.15 |
| 7 | W | 0.80 | 0.12 | Fiar | Fair to Good | 76 | 158 | 330 | 0.20 |
| 8 | X | 0.52 | 0.13 | Poor | Fair to Good | 73 | 158 | 326 | 0.15 |
| 9 | Y | 0.53 | 0.06 | Fiar | Good | 63 | 253 | 511 | 0.25 |
| 10 | Z | 0.51 | 0.21 | Poor | Fair to Good | 71 | 95 | 218 | 0.18 |

*[1]Breakage of the sheet was observed at the embossed portions.

Example 17

Preparation of Absorbent Article

A sanitary napkin having the structure of FIG. 12 was prepared as follows.

A 175 m long and 73 mm wide absorbent sheet (D) was used as the absorbent sheet 10. Fluff pulp 2a having a basis weight of 300 g/m² and a thickness of 4.5 mm, cut to a size of 175 mm length and 73 mm width, was laminated thereon. The sides and the upper part of the combination of absorbent sheet (D) and the fluff pulp were covered with 130 mm wide and 175 mm long wet-processed absorbent paper 2b consisting of wood pulp to prepare the absorbent member 2.

Waterproof paper 205 mm long and 95 mm wide (wet-processed absorbent paper having polyethylene laminated thereon) was used as the backsheet 3. The sides and the bottom of the absorbent member 2 was covered with the waterproof paper. All the surfaces of the combination of the absorbent member 2 and polyethylene-laminated paper were covered with the 205 mm long and 172 mm wide topsheet 1 capable of absorbing body liquids (hereinafter described), and all the members were fixed to each other with hot-melt adhesive 6. Finally, a pair of adhesive bands 4 each having a width of 20 mm and a length of 115 mm were provided on the bottom by applying a hot-melt adhesive at a spread of 30 g/m². Thus, the sanitary napkin having the structure shown in FIG. 12 was obtained.

A perforated polyethylene film was used as the topsheet 1. This film was obtained by perforating a polyethylene film having a basis weight of 30 g/m² to make openings having a diameter of 0.5 mm at a opening area ratio of 20%.

Example 18

Preparation of Absorbent Article

A sanitary napkin having the structure of FIG. 14 was prepared as follows.

A sanitary napkin having the structure of FIG. 14 was prepared in the same manner as in Example 14, except that the absorbent member was prepared by folding a 175 mm long and 145 mm wide absorbent sheet (B) into a C-shape in such a manner that both ends met substantially at the center of the folded sheet to make the width 73 mm. The absorbent sheet (B) was used as the absorbent layer.

Examples 19 to 30

Preparation of Absorbent Article

Sanitary napkins having the structure of FIG. 14 were prepared in the same manner as in Example 18, except for replacing absorbent sheet (B) with absorbent sheets (C) to (N).

Comparative Example 11

Preparation of Absorbent Article

Figure 20:
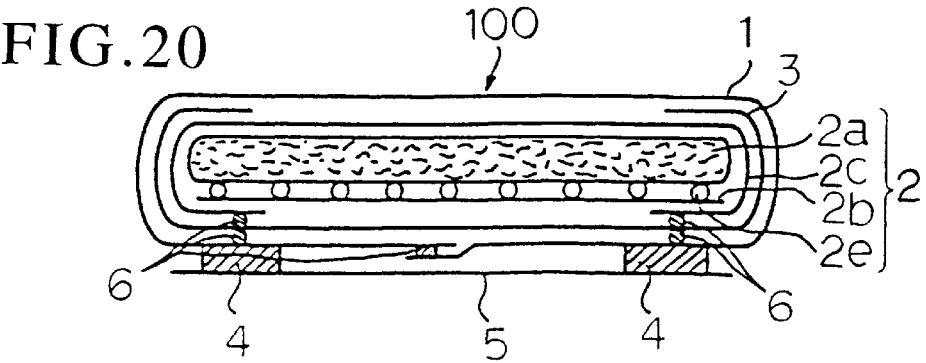
FIG. 20 is a schematic cross section of a conventional sanitary napkin.

A sanitary napkin having the structure of FIG. 20 was prepared as follows.

A small amount of water was spread over fluff pulp 2a having a basis weight of 300 g/m², a thickness of 4.5 mm, a length of 175 mm, and a width of 73 mm, and about 0.53 g of superabsorbent polymer 2e ("Aquaric CAW-4" produced by Nippon Shokubai Kagaku Kogyo Co., Ltd.) over the area of 60 mm (W)×175 mm (L) of the wetted fluff pulp 2a substantially uniformly (50 g-polymer/m²). Wet processed absorbent paper 2b made from wood pulp having a basis weight of 18 g/m², a length of 175 mm, and a width of 73 mm was overlaid on the polymer-spread side of the fluff pulp. All the surfaces of the combined members were covered with wet processed absorbent paper 2c made from wood pulp having a basis weight of 18 g/m², a length of 175 mm, and a width of 130 mm to prepare the absorbent member 2. The sanitary napkin 100 shown in FIG. 20 was prepared by using the resulting absorbent member in the same manner as in Example 14.

Comparative Example 12

Preparation of Absorbent Article

A sanitary napkin having the structure shown in FIG. 12 was prepared in the same manner as in Example 17, except for replacing the absorbent sheet (D) with the absorbent sheet (Q).

Comparative Examples 13 and 14

Preparation of Absorbent Article

Sanitary napkins having the structure shown in FIG. 12 were prepared in the same manner as in Example 17, except for replacing absorbent sheet (D) with each of the absorbent sheets (R) and (S).

Comparative Examples 15 to 22

Preparation of Absorbent Article

Sanitary napkins having the structure shown in FIG. 14 were prepared in the same manner as in Example 18, except for replacing the absorbent the sheet (B) with each of the absorbent sheets (Q) and (T) to (Z).

The polymer fixing performance and absorption performance of the sanitary napkins prepared in Examples 17 to 30 and Comparative Examples 11 to 22 were evaluated by testing in terms of fall-off of the polymer, thickness of the article, absorbing time, and back-flow and leakage in a moving mode according to the following test methods. The results obtained are shown in Table 2.

Test on Fall-off of Superabsorbent Polymer

A sanitary napkin was weighed and put in a 280 mm long and 200 mm wide polyethylene bag with a fastener. Vibration was given to the napkin by shaking the bag 50 times by the hand. After the test, the napkin was again weighed to obtain a change in weight. In order to facilitate visual observation of the superabsorbent polymer fallen in the bag, water tinted with Blue No. 1 (0.3 g/100 ml of water) was put into the bag to swell the fallen superabsorbent polymer. The degree of fall-off of the superabsorbent polymer was observed with the naked eye and graded as follows.

Good . . . Fall-off of superabsorbent polymer is hardly observed.

Fair . . . Slight fall-off of superabsorbent polymer is observed.

Poor . . . Considerable fall-off of superabsorbent polymer is observed.

Measurement of Product Thickness

Figure 21:
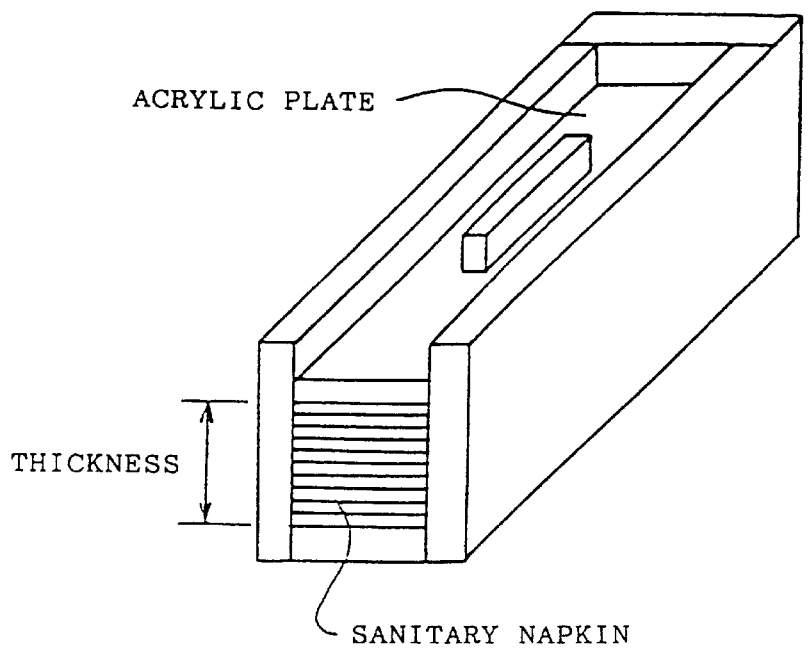
FIG. 21 is a schematic view illustrating the thickness of a sanitary napkin.
Figure 22:
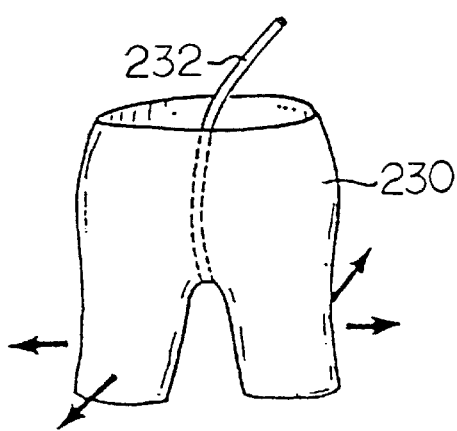
FIG. 22 illustrates a movable model of female hips and crotch.

As shown in FIG. 21, 10 sanitary napkins were piled up, and an acrylic plate weighing 500 g was put thereon. The total thickness of the pile under load was measured to obtain a thickness per single sanitary napkin.

Measurement of Absorbing Time (5 g), Re-absorbing Time (10 g), and Back-flow in Moving Mode A device for measuring the rate of absorption as shown in FIG. 18 was used for measurement. A sanitary napkin obtained in Examples 17 to 30 and Comparative Examples 11 to 22 was placed horizontally in place of absorbent sheet 200 shown in FIG. 18. Acrylic plate 220 having an inlet having a diameter of 1 cm was placed on the napkin, and weights 222 were put thereon to apply a load of 5 g/cm² to the sanitary napkin.

Five grams of defibrinated equine blood (produced by Nihon Biotest Kenkyusho K.K.) were poured through the inlet, and the time (sec) required for the blood to be absorbed completely was measured. After the complete absorption, the sanitary napkin was left to stand for 20 minutes. Then, another 5 g of defibrinated equine blood was again poured to obtain the time required for re-absorption (10 g), and the napkin was allowed to stand for 20 minutes.

Figure 23:
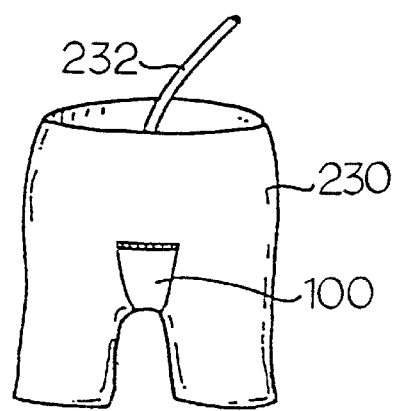
FIG. 23 illustrates the movable model of FIG. 22 with a sanitary napkin applied to the crotch.

Thereafter, 10 sheets of absorbent paper made from softwood pulp having a basis weight of 30 g/m², a length of 195 mm, and a width of 75 mm were placed on the upper side of the sanitary napkin (the side to be in contact with the body). The sanitary napkin with absorbent paper on was fixed to panties, and the panties were fitted onto movable model 230 of female hips and crotch as shown in FIG. 23. The model was made to take a walking movement at a rate of 100 steps/min (corresponding to a walking speed of 50 m/min) for 1 minute.

After the walking movement, the sanitary napkin 100 and 10 sheets of absorbent paper were removed, and the weight of defibrinated equine blood absorbed into the absorbent paper was measured as a back-flow (g). The test was conducted 5 times for each sample to obtain an average value for each of absorbing time, re-absorbing time, and back-flow in a moving mode.

Leak Test (Number of Leaks)

As shown in FIG. 23, the sanitary napkin 100 obtained in Examples 17 to 30 and Comparative Examples 11 to 22 was fitted to panties and applied to a movable model 230 of female hips and crotch. The model 230 was made to take a walking movement at a rate of 100 steps/min (corresponding to a walking speed of 50 m/min) for 10 minutes.

While keeping the model 230 in a moving mode, 5 g of defibrinated equine blood was poured into the sanitary napkin 100 through a tube 232, and the walking movement was continued for an additional period of 20 minutes at the same walking speed (5 g-absorption). Another 5 g of defibrinated equine blood was again poured, followed by walking at the same speed for another 20 minutes (10 g-absorption). The test was conducted 10 times per sample, and the samples having a leak at 5 g-absorption and 10 g-absorption were counted.

TABLE 2

Polymer Fall-off Teset

| | | Product | | Visual | Absorbing Time (sec) | | | Number of Leaking Samples | |
|---|---|---|---|---|---|---|---|---|---|
| | Absorbenet Sheet | Thickness (mm) | Fall-off (g) | Observation | 5 g | 10 g (Re-absorption) | Back-flow (g) | 5 g | 10 g |
| Examples | | | | | | | | | |
| 17 | D | 6.1 | ≦0.01 | Good | 7 | 14 | 0.3 | 0 | 2 |
| 18 | B | 2.3 | ≦0.01 | Good | 23 | 37 | 0.2 | 0 | 3 |
| 19 | C | 2.3 | ≦0.01 | Good | 19 | 35 | 0.2 | 0 | 1 |
| 20 | D | 2.5 | ≦0.01 | Good | 15 | 22 | 0.1 | 0 | 0 |
| 21 | E | 3.5 | 0.01 | Fair to Good | 16 | 21 | 0.2 | 0 | 1 |
| 22 | F | 2.3 | ≦0.01 | Good | 13 | 20 | 0.2 | 0 | 1 |
| 23 | G | 2.3 | ≦0.01 | Good | 15 | 25 | 0.2 | 0 | 2 |
| 24 | H | 2.4 | ≦0.01 | Good | 9 | 15 | 0.1 | 0 | 0 |
| 25 | I | 2.5 | ≦0.01 | Good | 12 | 18 | 0.1 | 0 | 0 |
| 26 | J | 2.5 | ≦0.01 | Good | 8 | 14 | 0.1 | 0 | 0 |
| 27 | K | 2.6 | ≦0.01 | Good | 11 | 16 | 0.1 | 0 | 0 |
| 28 | L | 2.5 | ≦0.01 | Good | 8 | 14 | 0.1 | 0 | 0 |
| 29 | M | 2.4 | ≦0.01 | Good | 15 | 24 | 0.2 | 0 | 1 |
| 30 | N | 2.3 | ≦0.01 | Good | 17 | 28 | 0.2 | 0 | 2 |
| Comparative Examples | | | | | | | | | |
| 11 | Thick Type | 5.9 | 0.15 | Poor | 9 | 18 | 0.6 | 0 | 4 |
| 12 | Q | 6.0 | 0.11 | Poor | 12 | 23 | 0.5 | 0 | 4 |
| 13 | R | 6.1 | 0.13 | Poor | 10 | 21 | 0.5 | 0 | 5 |
| 14 | S | 6.0 | 0.04 | Fair | 11 | 22 | 0.7 | 0 | 5 |
| 15 | Q | 2.0 | 0.15 | Poor | 62 | 185 | 1.0 | 1 | 7 |
| 16 | T | 2.5 | 0.21 | Poor | 82 | 243 | 0.15 | 3 | 10 |
| 17 | U | 2.3 | 0.15 | Poor | 73 | 212 | 1.1 | 2 | 8 |
| 18 | V | 2.3 | ≦0.01 | Good | 65 | 95 | 1.0 | 3 | 9 |
| 19 | W | 2.0 | 0.13 | Poor | 70 | 195 | 1.0 | 3 | 10 |
| 20 | X | 2.1 | 0.11 | Poor | 58 | 177 | 0.6 | 1 | 7 |
| 21 | Y | 2.2 | 0.04 | Fair | 56 | 160 | 0.6 | 1 | 6 |
| 22 | Z | 2.2 | 0.13 | Poor | 70 | 190 | 0.9 | 3 | 10 |

As is apparent from the results in Tables 1 and 2, the absorbent articles according to the present invention, in which an absorbent sheet comprising a fiber web and a fiber aggregate in a unitary body and having contained therein a superabsorbent polymer is used, are excellent in terms of fixing of the superabsorbent polymer as compared with conventional absorbent articles using conventional absorbent sheets in which the superabsorbent polymer is integrated by water spreading, embossing or application of adhesives. Even in using such a thin absorbent sheet as has a thickness of 2 to 3 mm, the absorbent articles of the present invention exhibit excellent absorption characteristics in terms of rate of absorption, back-flow, and the like.

Further, in spite of a very simple structure, the absorbent articles of the present invention exhibit extremely high performance, having a high rate of absorption and a small back-flow, and being prevented from leaking. This is because the absorbent sheet used therein has a gradient in the manner of liquid diffusion within its unitary structure so that liquid is quickly absorbed and smoothly permeates through the absorbent sheet while sufficiently diffusing.

Many other variations and modifications of the invention will be apparent to those skilled in the art without departing from the spirit and scope of the invention. The above-described embodiments are, therefore, intended to be merely exemplary, and all such variations and modifications are intended to be included within the scope of the invention as defined in the appended claims.

What is claimed is:

1. An absorbent sheet comprising (a) hydrophilic fibers; (b) thermally fusible bonding fibers or a strengthening assistant selected from the group consisting of polyamine-epichlorohydrin resin, dialdehyde starch, and carboxymethyl cellulose; and (c) superabsorbent polymer particles, wherein:

the superabsorbent polymer particles are not present on an absorbent surface of the absorbent sheet for absorbing liquid but distributed inside the absorbent sheet, and are adhered and fixed to the hydrophilic fibers constituting the absorbent sheet;

the superabsorbent polymer particles are spread at an amount of 5 to 300 g per 1 m² of the absorbent sheet; and the absorbent sheet has a thickness of 0.3 to 1.5 mm.

2. The absorbent sheet according to claim 1, wherein the absorbent sheet comprises a first fiber layer and a second fiber layer which form a unitary body;

the first fiber layer having an absorbent layer surface and containing no superabsorbent polymer particles on the absorbent surface side;

the second fiber layer comprising at least the hydrophilic fibers and having superabsorbent polymer particles predominately distributed inside the second fiber layer.

3. The absorbent sheet according to claim 2, wherein the first fiber layer has a basis weight of 10 to 200 g/m², and the second fiber layer has a basis weight of 10 to 200 g/m².

4. The absorbent sheet according to claim 1, wherein the hydrophilic fibers are bulky cellulose fibers.

5. The absorbent sheet according to claim 4, wherein the bulky cellulose fibers have a degree of fiber roughness of 0.3 mg/m or more.

6. The absorbent sheet according to claim 4, wherein the bulky cellulose fibers have a degree of fiber roundness in the fiber cross section of 0.5 to 1.

7. The absorbent sheet according to claim 4, wherein the bulky cellulose fibers are crosslinked cellulose fibers.

8. An absorbent sheet which comprises superabsorbent polymer particles, and a fiber structure comprising bulky hydrophilic cellulose fibers and thermally fusible bonding fibers or a strengthening assistant selected from the group consisting of polyamine, epichlorohydrin resin, dialdehyde, and carboxymethyl cellulose;

the superabsorbent polymer particles being not present on an absorbent surface of the absorbent sheet for absorbing the liquid but distributed inside and fixed to the fiber structure;

the absorbent sheet having a thickness of 0.3 to 1.5 mm, and the superabsorbent polymer being spread at an amount of 20 to 70 g per 1 $m^2$ of the absorbent sheet.

9. An absorbent article comprising at least a liquid retentive absorbent member and a liquid impermeable backsheet wherein the absorbent member comprises the absorbent sheet according to claim 1.

10. An absorbent article for absorbing body fluids comprising at least a liquid retentive absorbent member and a liquid impermeable backsheet wherein absorbent member comprises the absorbent sheet according to claim 8;

said absorbent article does not provide an uncomfortable feeling caused by absorption of the body fluids and swelling of the superabsorbent polymer particles during usage.

11. The absorbent sheet according to claim 2, wherein the first fiber layer predominately comprises bulky cellulose fibers having a degree of fiber roughness of 0.3 mg/m or more; and the second fiber layer comprises a permeable layer predominantly comprising bulky cellulose fibers having a degree of fiber roughness of 0.3 mg/m or more and a diffusing layer located adjacent to the permeable layer and comprising bulky cellulose fibers having a degree of fiber roughness of 0.3 mg/m or more and hydrophilic fine fibers, the second fiber layer located adjacent to the first fiber layer at the permeable layer.

12. The absorbent sheet according to claim 2, wherein the first fiber layer comprises a permeable layer predominantly comprising bulky cellulose fibers having a degree of fiber roughness of 0.3 mg/m or more and a diffusing layer located adjacent to the permeable layer and comprising bulky cellulose fibers having a degree of fiber roughness of 0.3 mg/m or more and hydrophilic fine fibers; and the second fiber layer predominately comprises bulky cellulose fibers having a degree of fiber roughness of 0.3 mg/m or more and located adjacent to the diffusing layer of the first fiber layer.

13. The absorbent sheet according to claim 2, wherein the first fiber layer predominately comprises bulky cellulose fibers having a degree of fiber roughness of 0.3 mg/m or more; and the second fiber layer comprises bulky cellulose fibers having an average fiber length of 1 to 20 mm and a degree of fiber roughness of 0.3 mg/m or more and hydrophilic fine fibers having an average fiber length of 0.02 to 0.5 mm, the proportion of the hydrophilic fine fibers being greater in one of two sides of the second fiber layer, and the second fiber layer located adjacent to the first fiber layer at the side having a lower proportion of the hydrophilic fine fibers.

14. The absorbent sheet according to claim 2, wherein the first fiber layer comprises bulky cellulose fibers having an average fiber length of 1 to 20 mm and a degree of fiber roughness of 0.3 mg/m or more and hydrophilic fine fibers having an average fiber length of 0.02 to 0.5 mm, the proportion of the hydrophilic fine fibers being higher on one of two sides of the first fiber layer than on the other side; and the second fiber layer comprises bulky cellulose fibers having a degree of fiber roughness of 0.3 mg/m or more, and located adjacent to the side of the first fiber layer having a lower proportion of the hydrophilic fine fibers.

15. The absorbent sheet according to claim 2, wherein the second fiber layer comprises bulky cellulose fibers and further contains hydrophilic fine fibers or hydrophilic fine particles contained mainly in the area where the superabsorbent polymer is present.

* * * * *

UNITED STATES PATENT AND TRADEMARK OFFICE
CERTIFICATE OF CORRECTION

PATENT NO. : 5,821,179
DATED      : October 13, 1998
INVENTOR(S): Masaki et al.

It is certified that error appears in the above-identified patent and that said Letters Patent is hereby corrected as shown below:

On the title page, Item [30],

IN THE FOREIGN APPLICATION PRIORITY DATA

CHANGE

"December 28, 1994 [JP] Japan ........... 6-348802"

TO

--December 28, 1994 [JP] Japan ........... 6-328802--

Signed and Sealed this

Thirteenth Day of July, 1999

Attest:

Attesting Officer

Q. TODD DICKINSON

Acting Commissioner of Patents and Trademarks